United States Patent
Rinaldi et al.

(10) Patent No.: US 11,311,630 B2
(45) Date of Patent: Apr. 26, 2022

(54) MAGNETIC PARTICLE CONJUGATES, MICELLES, AND METHODS OF DELIVERING AGENTS

(71) Applicant: University of Florida Research Foundation, Inc., Gainesville, FL (US)

(72) Inventors: Carlos Rinaldi, Gainesville, FL (US); Sun Hao, Wilmette, IL (US); Brent S. Sumerlin, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 16/937,014

(22) Filed: Jul. 23, 2020

(65) Prior Publication Data
US 2020/0353095 A1 Nov. 12, 2020

Related U.S. Application Data

(63) Continuation of application No. 16/093,370, filed as application No. PCT/US2017/028852 on Apr. 21, 2017, now Pat. No. 10,765,744.

(60) Provisional application No. 62/328,053, filed on Apr. 27, 2016.

(51) Int. Cl.
*A61K 47/69* (2017.01)
*A61K 47/60* (2017.01)
*A61K 47/52* (2017.01)

(52) U.S. Cl.
CPC .......... *A61K 47/6907* (2017.08); *A61K 47/52* (2017.08); *A61K 47/60* (2017.08)

(58) Field of Classification Search
CPC .... A61K 47/6907; A61K 47/60; A61K 47/52; A61K 47/6935; A61K 47/6933; A61K 47/6929; A61K 47/6923
See application file for complete search history.

(56) References Cited

U.S. PATENT DOCUMENTS

| | | |
|---|---|---|
| 2011/0212163 A1 | 9/2011 | Hoare et al. |
| 2012/0265001 A1 | 10/2012 | Asmatulu et al. |
| 2012/0302516 A1 | 11/2012 | Nantz et al. |
| 2013/0045160 A1 | 2/2013 | Ham et al. |
| 2013/0089614 A1 | 4/2013 | Zhang et al. |
| 2014/0072602 A1 | 3/2014 | Kwon |

(Continued)

FOREIGN PATENT DOCUMENTS

| | | |
|---|---|---|
| WO | WO2012082382 A1 | 6/2012 |
| WO | WO2016023036 A1 | 2/2016 |

OTHER PUBLICATIONS

Jon Dobson, "Magnetic nanoparticles for drug delivery", Drug Development Research, Special Issue: Nanobiotechnology, vol. 67, Issue 1, Jan. 2006, pp. 55-60.

(Continued)

*Primary Examiner* — Carlos A Azpuru
(74) *Attorney, Agent, or Firm* — Thomas|Horstemeyer, LLP

(57) ABSTRACT

Embodiments of the present disclosure provide for magnetic particle conjugates, methods of making the magnetic particle conjugates, methods of using magnetic particle conjugates, micelles (also referred to as a "magnetic composite nanocarrier" (MCNC)), methods of making micelles, methods of using micelles, and the like.

20 Claims, 36 Drawing Sheets

(56) References Cited

U.S. PATENT DOCUMENTS

2015/0204857 A1 7/2015 Clarke
2016/0058702 A1* 3/2016 Sansanaphongpricha ............... A61K 47/34
604/20

OTHER PUBLICATIONS

Beata Chertok, et al., "Iron oxide nanoparticles as a drug delivery vehicle for MRI monitored magnetic targeting of brain tumors", Biomaterials, vol. 29, Issue 4, Feb. 2008, pp. 487-496.

Morteza Mahmoudi, et al., "Superparamagnetic Iron Oxide Nanoparticles with Rigid Cross-linked Polyethylene Glycol Fumarate Coating for Application in Imaging and Drug Delivery", J. Phys. chem. C, Mar. 2009, 113(19), pp. 8124-8131.

Tapan K. Jain, et al., "Iron Oxide Nanoparticles for Sustained Delivery of Anticancer Agents", Mol. Pharm., 2005, 2(3), pp. 194-205.

J. Zhang et al., "On the chemical synthesis and drug delivery response of folate receptor-activated, polyethylene glycol-functionalized magnetite nanoparticles", Acta Biomaterialia, vol. 4, Issue 1, Jan. 2008, pp. 40-48.

Nathan Kohler et al, "A Bifunctional Poly(ethylene glycol) Silane Immobilized on Metallic Oxide-Based Nanoparticles for conjugation with Cell Targeting Agents", J. Am. chem. Soc., 2004, 126(23), pp. 7206-7211.

International Search Report and Written Opinion for PCT/US1728852 dated Jul. 17, 2017, 14 pages.

Zhou et al, Stimuli Responsive Polymeric Micelles for Drug Delivery and Cancer Treatment, INt J. Nanomedicine, 13:2921-2942 (year: 2018).

* cited by examiner

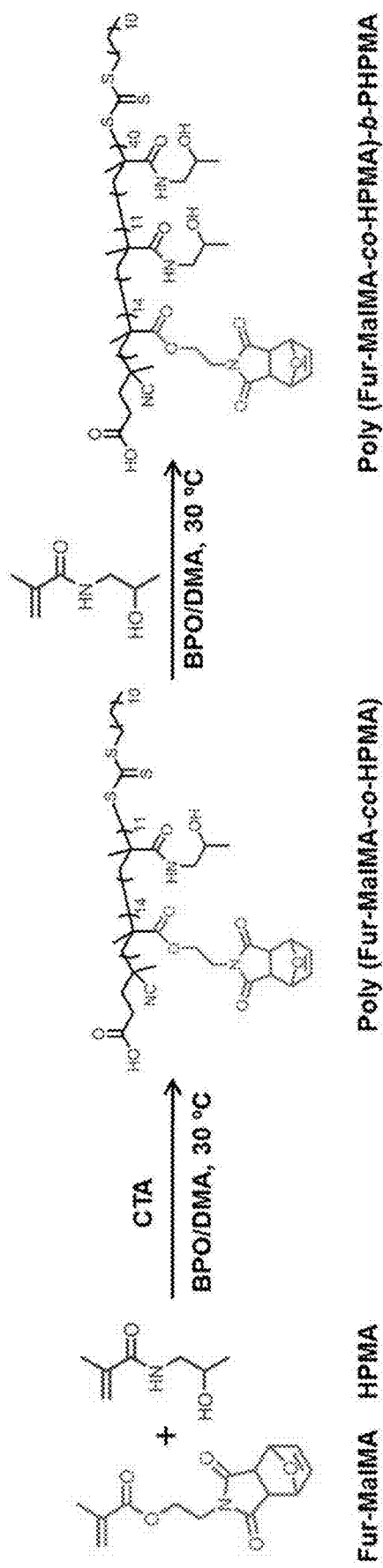
Fig. 1.1

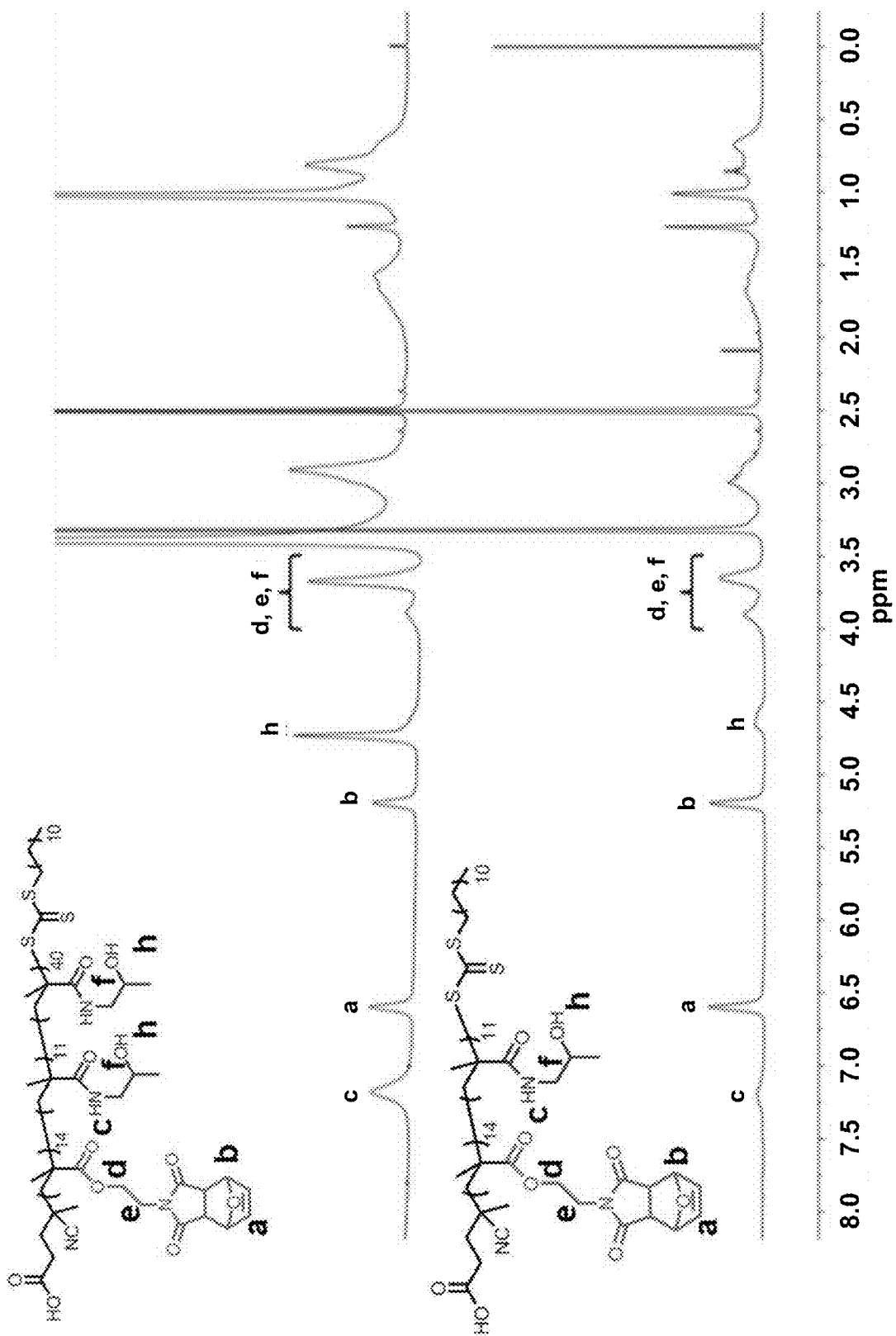
Fig. 1.2

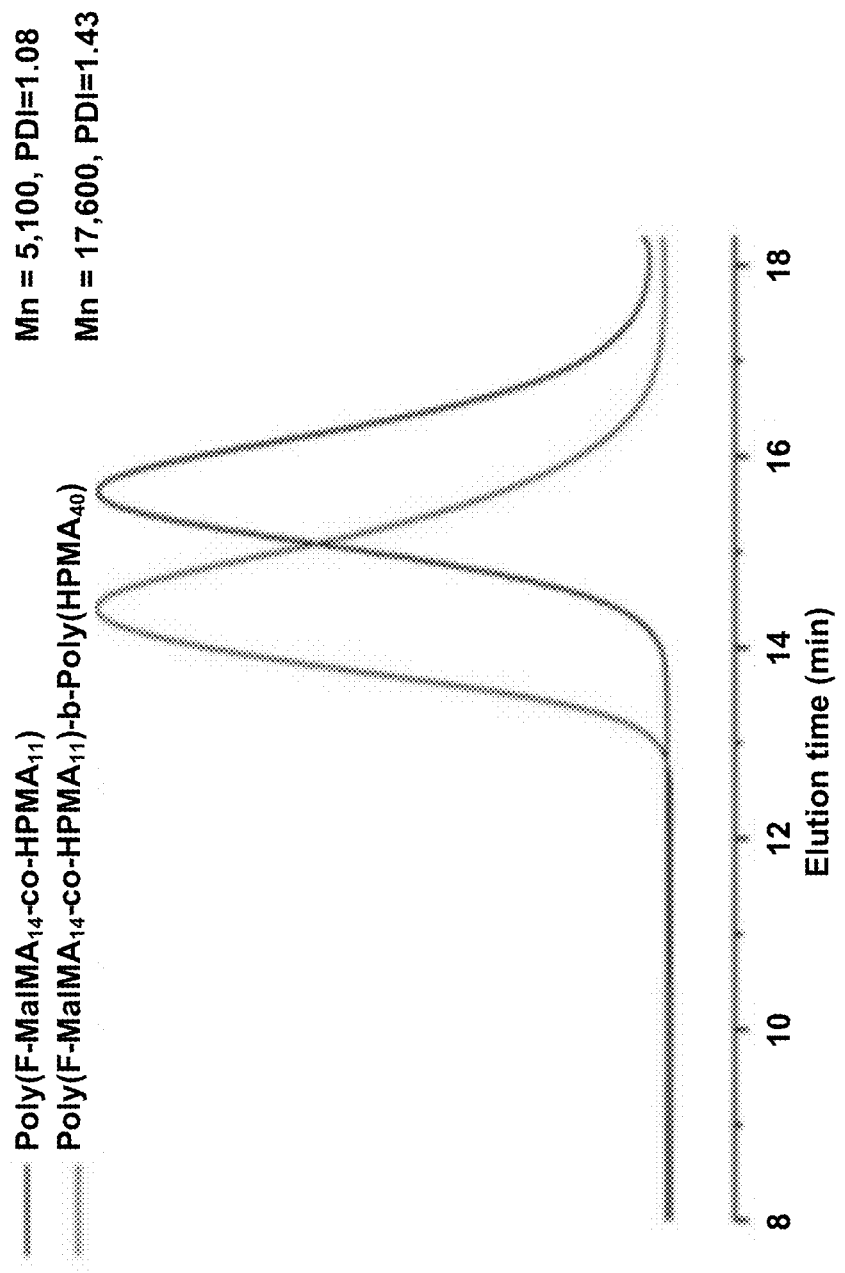

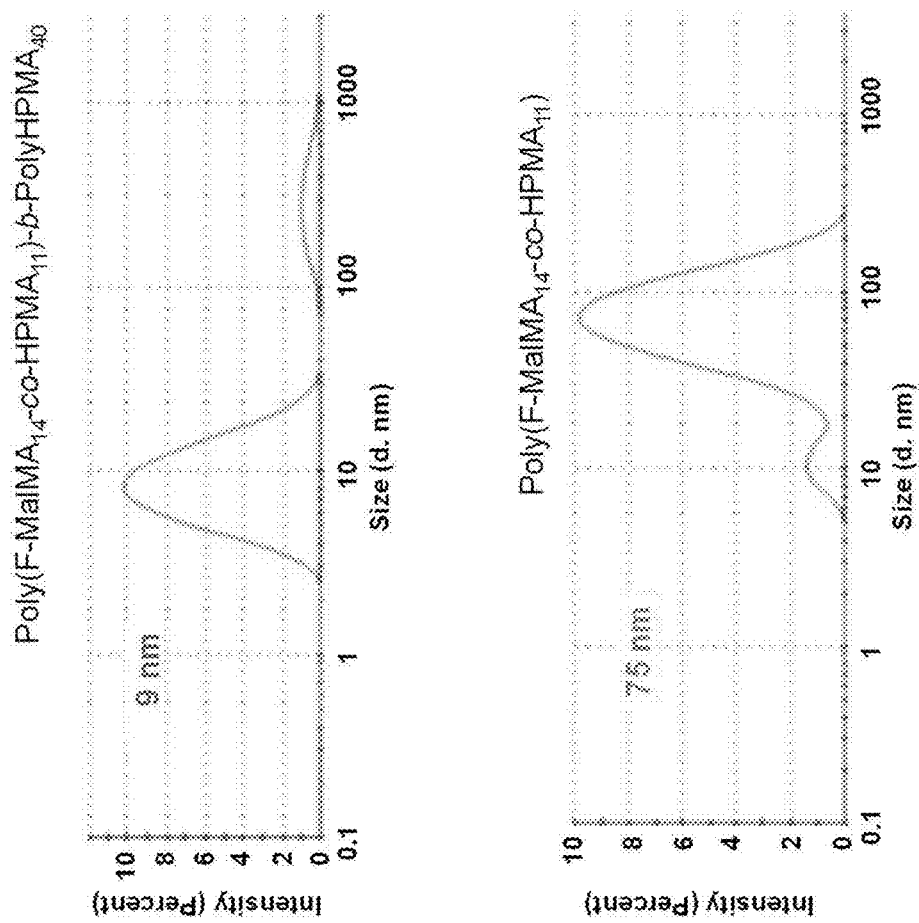
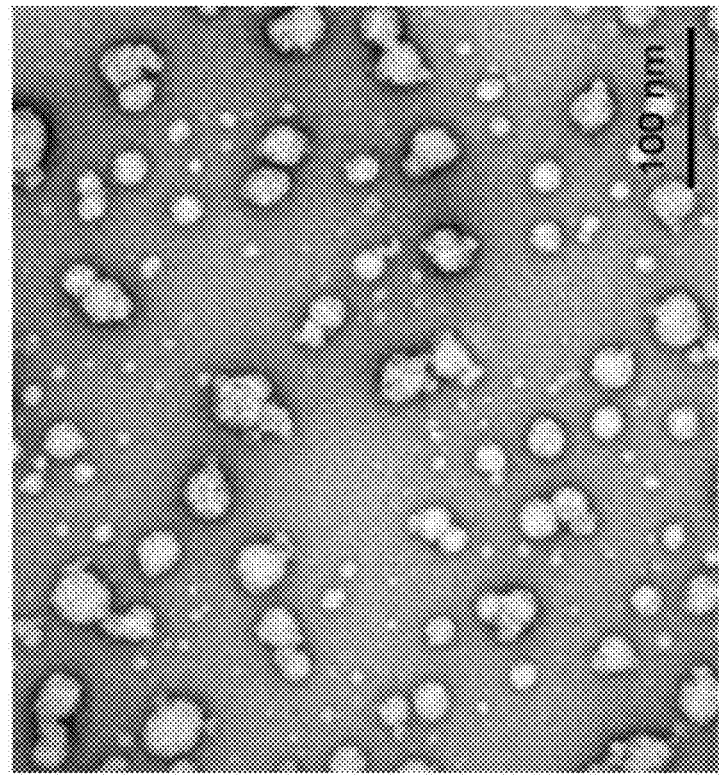
Fig. 1.4A
Fig. 1.4B

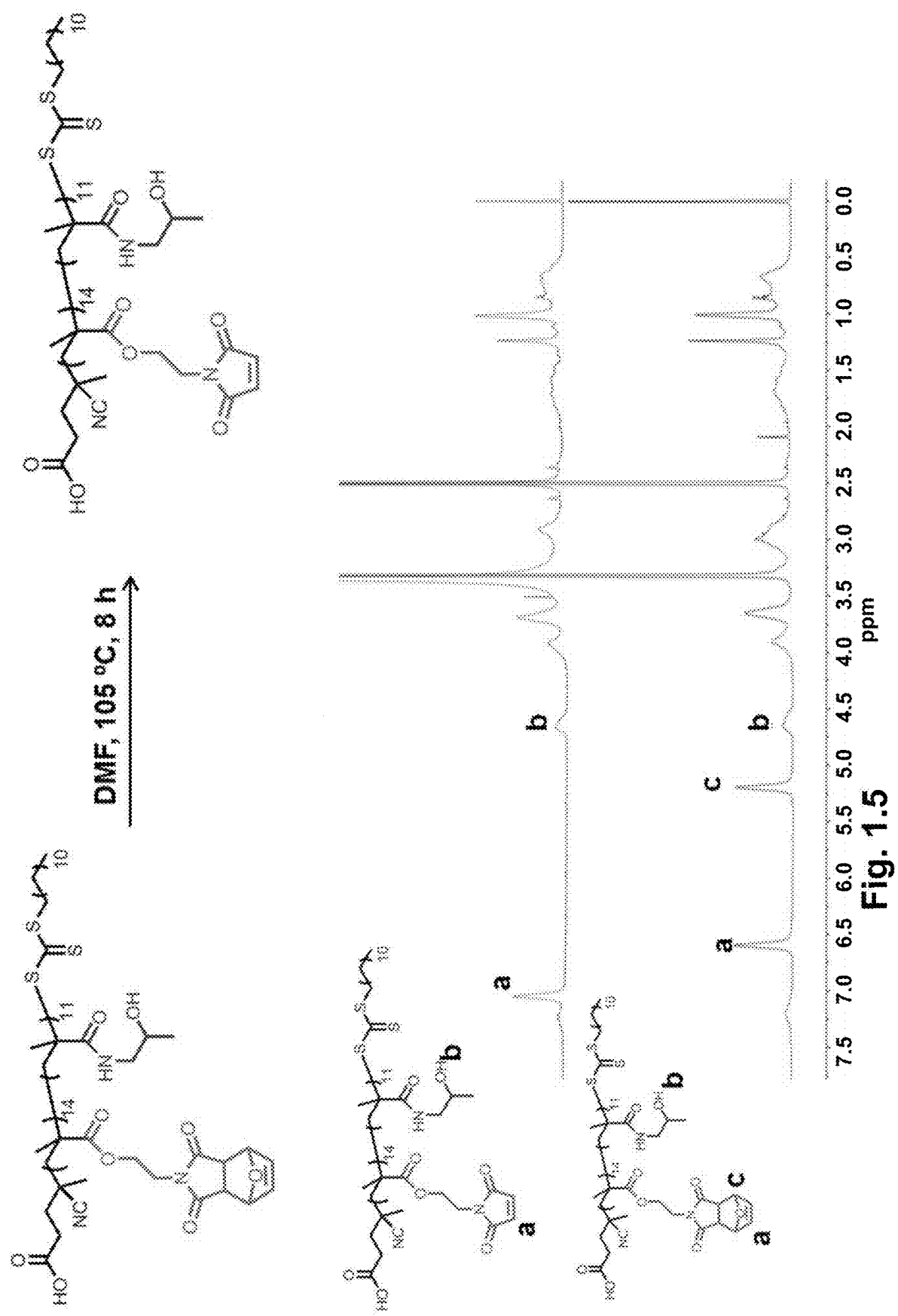
Fig. 1.5

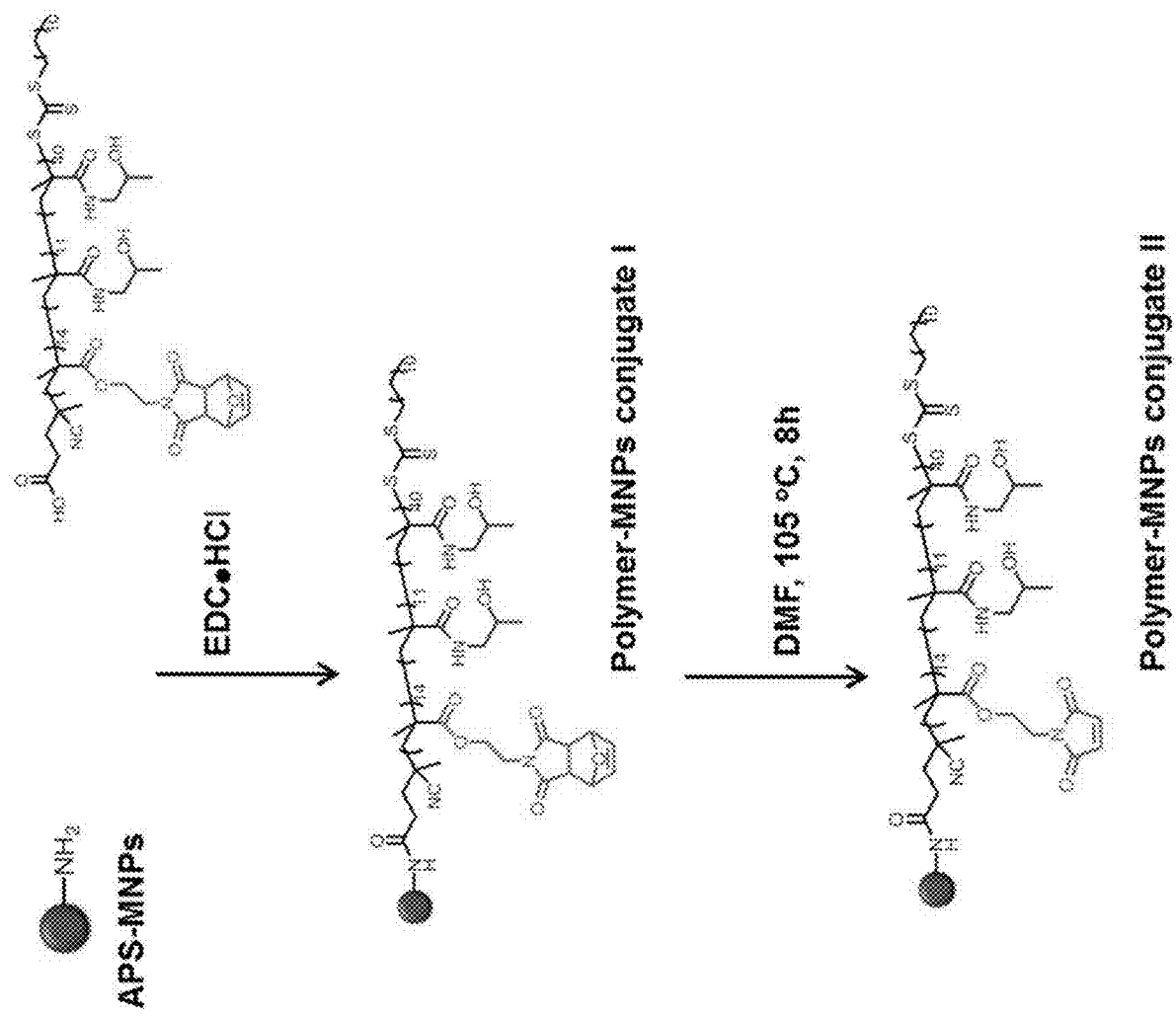
Fig. 1.6

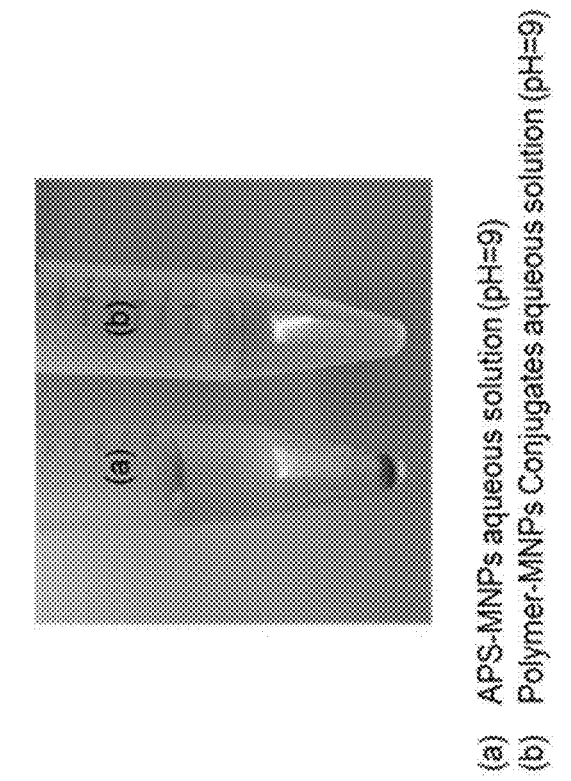
(a) APS-MNPs aqueous solution (pH=9)
(b) Polymer-MNPs Conjugates aqueous solution (pH=9)
Fig. 1.7B
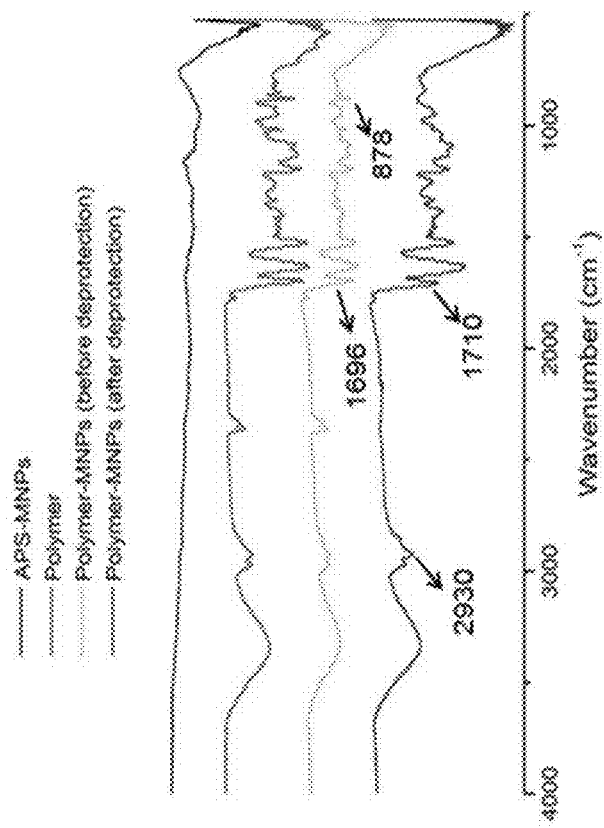
Fig. 1.7A

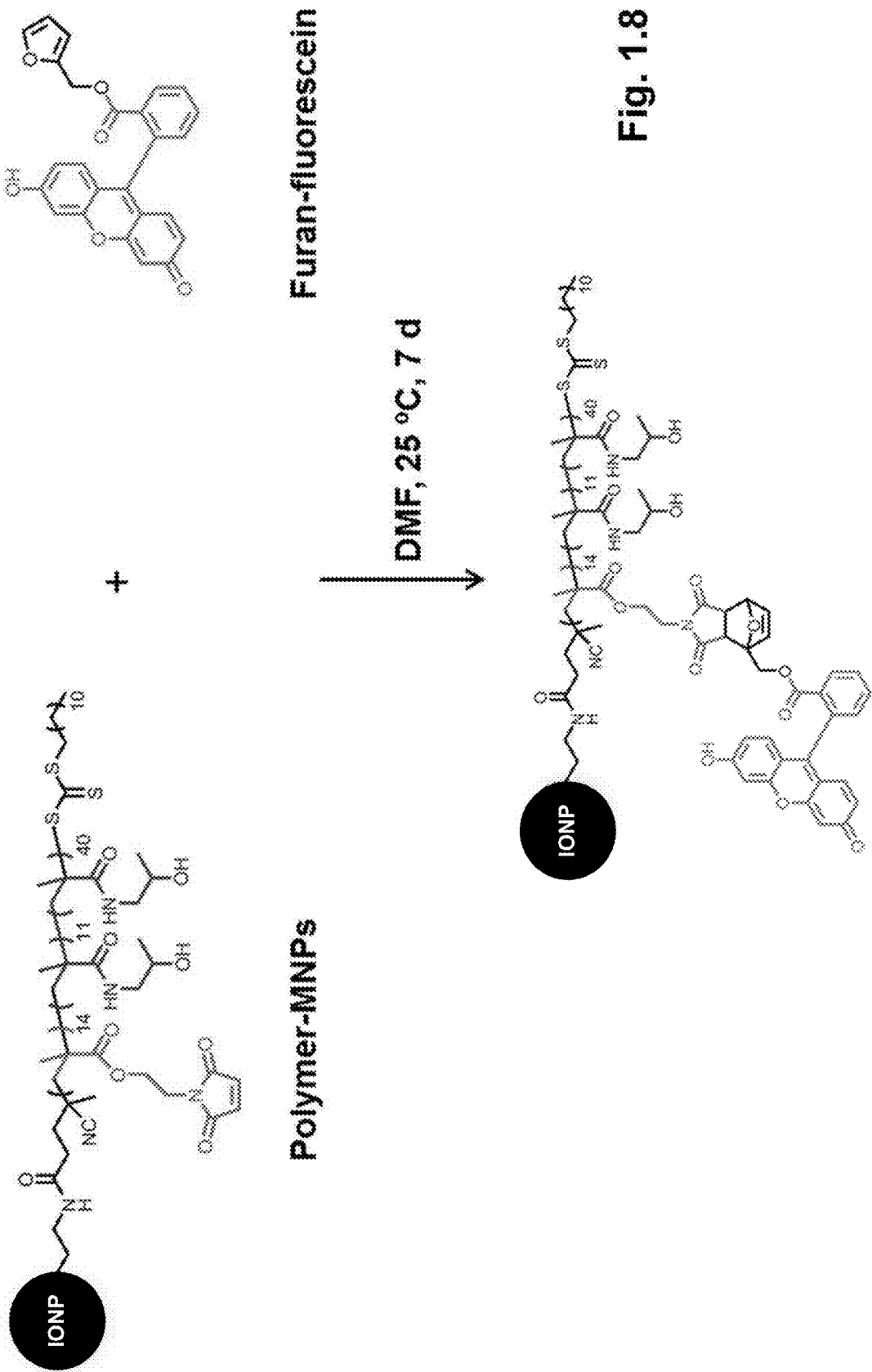
Fig. 1.8

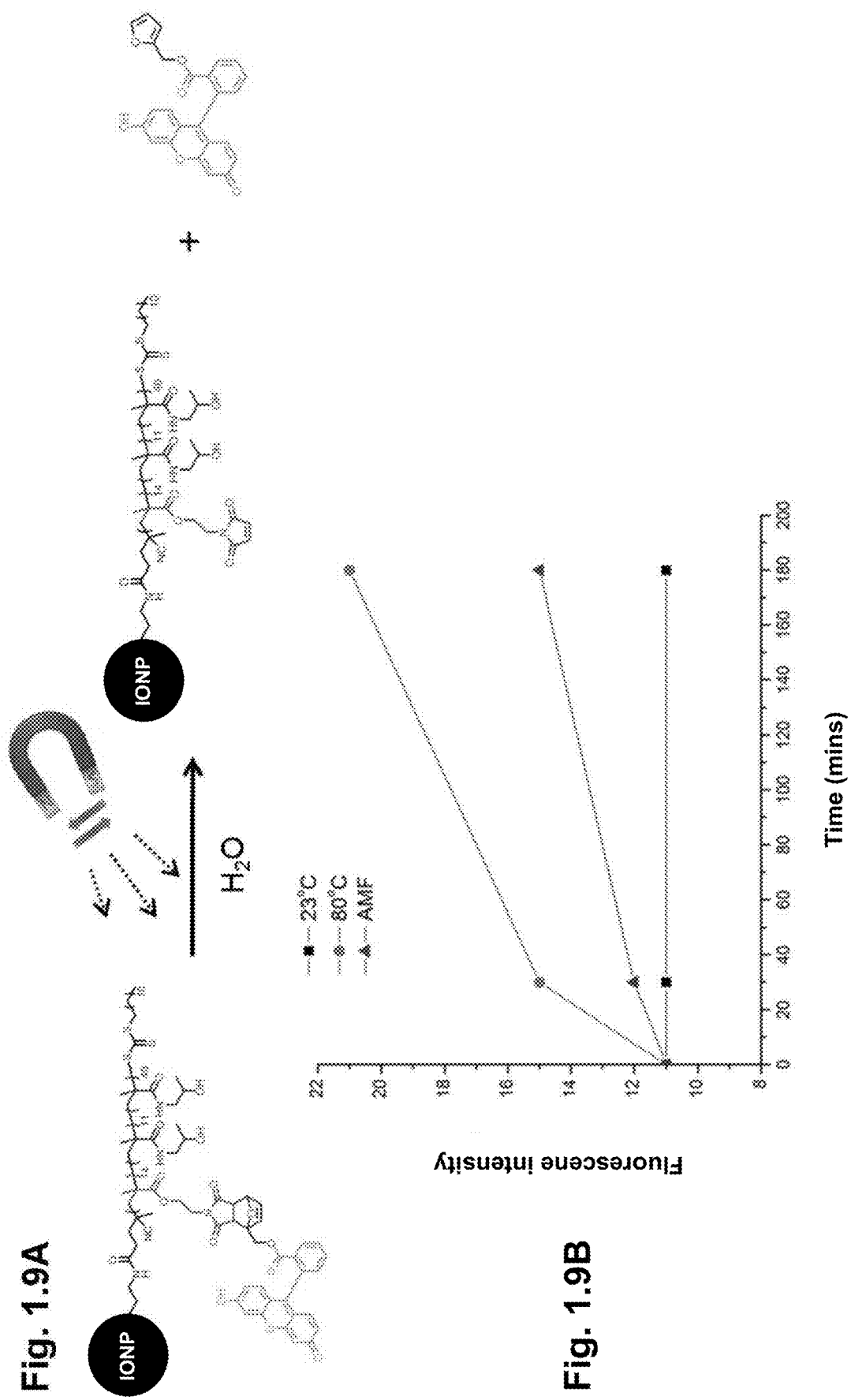
Fig. 1.9A
Fig. 1.9B

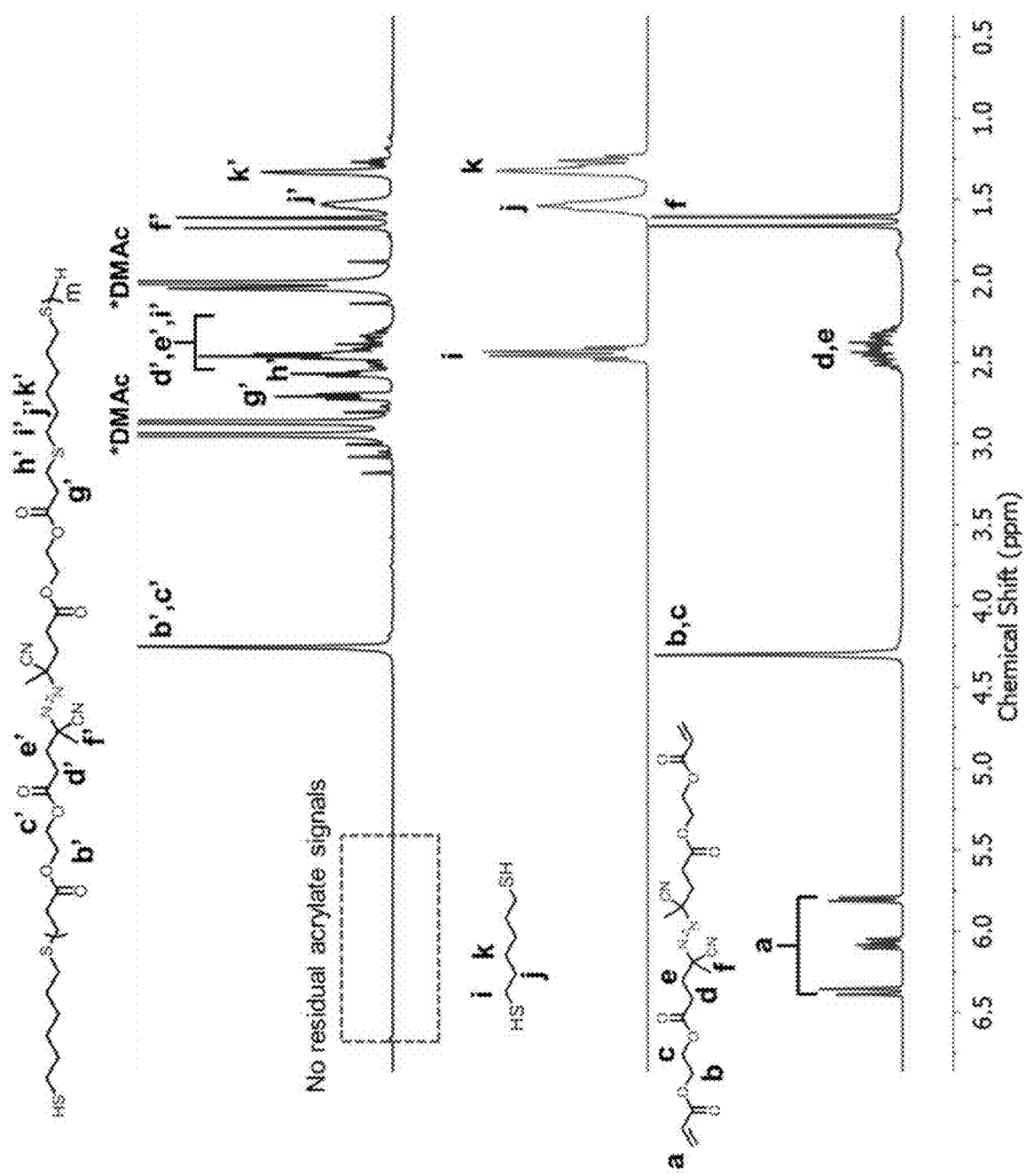
Fig. 2.1A

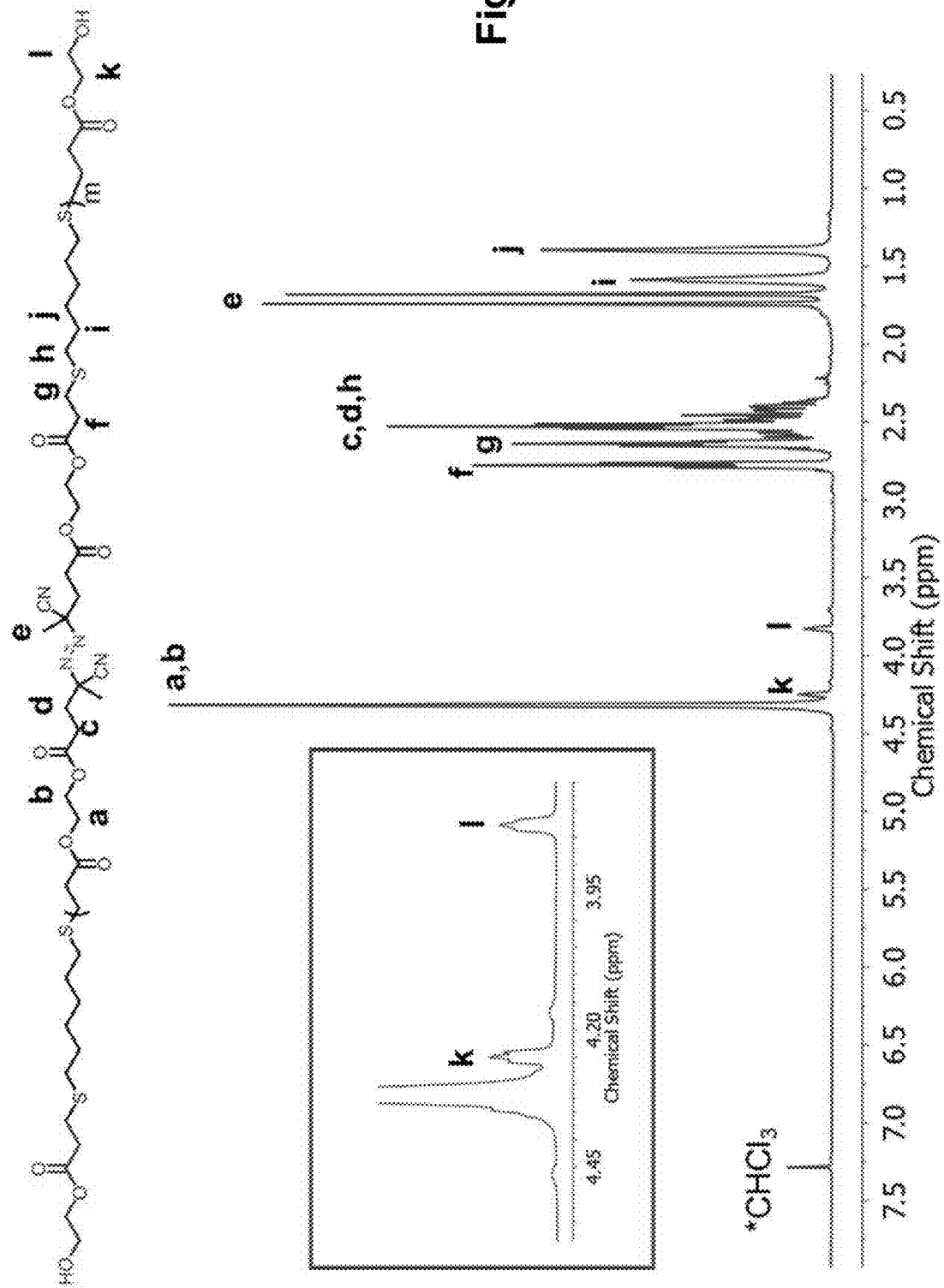
Fig. 2.1B

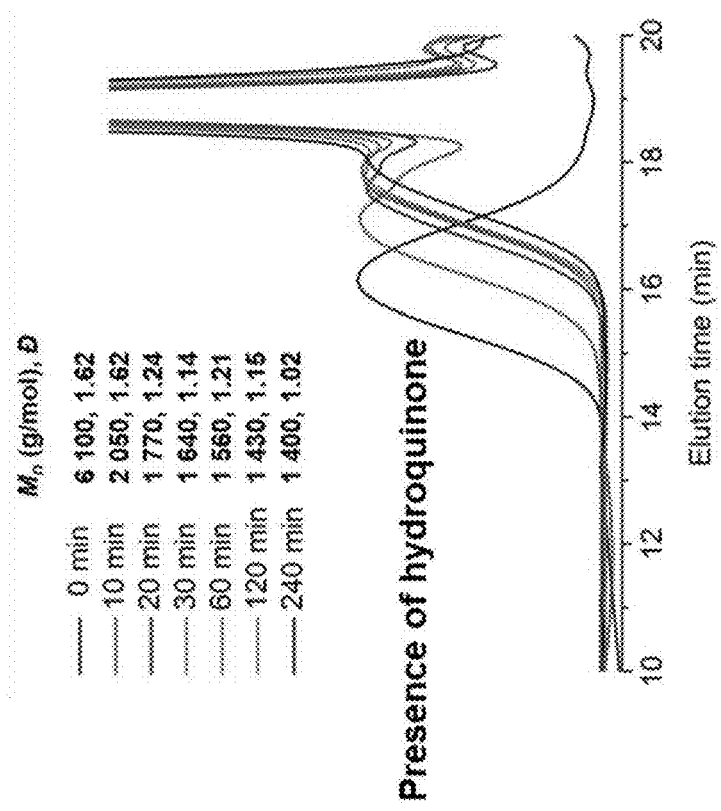
Fig. 2.2B
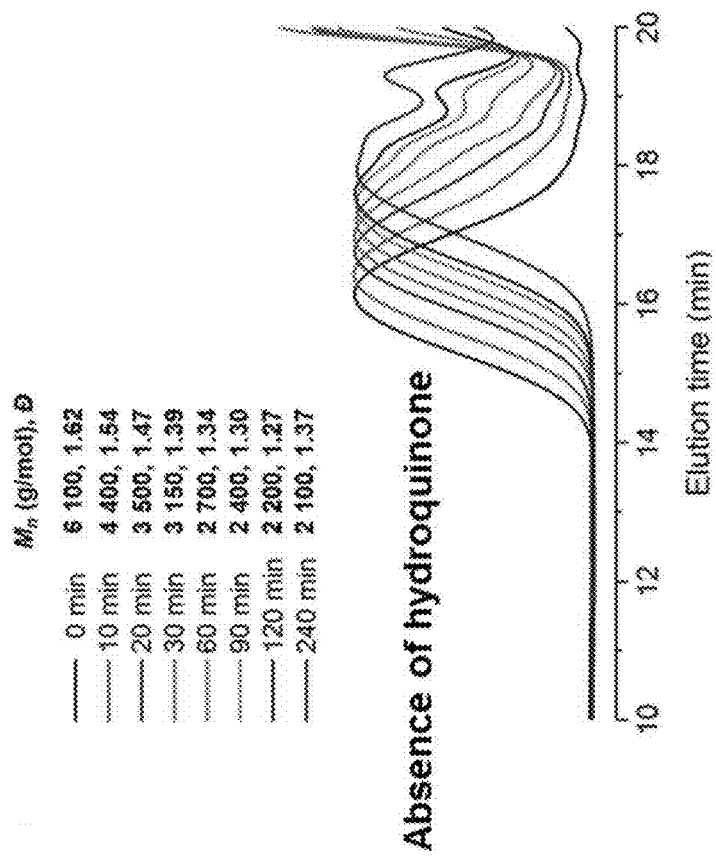
Fig. 2.2A

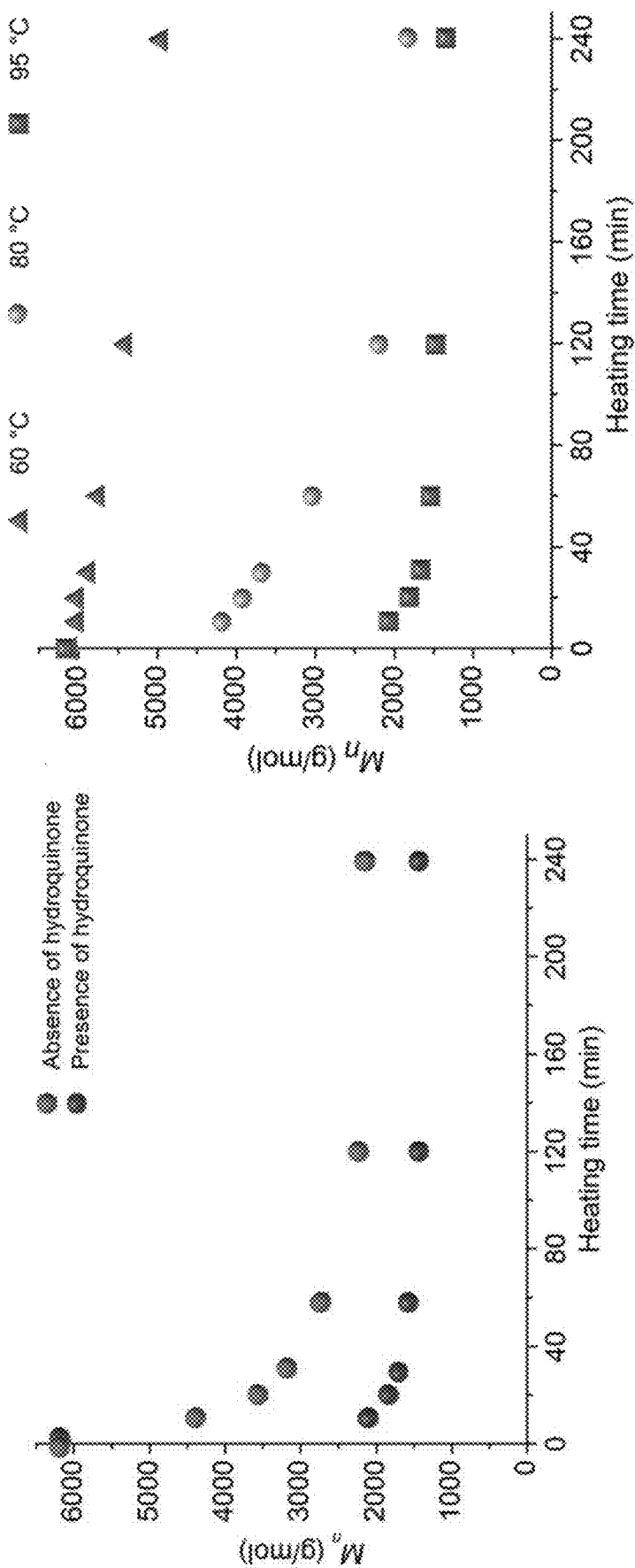
Fig. 2.2D
Fig. 2.2C

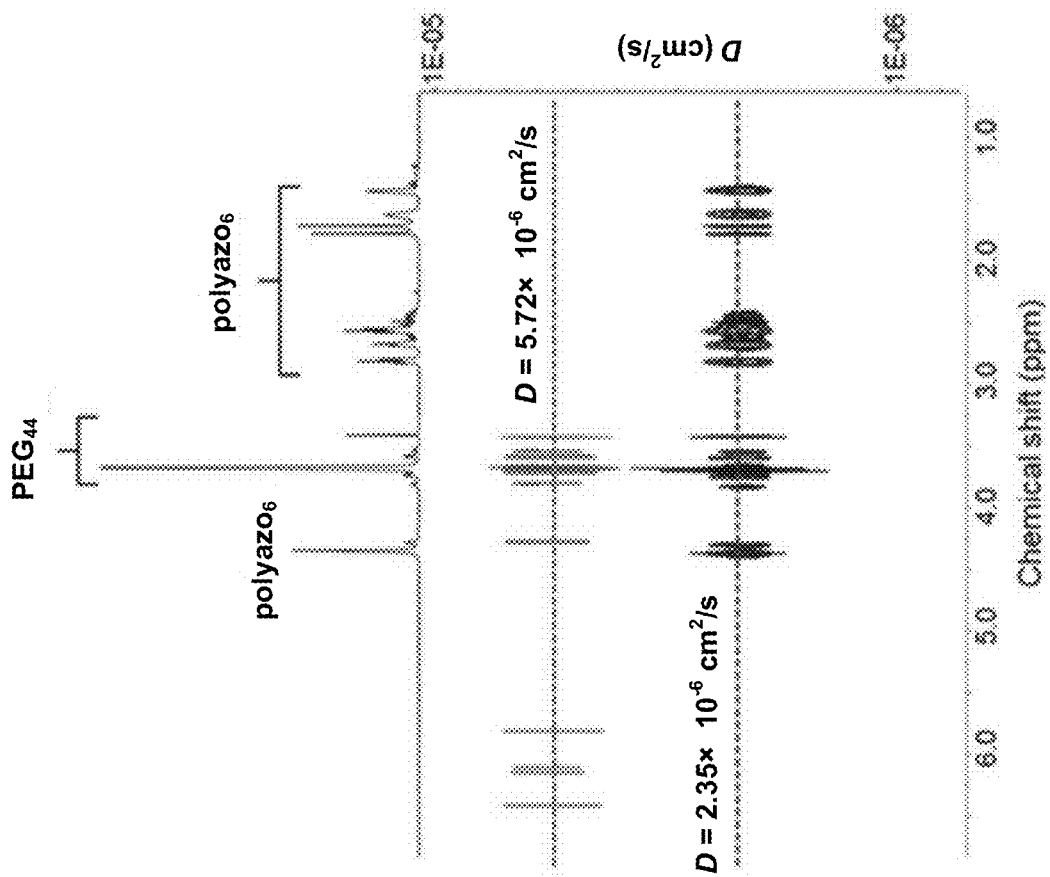
Fig. 2.3B
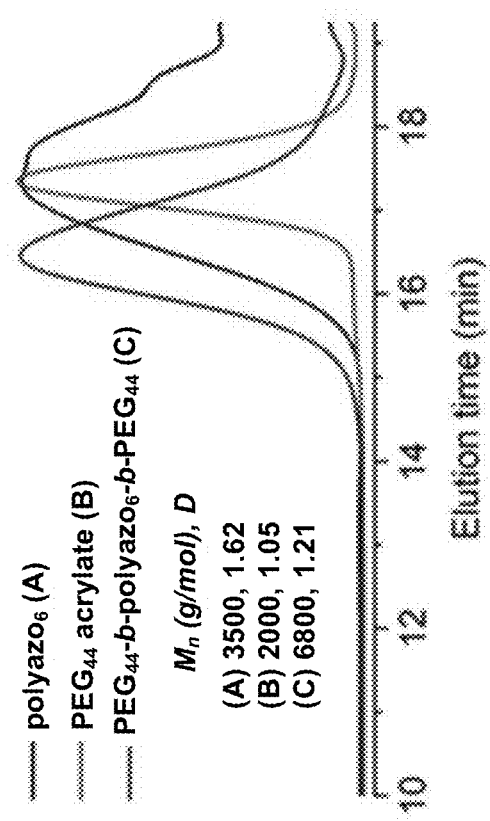
Fig. 2.3A

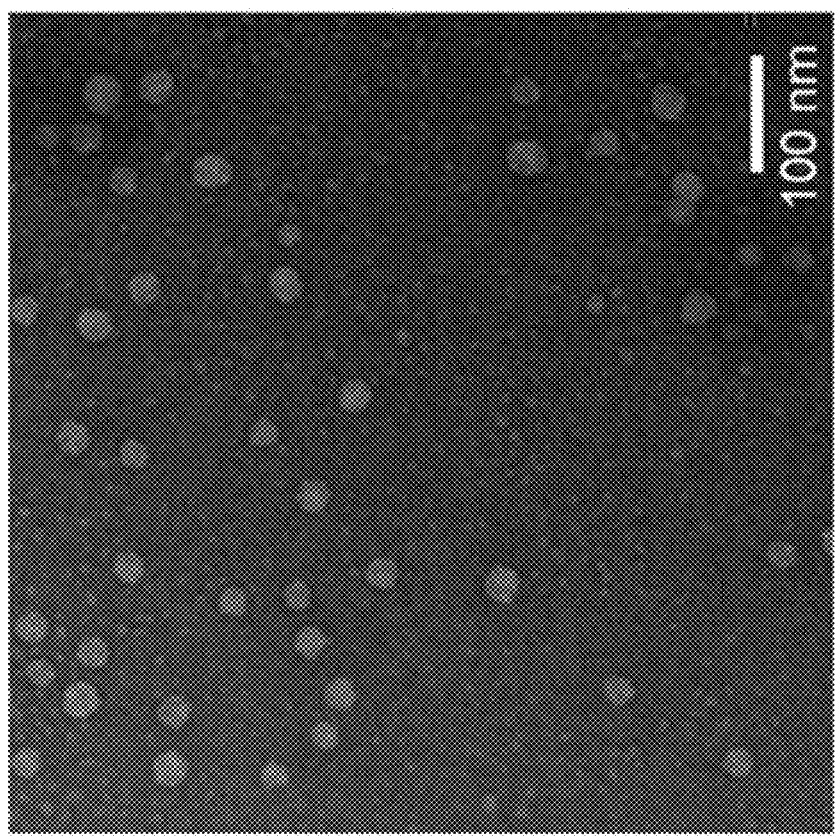
Fig. 2.3D
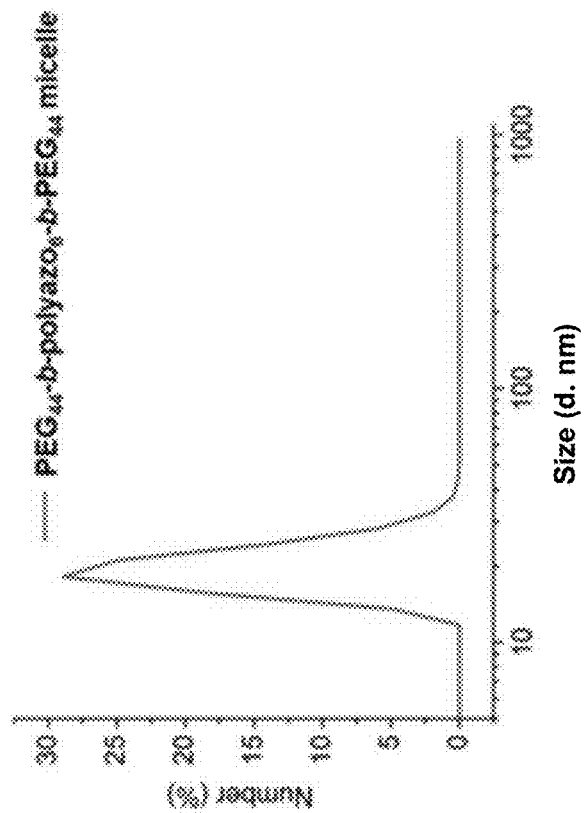
Fig. 2.3C

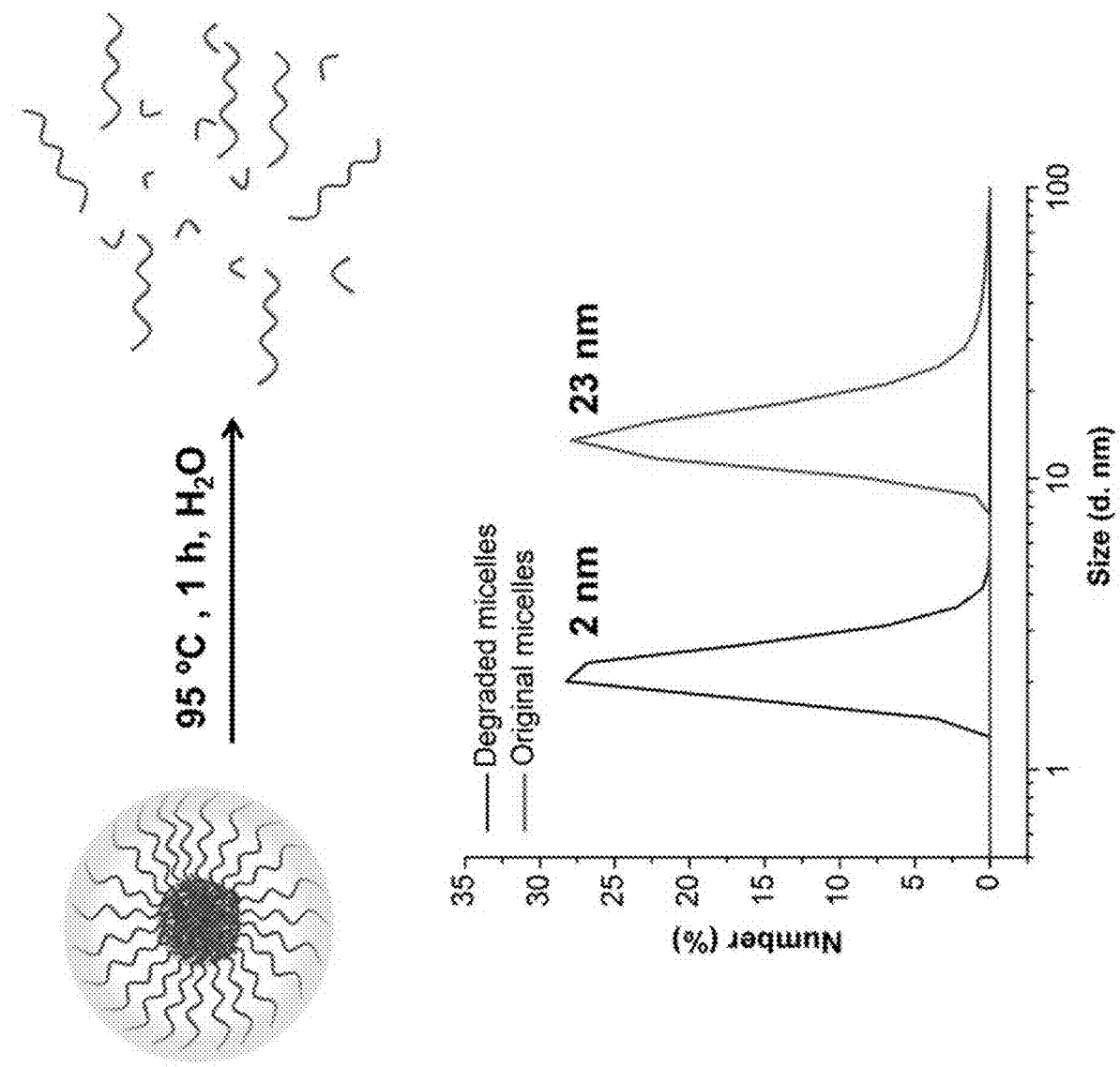
Fig. 2.4A

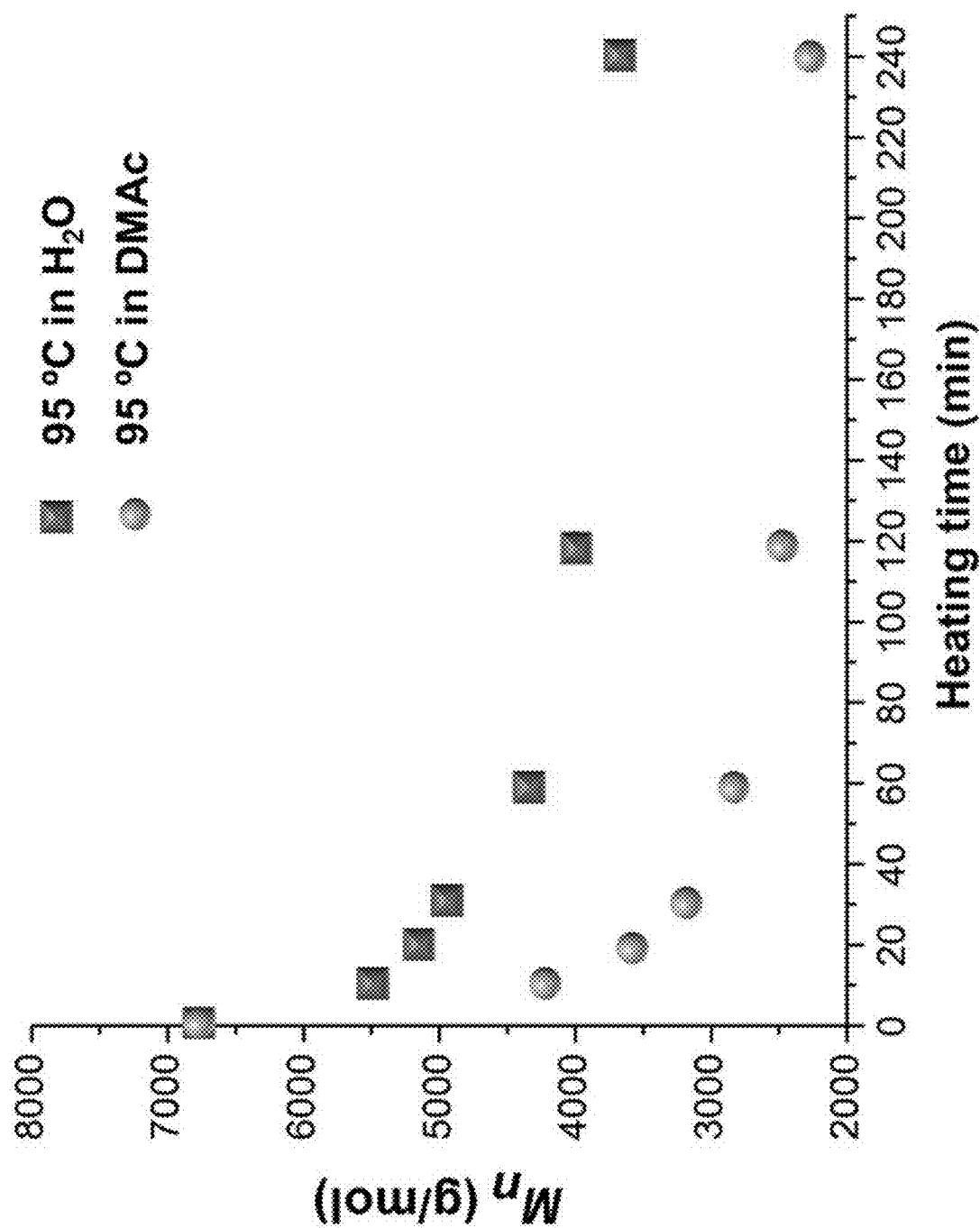
Fig. 2.4B

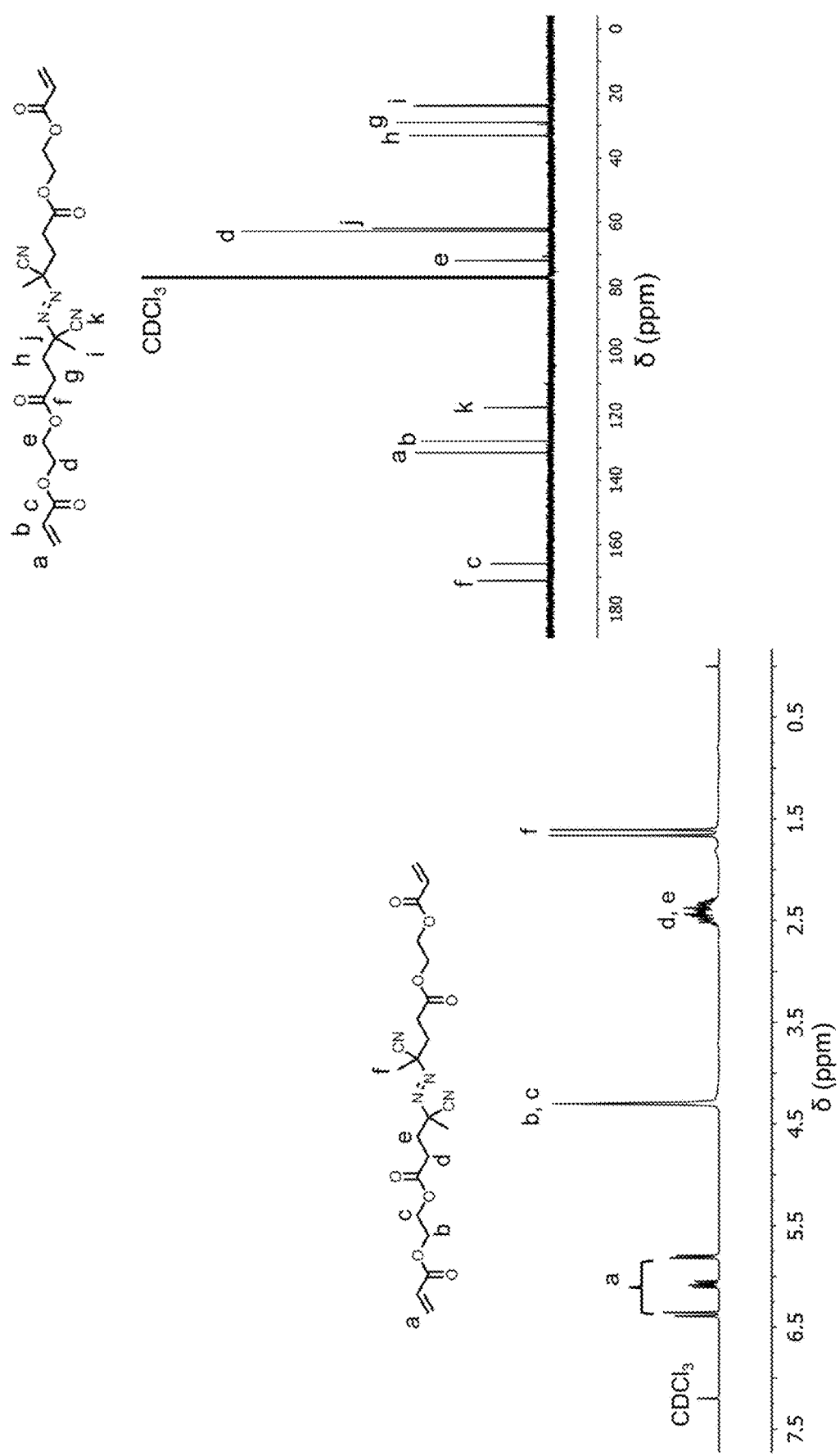
Fig. 2.5B
Fig. 2.5A

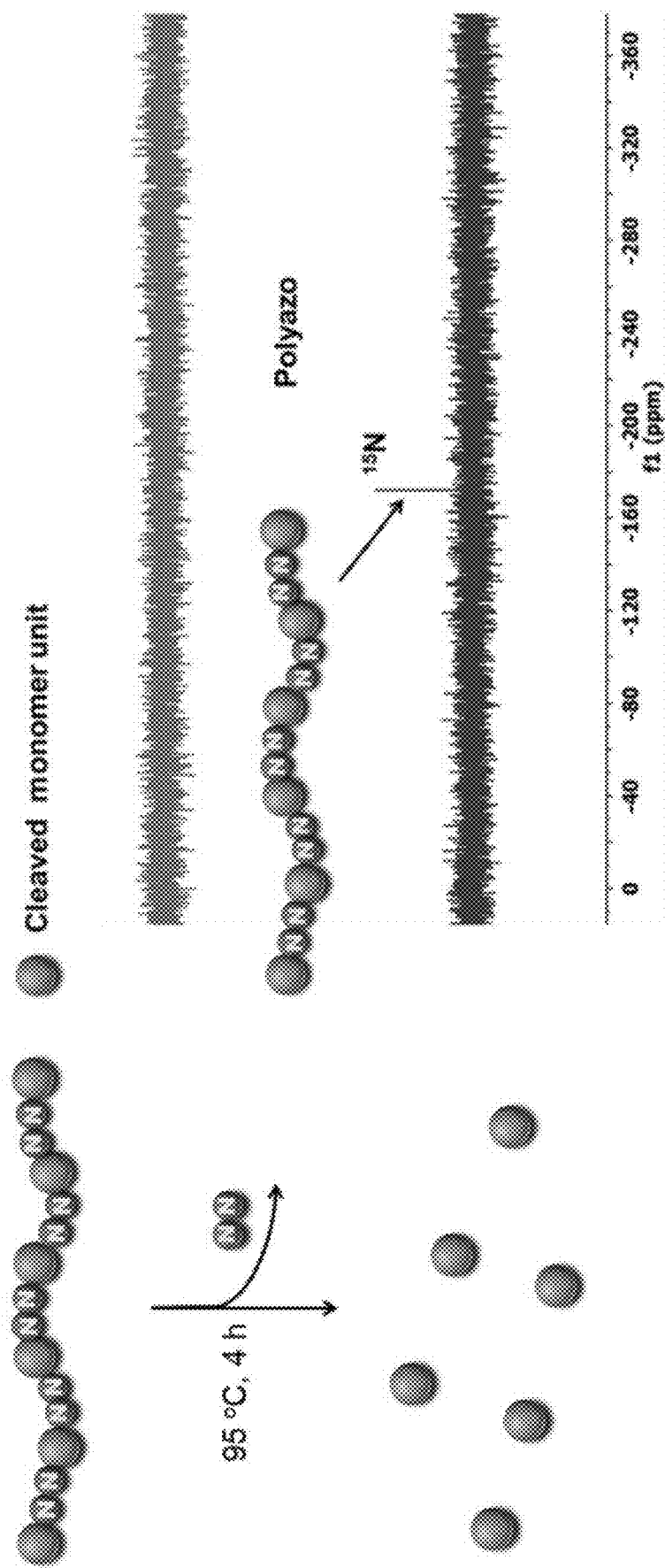
Fig. 2.6B
Fig. 2.6A

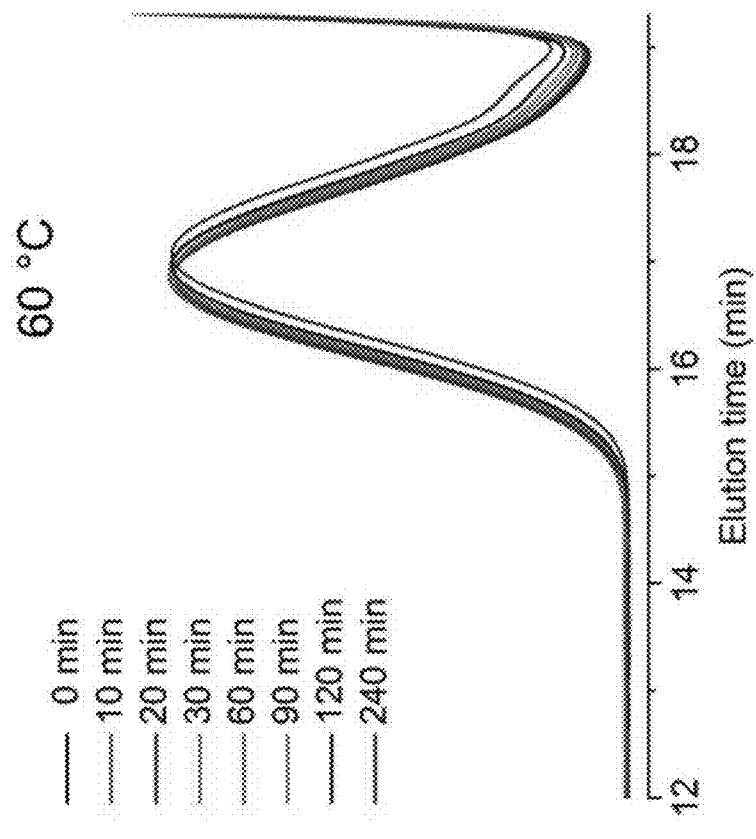
Fig. 2.7B
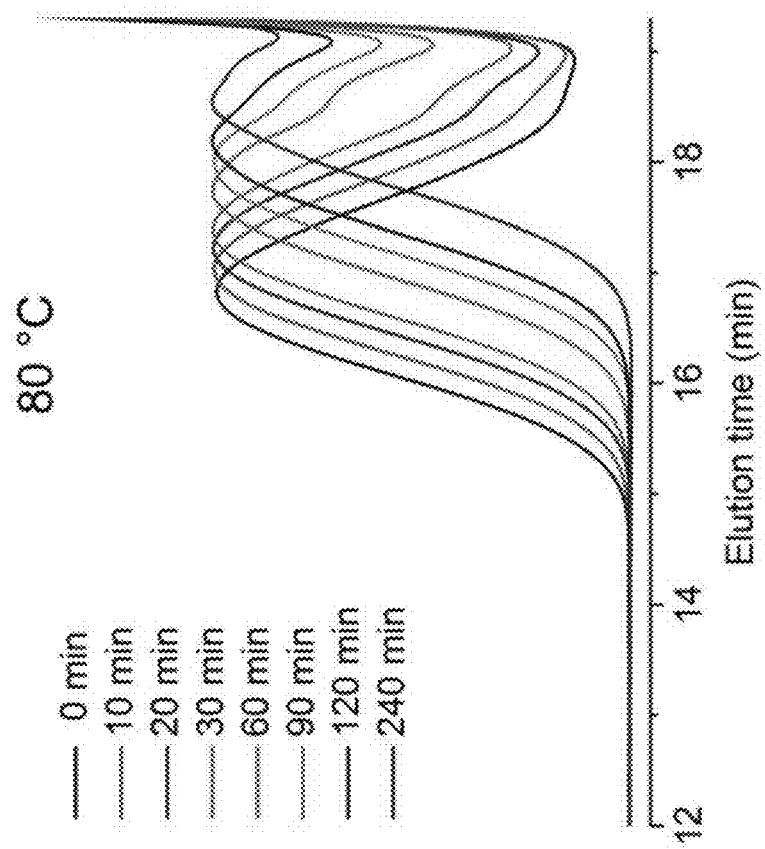
Fig. 2.7A

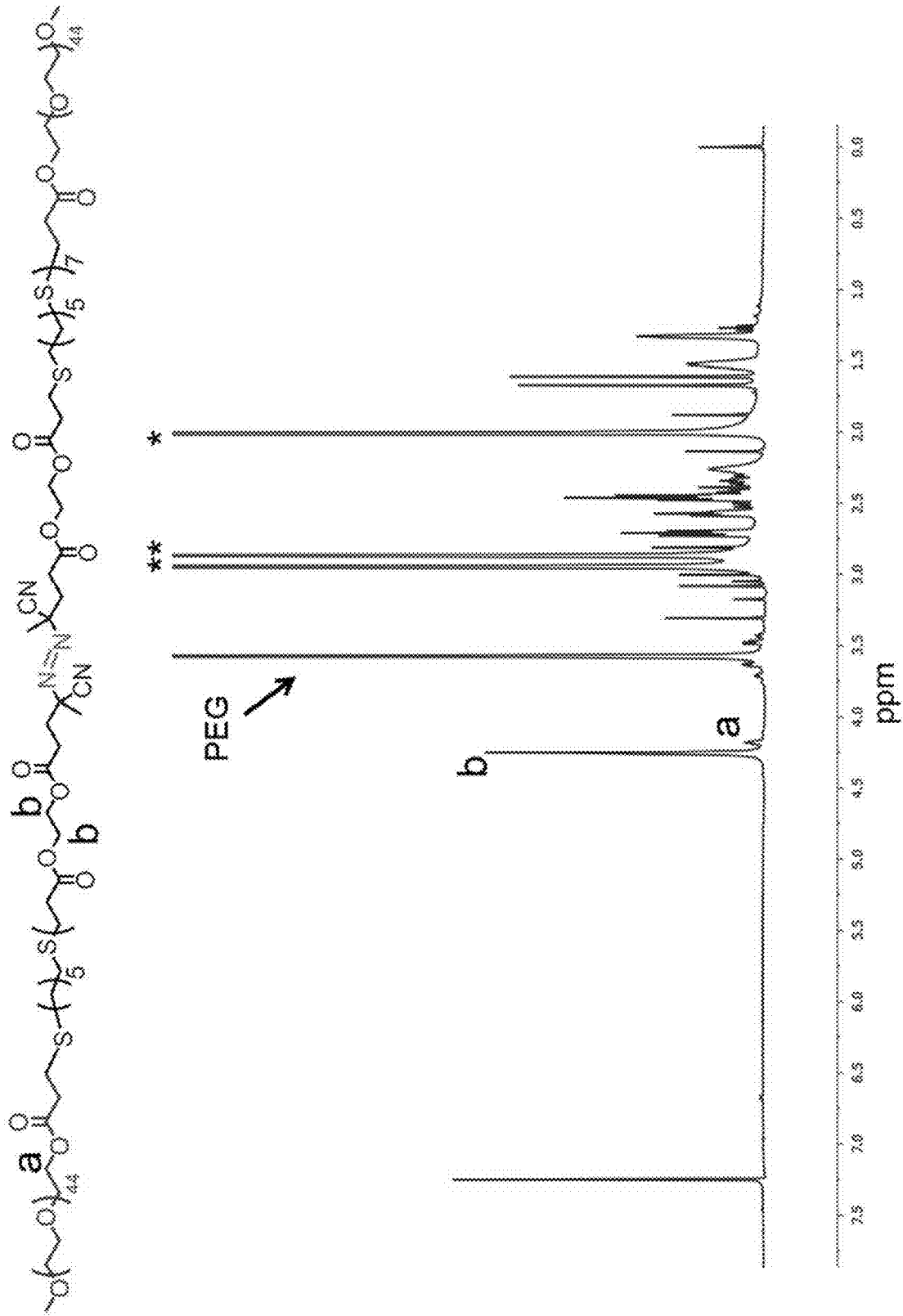
Fig. 2.8

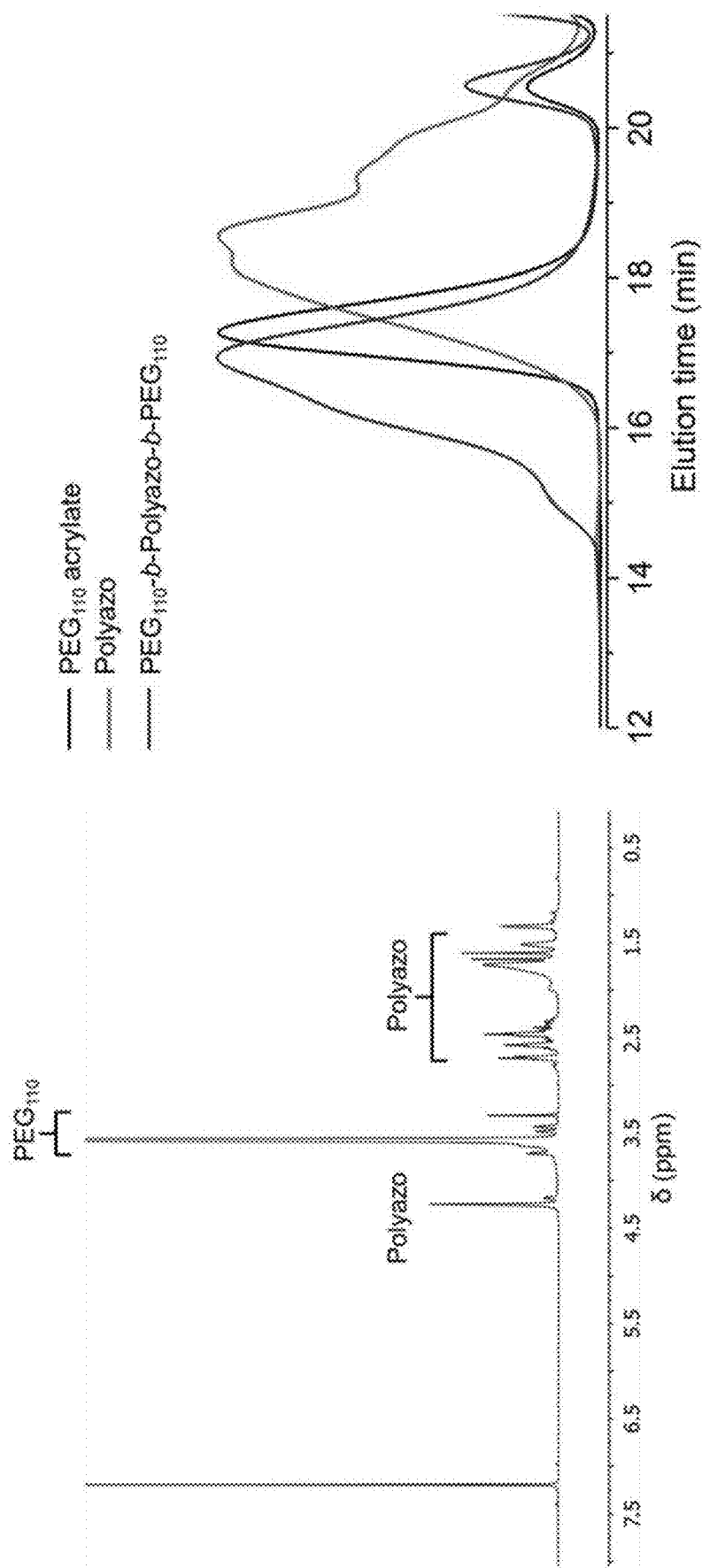
Fig. 2.9B
Fig. 2.9A

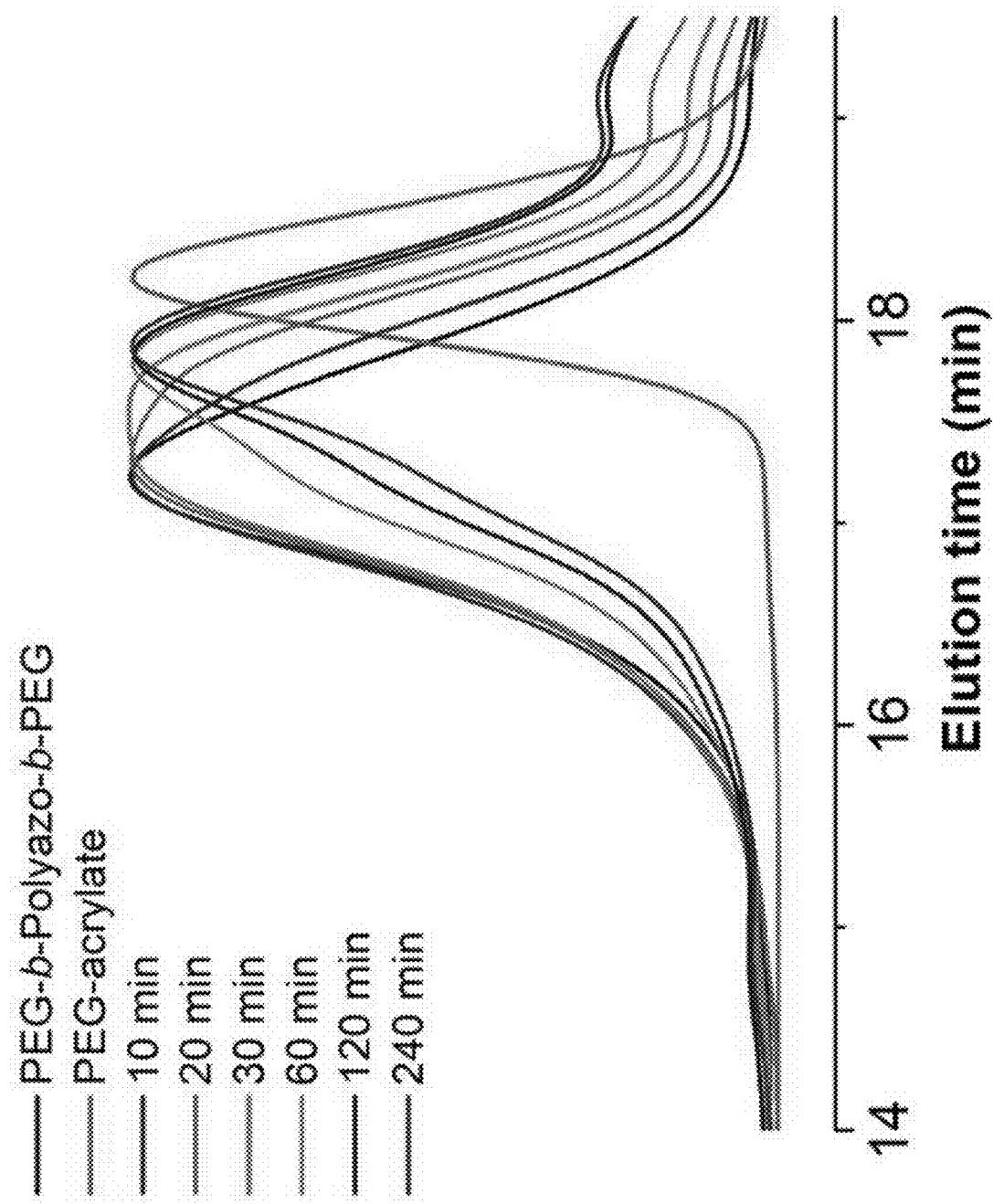
Fig. 2.10

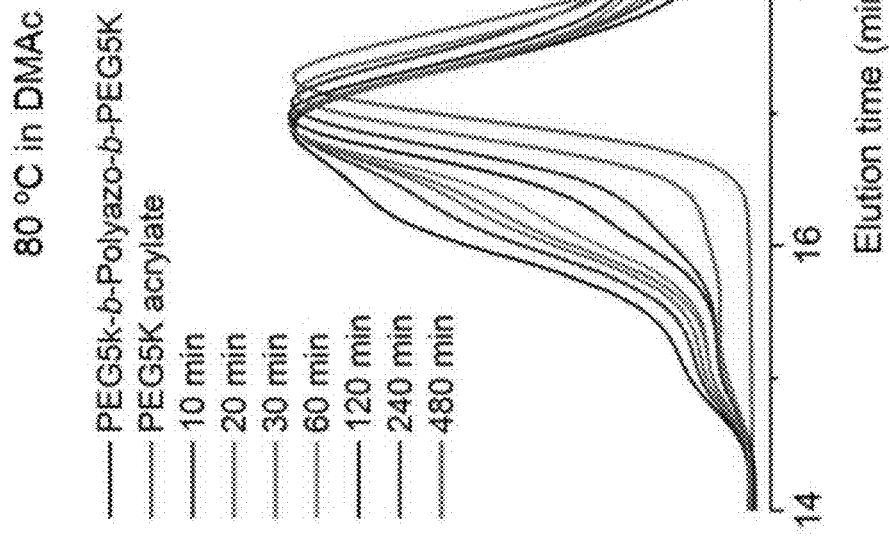
Fig. 2.11B
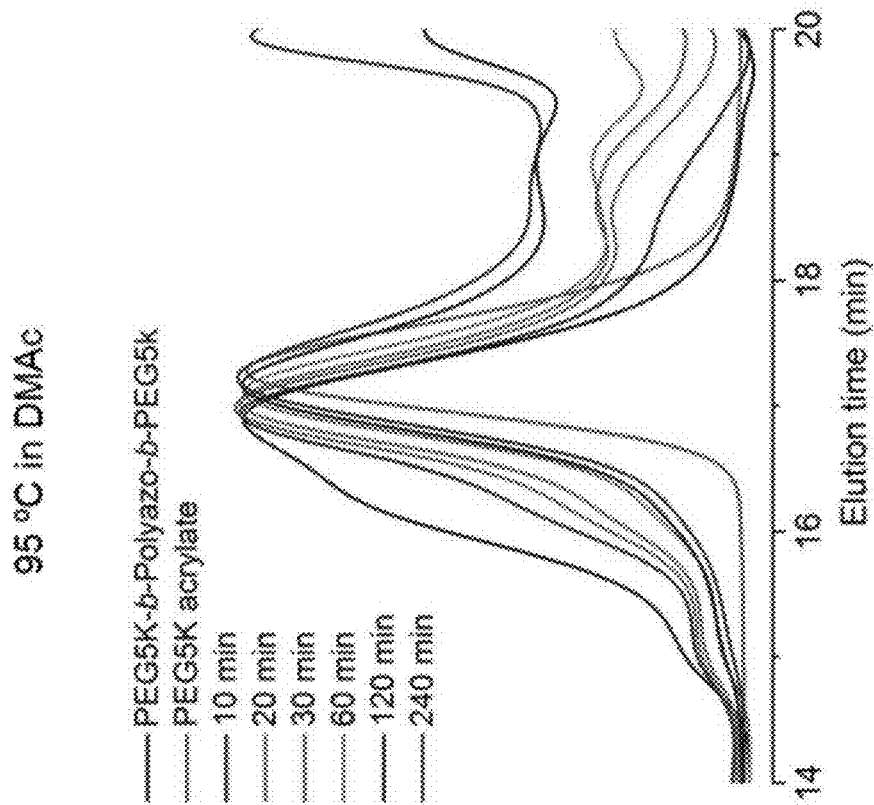
Fig. 2.11A

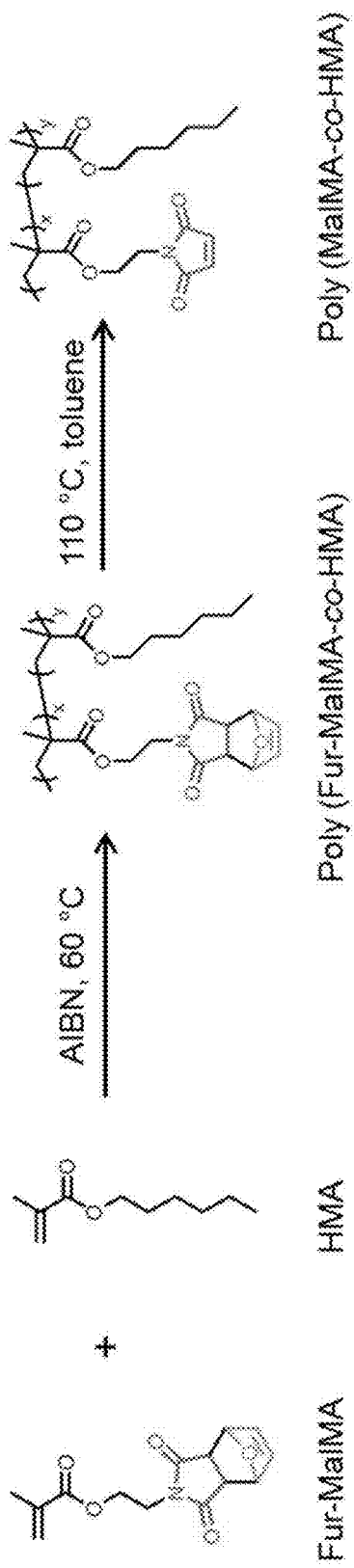
Fig. 3.1

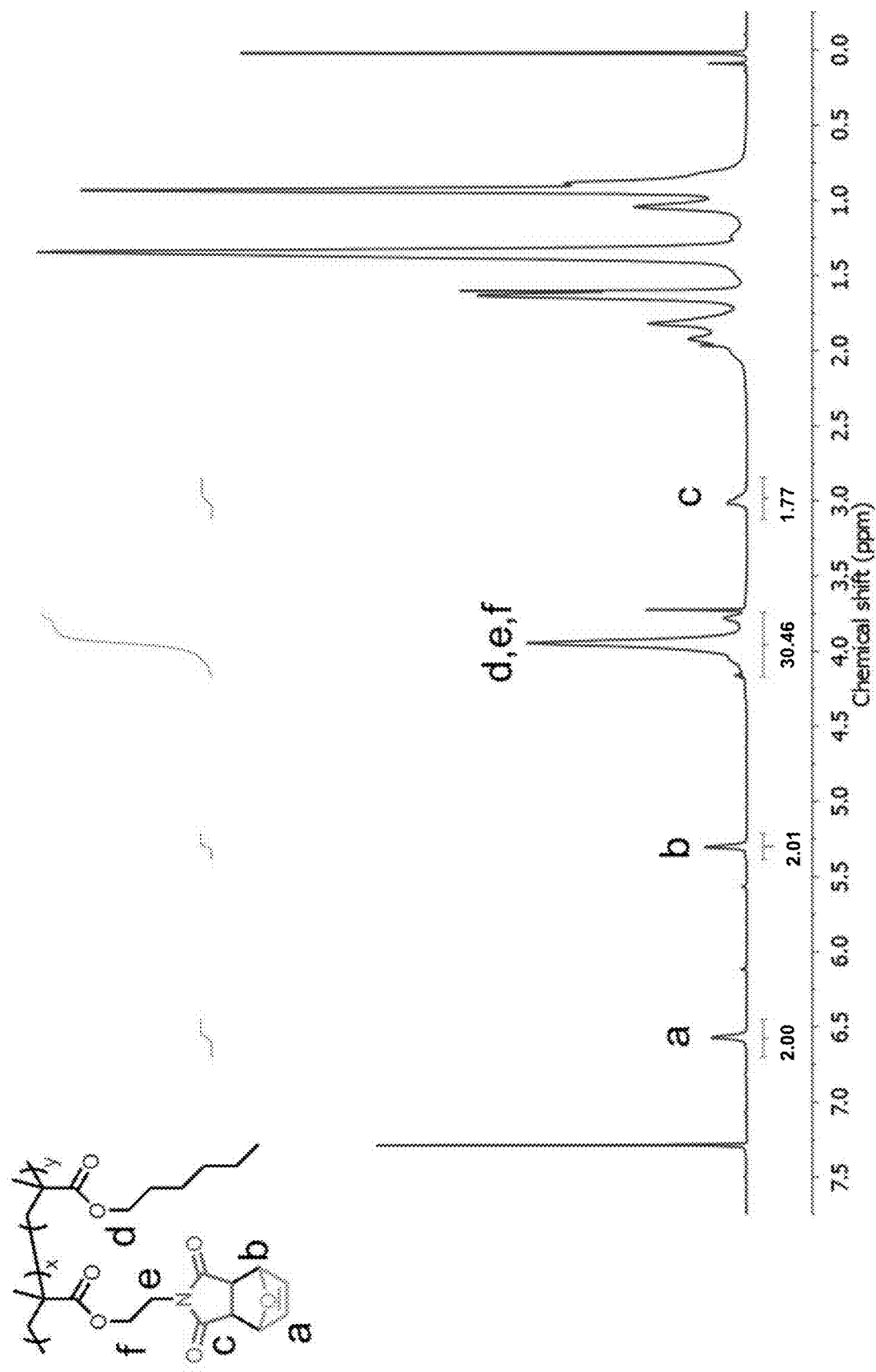
Fig. 3.2A

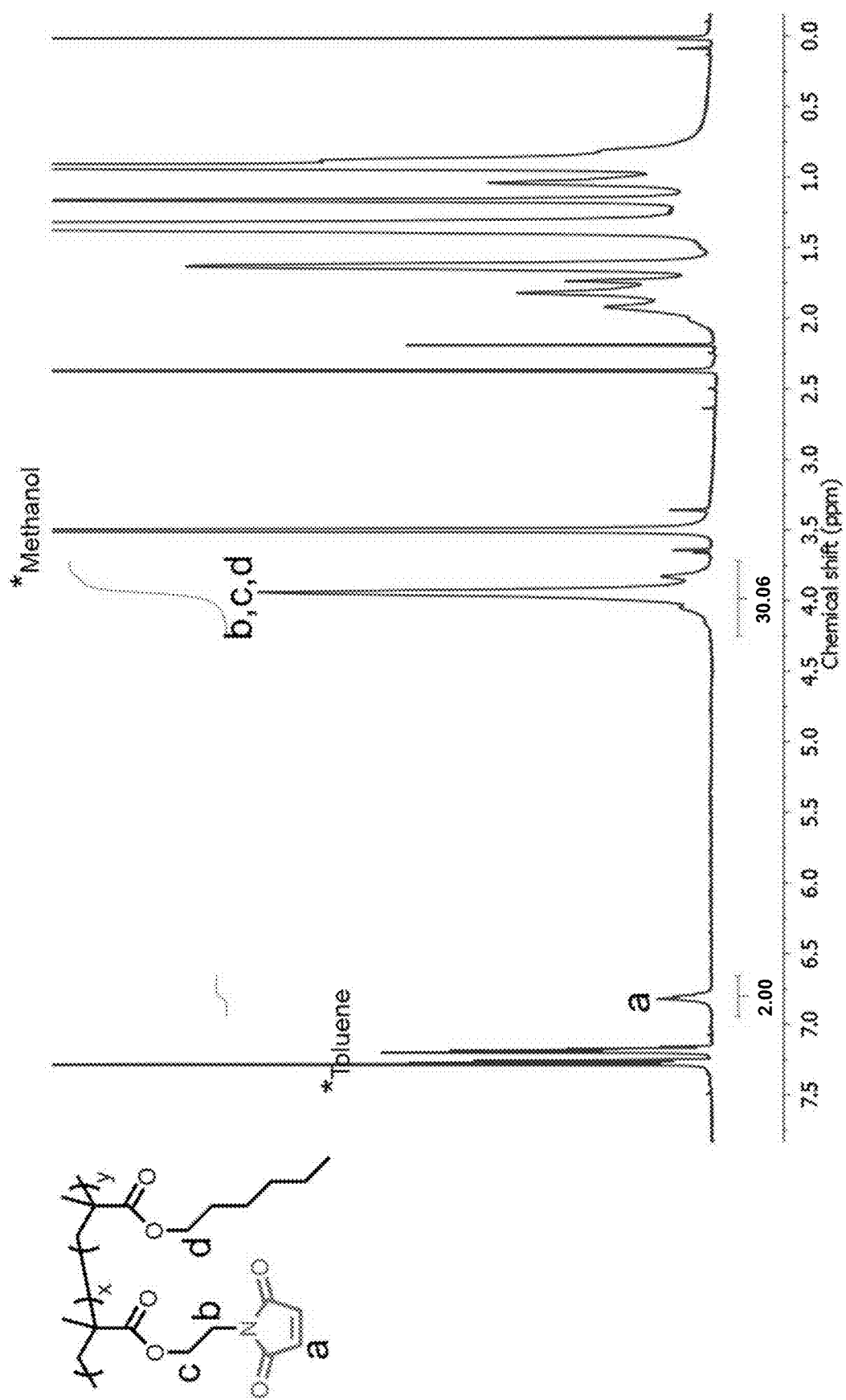
Fig. 3.2B

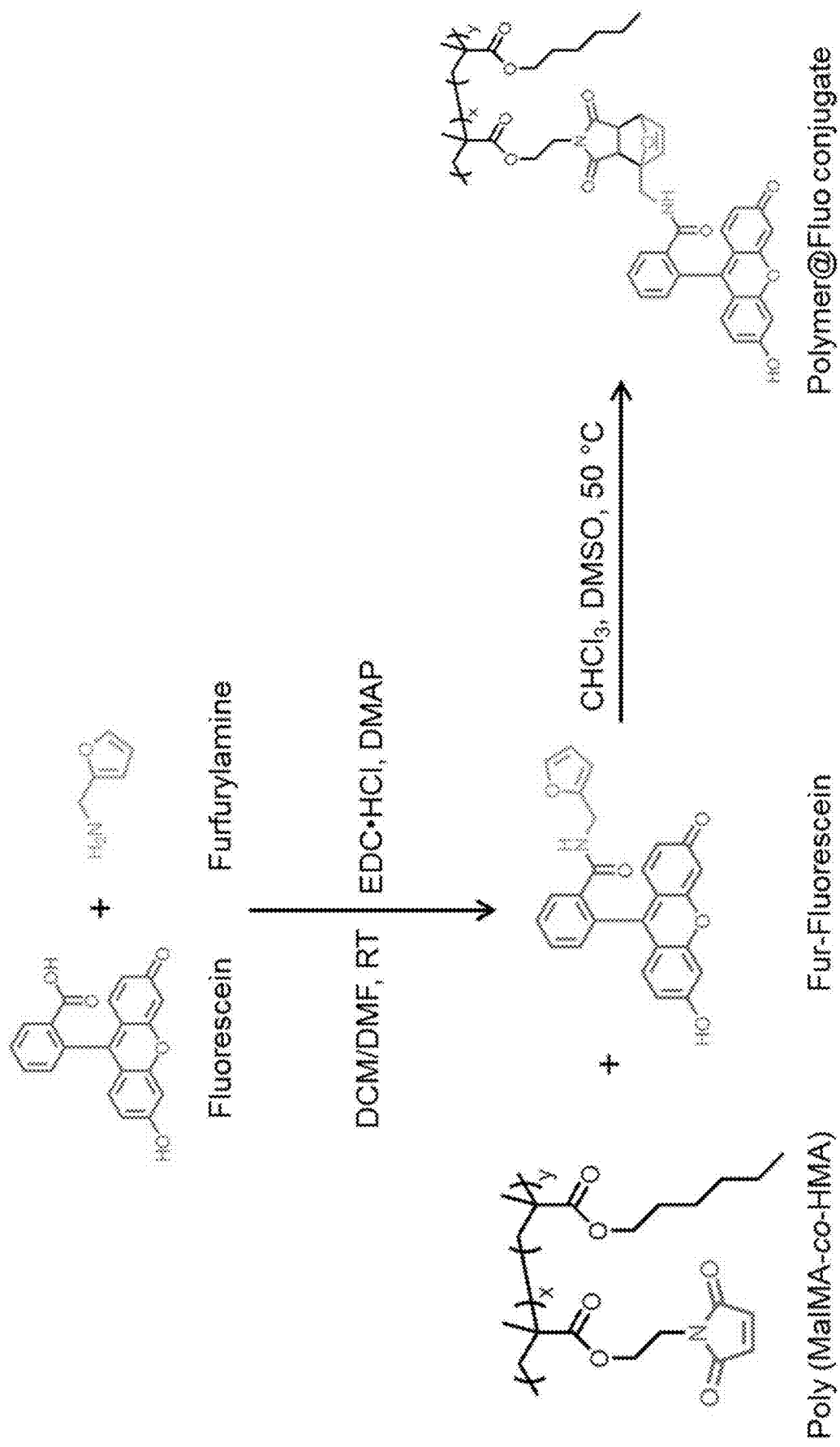
Fig. 3.3

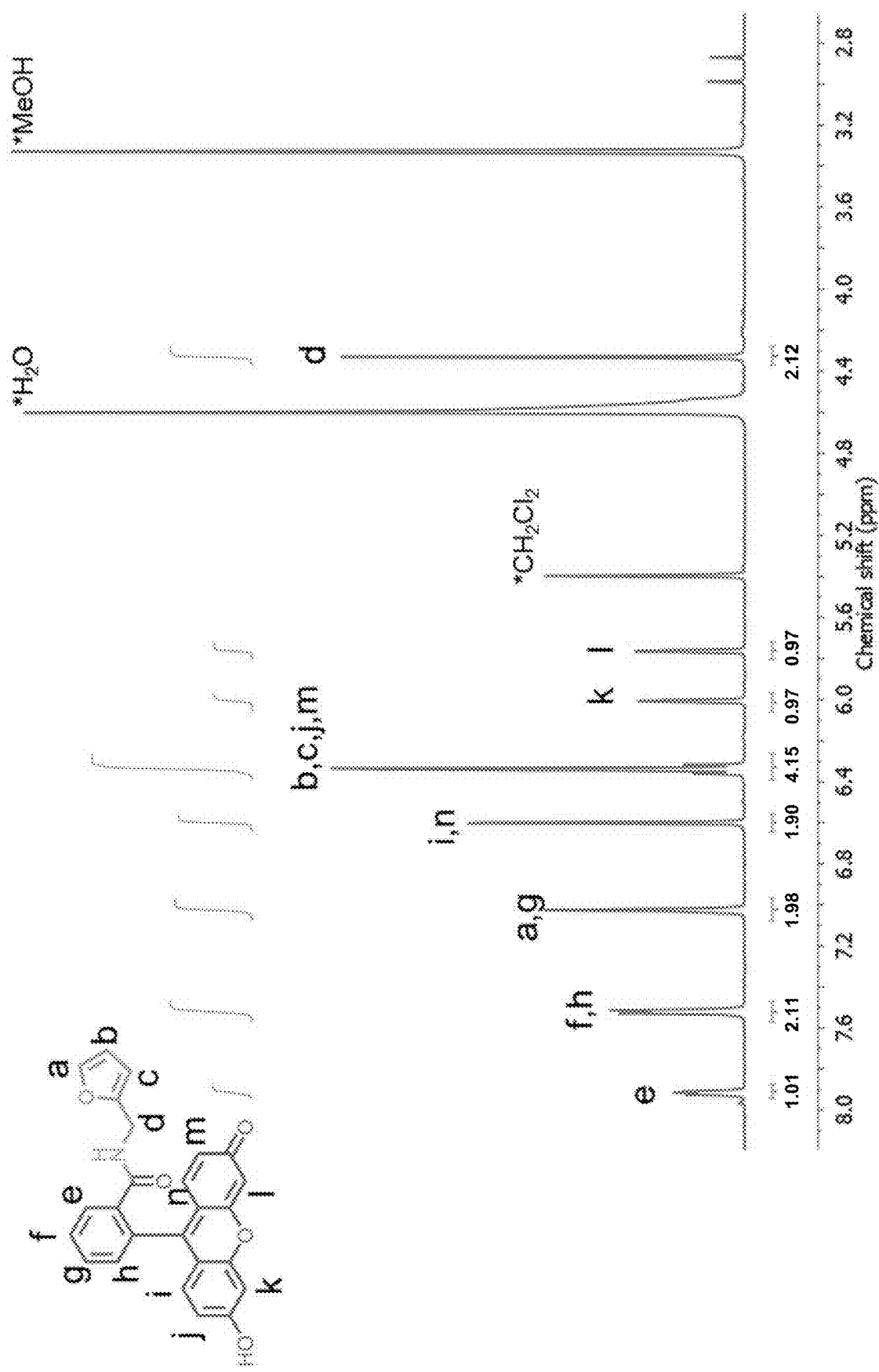
Fig. 3.4A

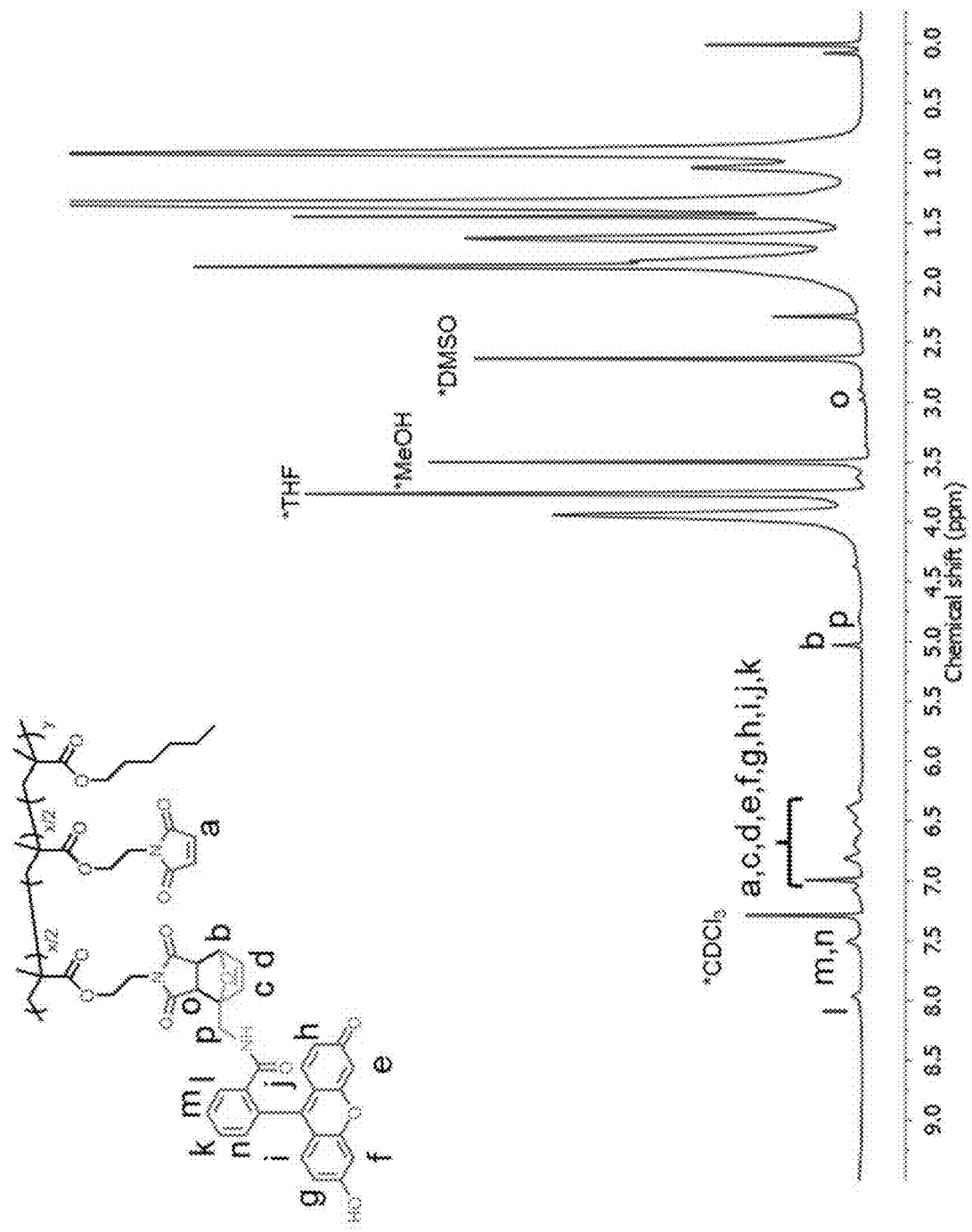
Fig. 3.4B

Fig. 3.5A
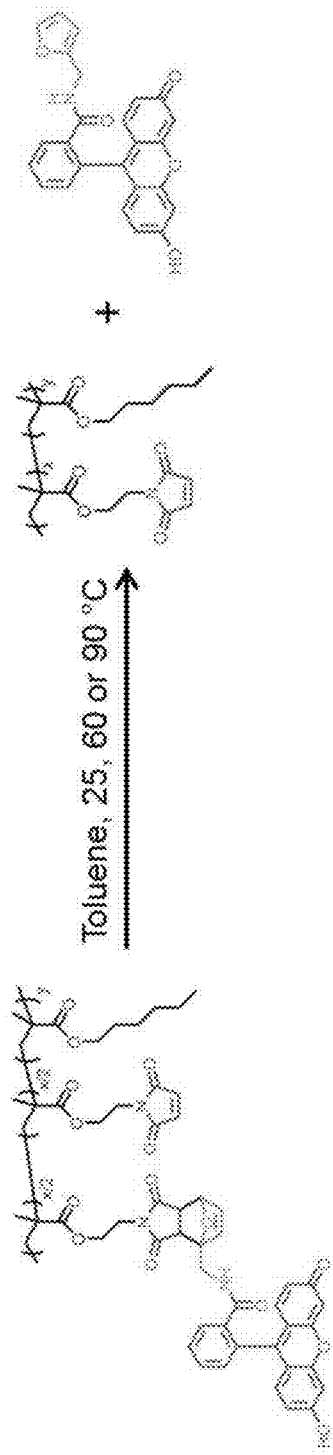
Fig. 3.5B
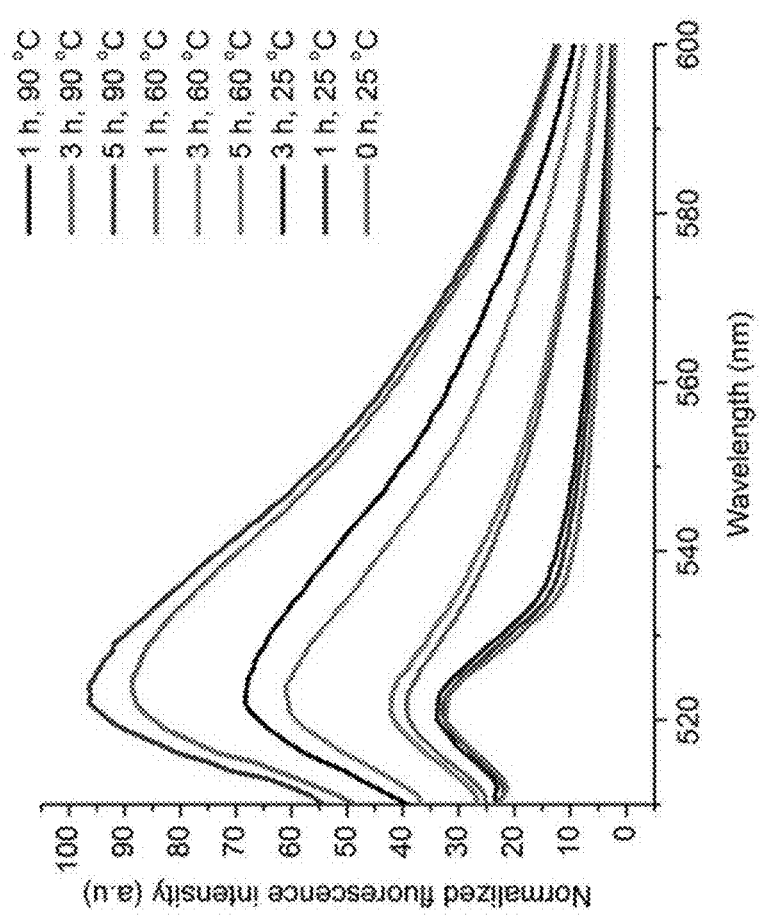

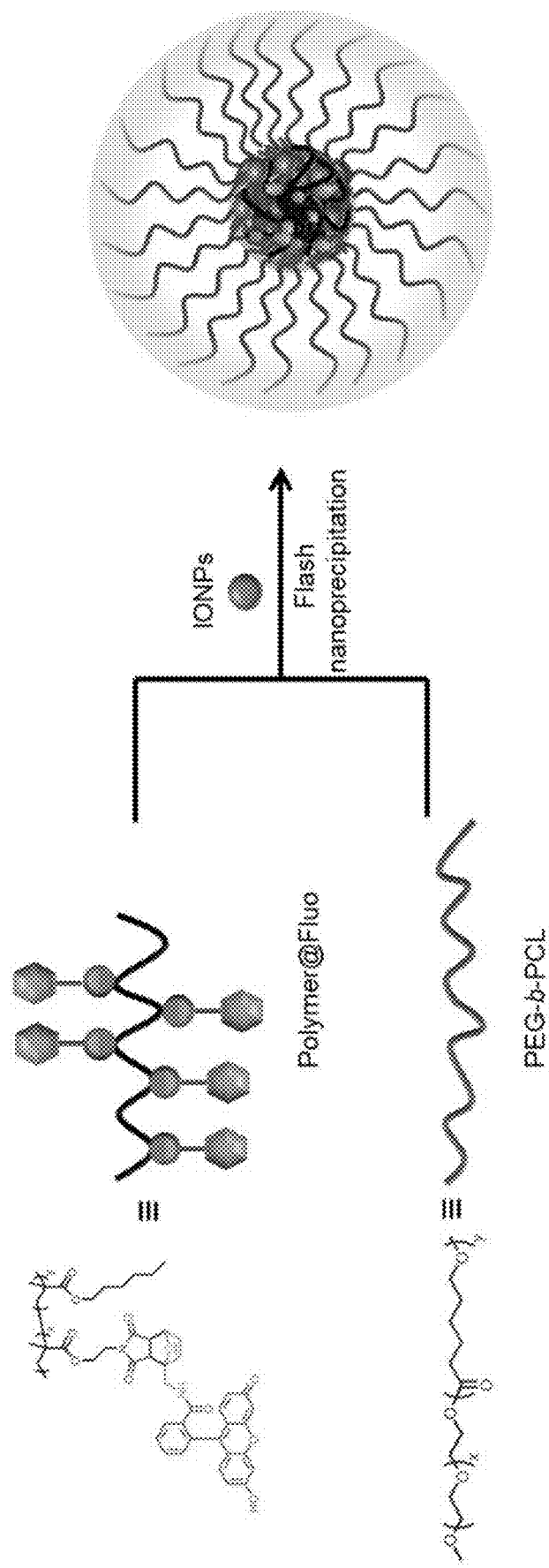
Fig. 3.6

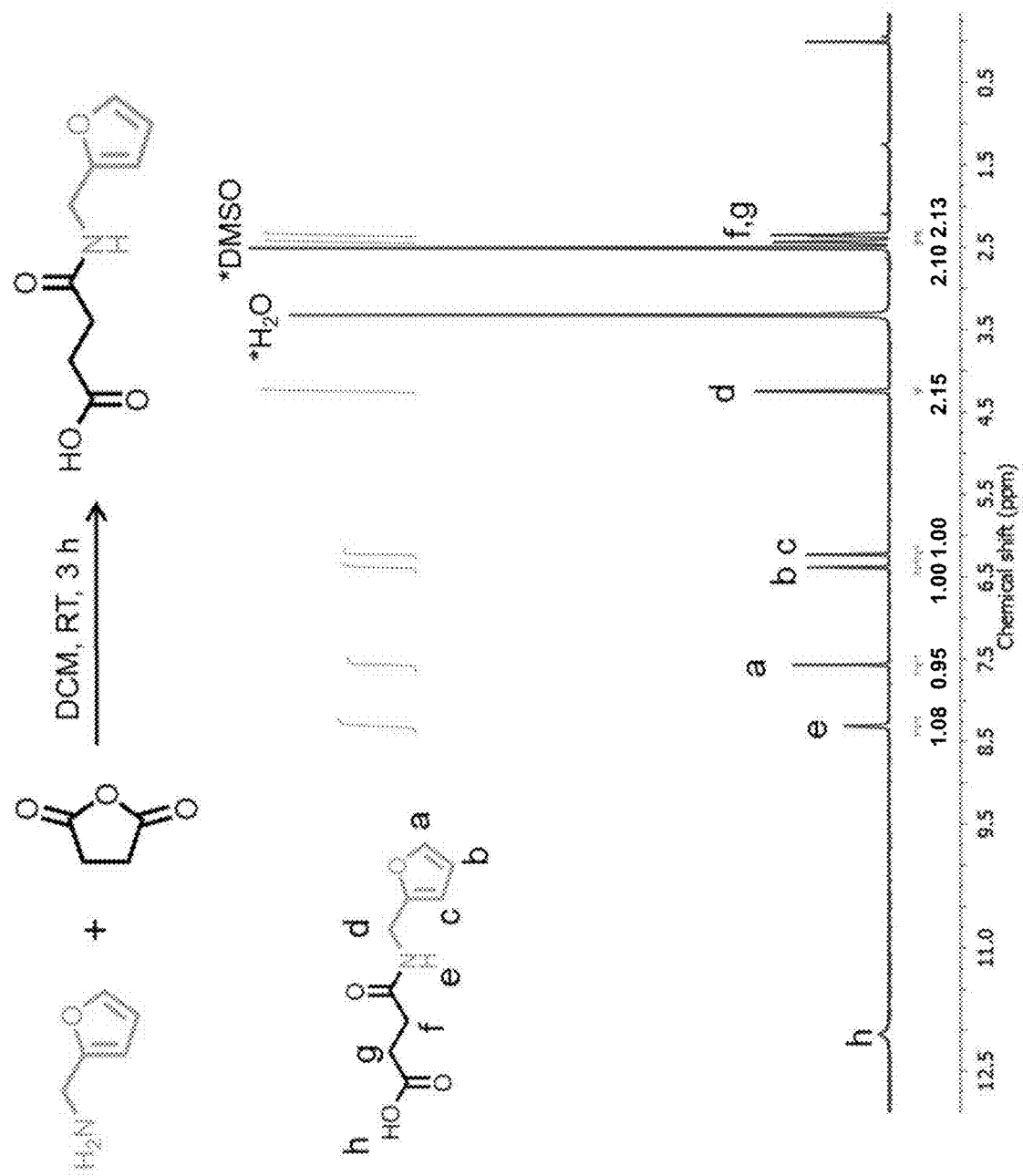
Fig. 3.7A

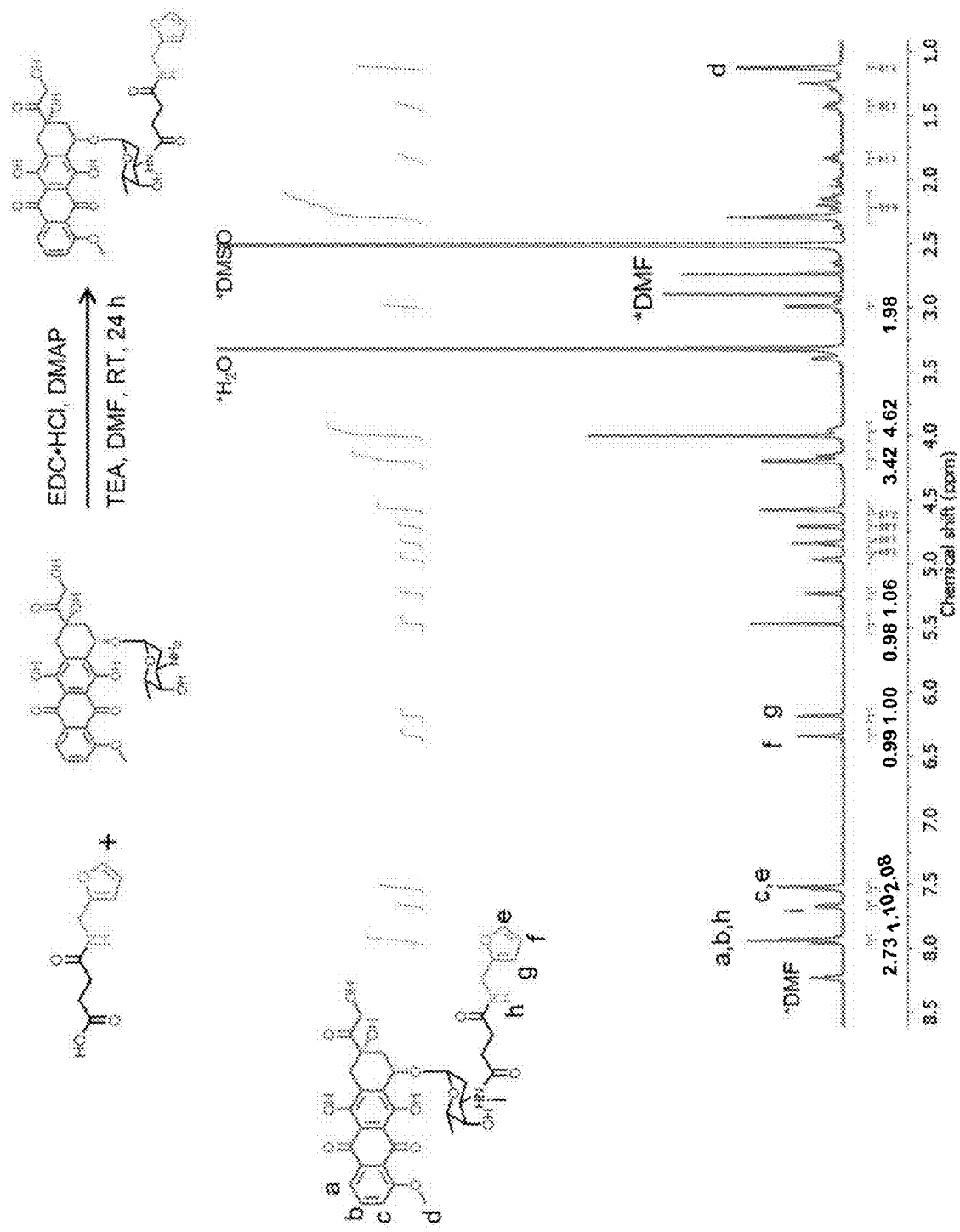
Fig. 3.7B

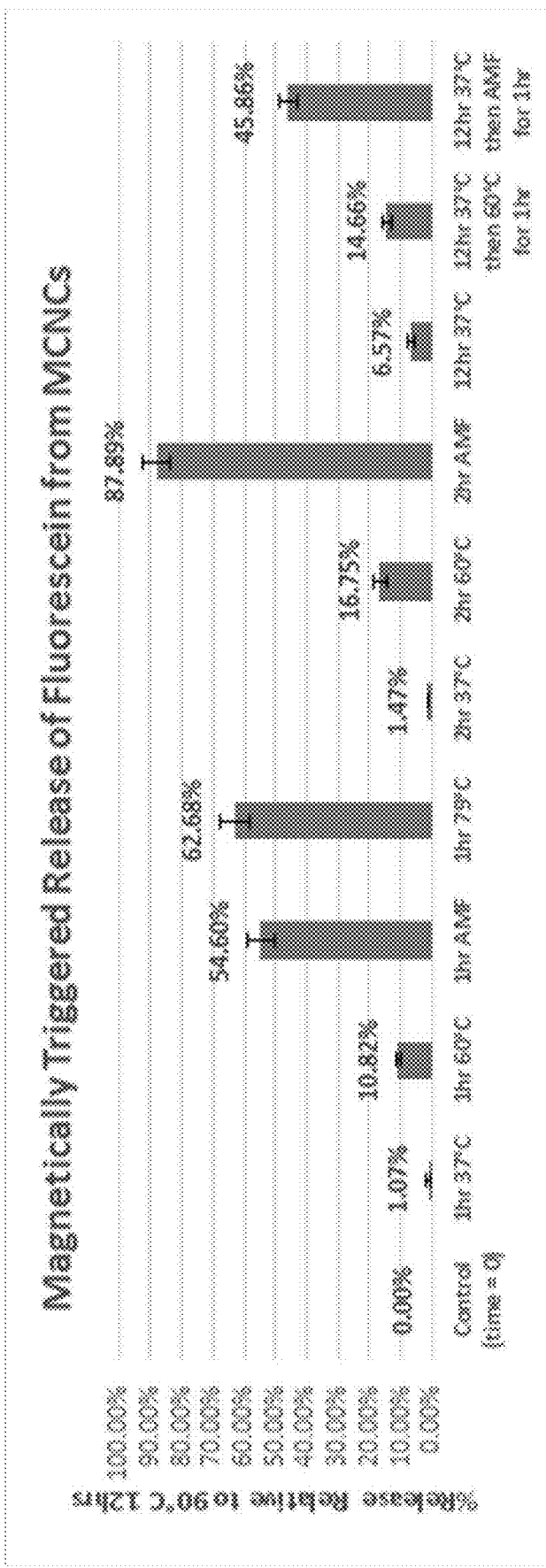
Fig. 4.1

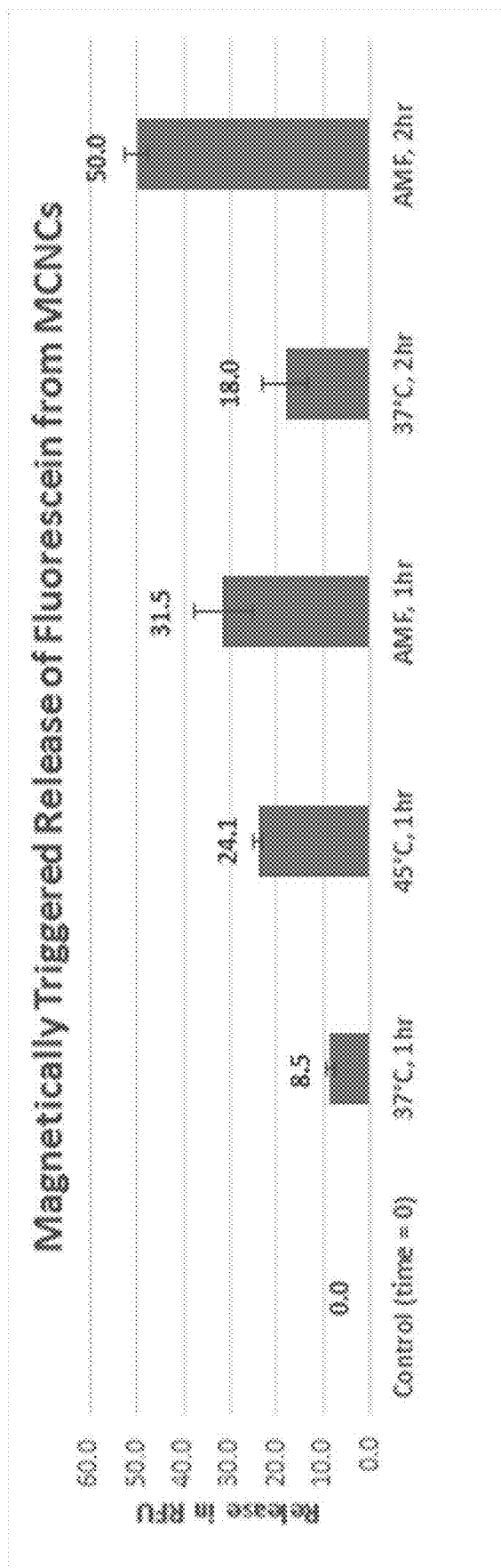
Fig. 4.2

MAGNETIC PARTICLE CONJUGATES, MICELLES, AND METHODS OF DELIVERING AGENTS

CROSS-REFERENCE TO RELATED APPLICATIONS

This application is a continuation of co-pending U.S. patent application Ser. No. 16/093,370, filed on Oct. 12, 2018, entitled "MAGNETIC PARTICLE CONJUGATES, MICELLES, AND METHODS OF DELIVERING AGENTS," the contents of which is incorporated by reference herein in its entirety.

U.S. patent application Ser. No. 16/093,370 is the 35 U.S.C. § 371 national stage application of PCT Application No. PCT/US2017/028852, filed Apr. 21, 2017, where the PCT claims the benefit of and priority to U.S. Provisional Application Ser. No. 62/328,053, having the title "MAGNETIC PARTICLE CONJUGATES, MICELLES, AND METHODS OF DELIVERING AGENTS," filed on Apr. 27, 2016, the disclosure of which is incorporated herein in by reference in their entireties.

STATEMENT REGARDING FEDERALLY SPONSORED RESEARCH OR DEVELOPMENT

This invention was made with Government support under 1345156 and 1606410 awarded by the U.S. National Science Foundation. The Government has certain rights in this invention.

BACKGROUND

Smart macromolecules are capable of substantial response in the presence of external signals, or stimuli. During the past decade, these stimuli-responsive polymers have witnessed significant successes in a diverse range of applications, such as triggered drug/gene release, diagnosis, tissue engineering, coatings and textiles.

SUMMARY

Embodiments of the present disclosure provide for magnetic particle conjugates, methods of making the magnetic particle conjugates, methods of using magnetic particle conjugates, micelles (also referred to as a "magnetic composite nanocarrier" (MCNC)), methods of making micelles, methods of using micelles, and the like.

Embodiments of the present disclosure provide for a composition, among others, that includes: a magnetic particle conjugate having a magnetic particle and a polymer attached to the magnetic particle, wherein the polymer includes an agent ($A_{gent}$) bonded to the polymer through thermally degradable group Q, wherein the polymer is represented by the following:

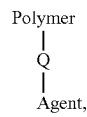

where the polymer has one or more Q-Agent groups.

Embodiments of the present disclosure provide for a composition, among others, that includes: a micelle including a plurality of magnetic particles, a plurality of amphiphilic polymers, and a plurality of agents, wherein the amphiphilic polymer has a hydrophobic region and a hydrophilic region, wherein the hydrophobic region of the amphiphilic polymer is located in a central region of the micelle and the hydrophilic region is located away from the central region and forms the micelle outer boundary, wherein a portion of magnetic particles and a portion of the agents are located in the central region of the micelle, and wherein the amphiphilic polymer contains thermally labile backbone bonds.

Embodiments of the present disclosure provide for a composition, among others, that includes: a micelle having a hydrophobic core including a plurality of particles, a plurality of polymers, and a plurality of agents, wherein the polymer optionally contains thermally labile backbone bonds.

Embodiments of the present disclosure provide for a method of delivering an agent, among others, that includes: administering a composition of any one of the claims to a subject; and exposing an area of the subject to an alternating magnetic field, wherein the alternating magnetic field causes the magnetic particles to generate thermal energy, wherein the thermal energy causes the agent to be released from the composition.

Embodiments of the present disclosure provide for a method of delivering an agent, among others, that includes: administering a composition as disclosed herein to a subject; and causing the release of the agent from the composition via exposure of the composition to thermal energy.

Other compositions, methods, features, and advantages will be or become apparent to one with skill in the art upon examination of the following drawings and detailed description. It is intended that all such additional compositions, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1.1 illustrates synthesis of poly(Fur-MalMA-co-HPMA)-b-PHPMA via sequential RAFT polymerizations.

FIG. 1.2 presents ¹HNMR spectra of poly(Fur-MalMA-co-HPMA) (bottom) and poly(Fur-MalMA-co-HPMA)-b-PHPMA (up).

FIG. 1.3 illustrates GPC traces of poly(Fur-MalMA-co-HPMA) and poly(Fur-MalMA-co-HPMA)-b-PHPMA.

FIG. 1.4A is TEM image of poly(Fur-MalMA-co-HPMA) in water; FIG. 1.4B shows DLS of poly(Fur-MalMA-co-HPMA) and poly(Fur-MalMA-co-HPMA)-b-PHPMA in water.

FIG. 1.5 shows deprotection of furan-Maleimide functional poly(Fur-MalMA-co-HPMA); ¹HNMR spectra of poly(Fur-MalMA-co-HPMA) (bottom) and poly(MalMA-co-HPMA) (up).

FIG. 1.6 illustrates a synthetic route to polymer-MNPs conjugates bearing free maleimide functionalities.

FIG. 1.7A provides FTIR spectra of APS-MNPs, poly(Fur-MalMA-co-HPMA)-b-PHPMA (polymer), polymer-MNPs before deprotection, and polymer-MNPs after deprotection; FIG. 1.7B illustrates a stability test of APS-MNPs and polymer-MNPs in buffer (pH=9).

FIG. 1.8 illustrates the fluorescein attachment to polymer-MNPs conjugate via forward Diels-Alder reaction.

FIG. 1.9A shows a general scheme of releasing Fur-Fluo via AMF-induced rDA reaction; FIG. 1.9B illustrates release of Fur-Fluo under various conditions, i.e., 23° C., 80° C., and AMF.

FIG. 2.1A shows $^1$H NMR spectra of dithiol functional polyazo$_{10}$ (top blue line), HDT (middle green line) and ACVADA (bottom red line). Disappearance of signals attributed to acrylate (blue dashed line box, 5.8-6.5 ppm) indicated ACVADA monomer was completely consumed; FIG. 2.1B $^1$H NMR spectrum of hydroxyl functionalized polyazo$_{10}$ end capped with 2-hydroxyethylacrylate.

FIG. 2.2A shows GPC traces of samples taken during thermal degradation of polyazo$_{10}$ at 95° C. without HQ; FIG. 2.2B shows GPC traces of samples taken during thermal degradation of polyazo$_{10}$ at 95° C. in the presence of HQ; FIG. 2.2C illustrates the decrease in $M_n$ determined by GPC in the absence and presence of HQ; FIG. 2.2D illustrates the decrease in $M_n$ determined by GPC at three different temperatures in the presence of HQ (60, 80 and 95° C.).

FIG. 2.3A shows GPC traces of polyazo6, PEG$_{44}$ acrylate and PEG$_{44}$-b-polyazo$_6$-b-PEG$_{44}$; FIG. 2.3B shows DOSY NMR spectra of PEG$_{44}$-b-polyazo$_6$-b-PEG$_{44}$ (dark blue line) and PEG$_{44}$ acrylate (red line); FIG. 2.3C shows DLS size distribution of PEG$_{44}$-b-polyazo$_6$-b-PEG$_{44}$ triblock copolymer-based micelles in water; FIG. 2.3D shows TEM image of triblock copolymer-based micelles cast from aqueous solution.

FIG. 2.4A shows DLS size distribution of PEG$_{44}$-b-polyazo$_6$-b-PEG$_{44}$ based micelles before and after thermal treatment at 95° C.; FIG. 2.4B illustrates the decrease in $M_n$ determined by GPC of PEG$_{44}$-b-polyazo$_6$-b-PEG$_{44}$ heated in water or DMAc.

FIGS. 2.5A-2.5B provide $^1$H NMR and $^{13}$C NMR spectra of ACVADA monomer.

FIG. 2.6A provides demonstration of thermal degradation of polyazo and resulting emission of N$_2$; FIG. 2.6B provides $^1$N NMR spectrum of polyazo before and after thermal treatment at 95° C. in the presence of hydroquinone.

FIG. 2.7A shows GPC traces of samples taken during thermal degradation of polyazo at 80° C. in the presence of HQ; FIG. 2.7B shows GPC traces of samples taken during thermal degradation of polyazo at 60° C. in the presence of HQ.

FIG. 2.8 shows the $^1$H NMR spectrum of sample taken during the conjugation of PEG44 to polyazo after 12 h.

FIG. 2.9A shows the $^1$H NMR spectrum of PEG$_{110}$-b-polyazo-b-PEG$_{110}$; FIG. 2.9B shows the GPC traces of PEG$_{110}$ acrylate, Polyazo and PEG$_{110}$-b-polyazo-b-PEG$_{110}$.

FIG. 2.10 shows GPC traces of samples taken during the thermal degradation of PEG$_{44}$-b-polyazo-b-PEG$_{44}$ at 95° C. in water.

FIG. 2.11A shows GPC traces of samples taken during the thermal degradation of PEG$_{110}$-b-polyazo-b-PEG$_{110}$ at 95° C. in the absence of HQ; FIG. 2.11B shows GPC traces of samples taken during the thermal degradation of PEG$_{110}$-b-polyazo-b-PEG$_{110}$ at 80° C. in the absence of HQ.

FIG. 3.1 illustrates synthesis of poly (MalMA-co-HMA) via free radical copolymerization, Scheme 3.1.

FIG. 3.2A shows the $^1$H NMR spectrum of poly(Fur-MalMA-co-HMMA) in CDCl$_3$.

FIG. 3.2B shows the $^1$H NMR spectrum of poly(MalMA-co-HMMA) in CDCl$_3$.

FIG. 3.3 illustrates synthesis of polymer@Fluo conjugate via Diels-Alder reaction, Scheme 3.2.

FIG. 3.4A shows the $^1$H NMR spectrum of Fur-Fluo in CD$_2$Cl$_2$ (50%) and MeOD (50%).

FIG. 3.4B shows the $^1$H NMR spectrum of polymer@Fluo in CDCl$_3$.

FIG. 3.5A shows the retro-Diels-Alder reaction of polymer@Fluo at various temperatures in toluene; FIG. 3.5B shows the fluorescence spectra of "free" Fur-Fluo at various reaction time and reaction temperatures. Released Fur-Fluo was collected by dissolving product into methanol following removing toluene.

FIG. 3.6 illustrates a preparation of MCNCs via flash nanoprecipitation, Scheme 3.3.

FIG. 3.7A shows the $^1$H NMR spectrum of Fur-COOH in DMSO-d$_6$.

FIG. 3.7B shows the $^1$H NMR spectrum of Fur-DOX in DMSO-d$_6$.

FIG. 4.1 shows the results of a fluorescein release test at AMF peak temperature 79° C.

FIG. 4.2 shows the results of a fluorescein release test at AMF peak temperature 46° C.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of biochemistry, microbiology, molecular biology, pharmacology, medicine, and the like, which are within the skill of the art. Such techniques are explained fully in the literature.

Prior to describing the various embodiments, the following definitions are provided and should be used unless otherwise indicated.

Unless otherwise defined, all technical and scientific terms used herein have the same meaning as commonly understood by one of ordinary skill in the art of microbiology, molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

By "administration" is meant introducing a magnetic particle conjugate of the present disclosure into a subject. The route of administration can include any route of administration, such as intravenous, oral, topical, subcutaneous, peritoneal, intraarterial, inhalation, vaginal, rectal, nasal, introduction into the cerebrospinal fluid, or instillation into body compartments can be used.

The terms "therapeutically effective amount" and "an effective amount" are used interchangeably herein and refer to that amount of the composition (e.g., magnetic particle conjugate) being administered that is sufficient to affect the intended result. For example, an effective amount of the magnetic particle conjugate can activate cell signaling upon application of a magnetic field. The therapeutically effective amount may vary depending upon the intended application (in vitro or in vivo), or the subject, e.g., the weight and age of the subject, the manner of administration and the like, which can readily be determined by one of ordinary skill in the art. The specific dose will vary depending on the particular agent chosen, the dosing regimen to be followed, whether it is administered in combination with other agents, timing of administration, and the physical delivery system in which it is carried.

The term "unit dosage form," as used herein, refers to physically discrete units suitable as unitary dosages for human and/or animal subjects, each unit containing a predetermined quantity of the composition (e.g., magnetic particle conjugate) calculated in an amount sufficient to produce the desired effect in association with a pharmaceutically acceptable diluent, carrier or vehicle. The specifications for unit dosage forms depend on the particular magnetic particle conjugate employed, the route and frequency of administration, and the effect to be achieved, and the pharmacodynamics associated with each magnetic particle conjugate in the subject.

As used herein, a "pharmaceutical composition" and a "pharmaceutical formulation" are meant to encompass embodiments of the present disclosure suitable for administration to a subject, such as a mammal, especially a human. In general, a "pharmaceutical composition" or "pharmaceutical formulation" is sterile, and preferably free of contaminants that are capable of eliciting an undesirable response within the subject (e.g., the magnetic particle conjugate in the pharmaceutical composition is pharmaceutical grade). Pharmaceutical compositions can be designed for administration to subjects or patients in need thereof via a number of different routes of administration including oral, intravenous, intraarterial, buccal, rectal, parenteral, intraperitoneal, intradermal, intracheal, intramuscular, subcutaneous, inhalational and the like.

As used herein, the terms "treatment", "treating", and "treat" are defined as to achieve a desired result (e.g., activate cell signaling) using the composition (e.g., magnetic particle conjugates). "Treatment", as used herein, covers any treatment in a subject (e.g., a mammal, typically a human or non-human animal of veterinary interest).

As used herein, the term "subject" includes humans, mammals (e.g., cats, dogs, horses, etc.), birds, and the like. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a subject. The term "living subject" refers to the entire subject or organism and not just a part excised (e.g., a liver or other organ) from the living subject.

Discussion

Embodiments of the present disclosure provide for magnetic particle conjugates, methods of making the magnetic particle conjugates, methods of using magnetic particle conjugates, micelles (also referred to as a "magnetic composite nanocarrier" (MCNC)), methods of making micelles, methods of using micelles, and the like.

Embodiments of the present disclosure provide for the ability to apply external magnetic fields onto the magnetic particles (e.g., in a magnetic particle conjugate or a micelle) to remotely transfer energy to the magnetic particles. In another embodiment, the agent can be released using an alternative internal thermal energy source (e.g., a metal particle) or an external thermal energy source. In this regard, embodiments of the present disclosure can be used ex vivo and/or in vivo to remote release agents.

Application of the magnetic field causes an energy transfer from the magnetic particle in the form of thermal energy, which causes the agent to be released. In an embodiment, the transfer of energy from the magnetic field to the magnetic particle induces release of the agent from the magnetic particle conjugate or the micelle. For example, the thermal energy may break bonds that release the agent, the thermal energy can disassemble a micelle that releases the agent, or a combination thereof.

In an embodiment, the magnetic field can be generated by electrically conducting coils connected to a power source, or by high-gradient permanent magnets or magnetic materials such as NdFeB or SmCo magnets. For example, the transfer of energy can be communicated using alternating magnetic fields at frequencies of about 100 kHz to 1 MHz, where the frequencies can be adjusted based on the type of magnetic particles, the type of magnetic particle conjugates, the type of micelles, and the like.

Before describing the methods in more detail, embodiments of the magnetic particle conjugate or the micelles are first introduced.

Embodiments of the present disclosure can include a magnetic particle conjugate having a magnetic particle and a polymer having an agent bonded thereto. The polymer can be attached (directly or indirectly) to the magnetic particle. The term "bind", "bond", or "bound" can refer to, but is not limited to, chemically bonded (e.g., covalently or ionically), biologically bonded, biochemically bonded, and/or otherwise associated with the material. In an embodiment, being bound can include, but is not limited to, a covalent bond, a non-covalent bond, an ionic bond, a chelated bond, as well as being bound through interactions such as, but not limited to, hydrophobic interactions, hydrophilic interactions, charge-charge interactions, n-n stacking interactions, combinations thereof, and like interactions. In an embodiment the magnetic particle can include a linker (e.g., a hydrocarbon chain, polymer, and the like) and/or coating (e.g., a polymer or the like) so that the polymer can bind to the magnetic particle indirectly. Additional details are provided in the Examples.

In an embodiment, the polymers can be covalently tethered to the surface of magnetic nanoparticles via diverse coupling reactions including carbodiimide crosslinker chemistry, Cu-catalyzed azide-alkyne cycloaddition, strain-promoted alkyne-azide cycloaddition and thiol-ene chemistry. In addition, ligand exchange approach can allow for the conjugation of oleic acid functional magnetic nanoparticles with polymers that contain terminal anchoring groups such as silane, catechol, or phosphonate. In the case of forming MCNC, polymers interact with nanoparticles via hydrophobic interactions deriving from hydrophobic segments of polymers (e.g., PLA, PCL, PHMA) and surface ligands of magnetic nanoparticles (i.e., oleic acid).

In an embodiment, the magnetic particle has a magnetic moment strong enough to accomplish the desired result (e.g., to vibrate to create thermal energy to increase the temperature to release the agent by breaking the bond between the polymer and the agent). In an embodiment, the magnetic particle includes iron, cobalt, nickel, oxides of each, or combinations thereof. In an embodiment the magnetic particle can be represented by $M^a_x M^b_{(1-x)} Fe_2 O_4$, where each of $M^a$ and $M^b$ is independently a divalent metal such as Fe, Co, Mn, Zn, Ta, Sr, or Ni, where x is 0 to 1, and where $M^a$ and $M^b$ are different metals. In an embodiment, the magnetic particle can be: iron oxide, $Fe_3O_4$, $\gamma Fe_2O_3$, $\alpha Fe_2O_3$. In an embodiment, the magnetic particle can be $SrFe_{12}O_{19}$ or $BaFe_{12}O_{19}$. In an embodiment, the magnetic particle can have a diameter on the micro-scale (e.g., about 500 nm to 10 µm) or nano-scale (e.g., about 10 to 500 nm, about 10 to 200 nm, about 10 to 100 nm, or about 10 to 50 nm).

In an embodiment, the polymer can include thermally degradable group(s) (Q) that bond to the agent, where the bonds can be broken using thermal energy from the magnetic particles. In an embodiment, the magnetic particle is bonded to the polymer and can be represented by the following:

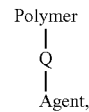

an agent ($A_{gent}$) bonded to the polymer ($P_{olymer}$) through thermally degradable group Q. A plurality (e.g., 2 to 10,000) of $-Q-A_{gent}$ groups can be bonded to the backbone of the $P_{olymer}$. In an embodiment, Q can be a retro-Diels-Alder group, an azo group, a peroxide group, or an alkoxyamine group. In an embodiment, the polymer can include two or more different types of Q groups (e.g., different types of Diels-Alder groups, different types of azo groups, a mixture of Diels-Alder group and azo groups and other combinations as desired to accomplish the particular goal).

In an embodiment, Q can be one of a number of types of Diels-Alder groups, where the Diels-Alder substitutions can be used to design Q to have particular properties. For example, Diels-Alder cycloadditions can proceed more favorably with electron-rich dienes and electron-poor dienophiles. In an embodiment, the addition of strongly electron-donating substituents (e.g., alkyl and alkoxy) to the furan can stabilize the DA adduct, resulting in lower reaction free energies and high barriers to retrocyclization (retro-DA reaction). As shown in Schematic 1.1A-1C below, the stability of furan-maleimide linkage is stronger with electron-donating substituents on the furan. This suggests retro-Diels-Alder (rDA) reaction should take place at higher temperature when electron-donating substituent is on furan. On the other hand, when electron-withdrawing substituents are added to the furan, the retro-DA reaction may proceed at much higher temperatures (Schematic 1.1C below). Therefore, rDA reaction should occur from highest temperature to lowest temperature in the order of alkoxy-, alkyl-, and ester-substituted furan-maleimide DA linkages, for example.

Schematic 1.1: (1.1A) Dynamic-covalent equilibrium of alkoxy substituted furan-maleimide DA adduct; (1.1B) dynamic-covalent equilibrium of alkyl furan-maleimide DA adduct; (1.1C) dynamic-covalent equilibrium of ester furan-maleimide DA adduct.

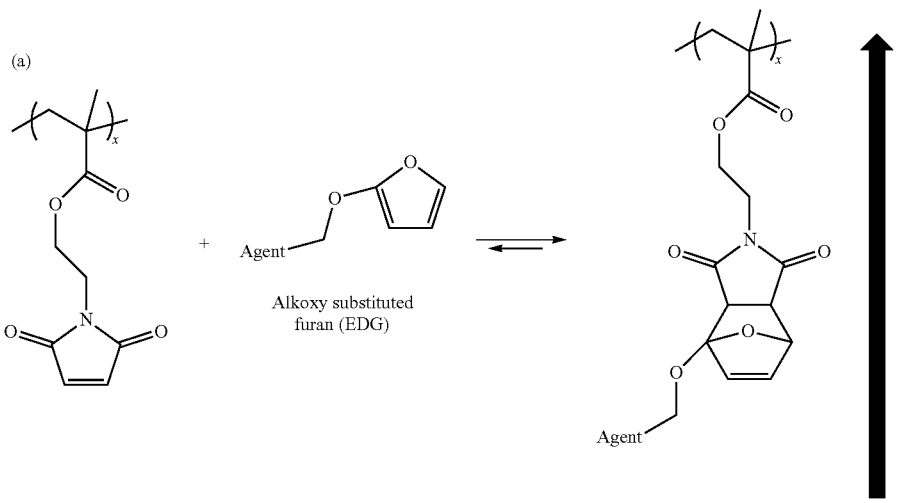

(b)
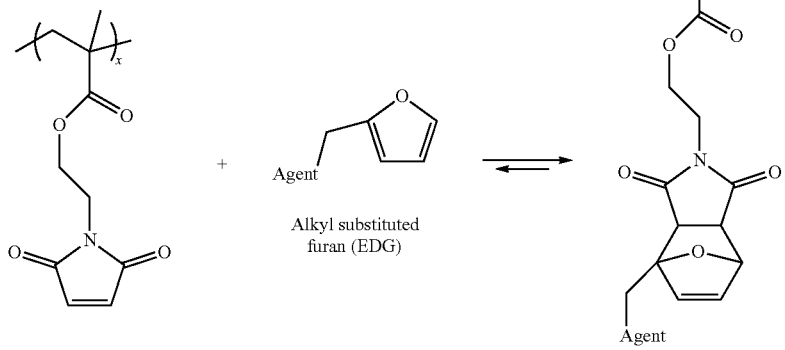
Alkyl substituted furan (EDG)
DA adduct Stability
(c)
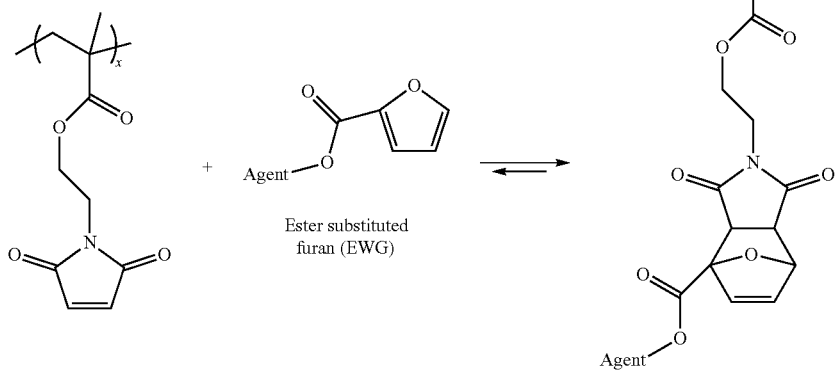
Ester substituted furan (EWG)
Furthermore, when substituents are placed on the 3 position of furan, the stability of DA product should be higher due to steric effect. Therefore, rDA reaction should occur at higher temperature when it is 3-substituted furan-maleimide DA linkage (Schematic 1.2).

Schematic 1.2. (1.2A). Forward and reverse DA reaction of 2-substituted furan and maleimide functional polymer; (1.2B). Forward and reverse DA reaction of 3-substituted furan and maleimide functional polymer.
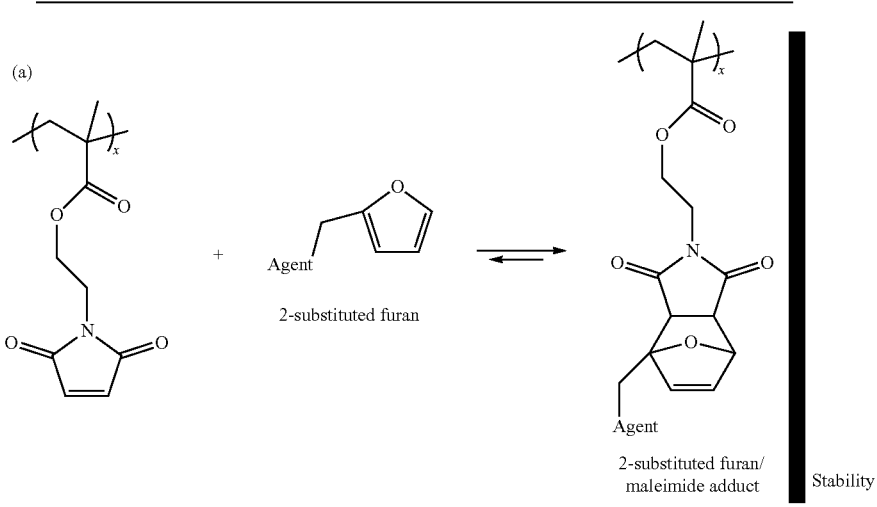
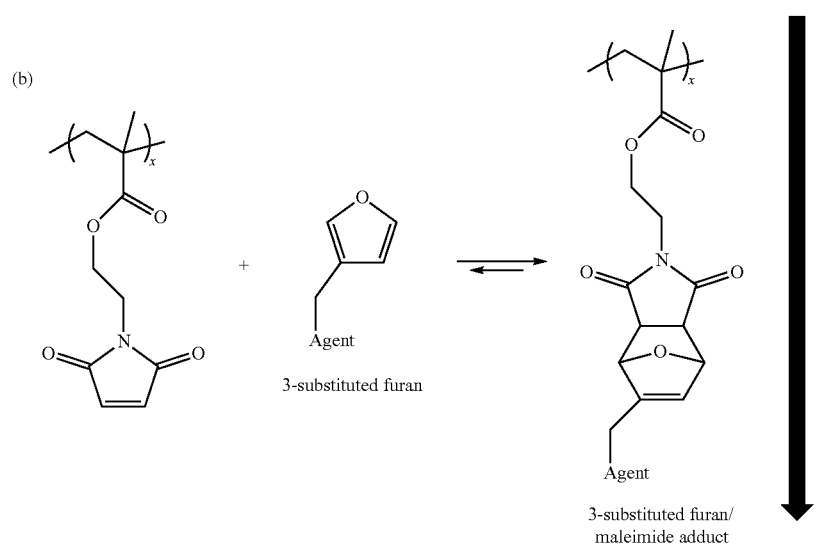

Thus, various types of retro-Diels-Alder group can be substituted (e.g., an alkoxy group (—CH$_2$—O—), an alkyl group (—(CH$_2$)$_n$—, and/or a ester group (—C(O)—O—)) and/or positioned on 2 or 3 carbon to tune the temperature at which rDA can occur. In an embodiment, the polymer can include different types of Qs to control the release as a function of temperature.

In an embodiment, the polymer can be represented by:

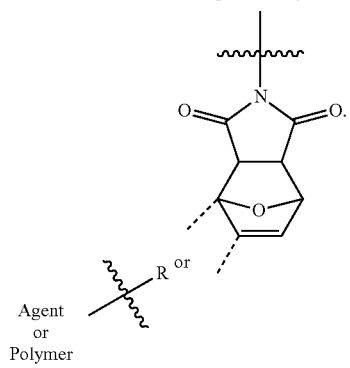

In an embodiment, the polymer or agent can be optionally linked (e.g., bonded directly or indirectly) to the furan group through the 2 or 3 position. In an embodiment, the polymer or agent can be optionally linked (e.g., bonded directly or indirectly) to the N. In an embodiment, R can be selected from: an alkoxy-type group (—CH$_2$—O—), an alkyl-type group (—(CH$_2$)$_n$—, or a ester-type group (—C(O)—O—), where n can be 1 to 10.

In an embodiment, the polymer can include a plurality of moieties that involves a retro-Diels-Alder reaction to release the agent since the Diels-Alder bond is stable at biological temperatures. In an embodiment, the moiety can include a retro-Diels-Alder group that is attached to the magnetic core, where the retro-Diels-Alder-group can be:

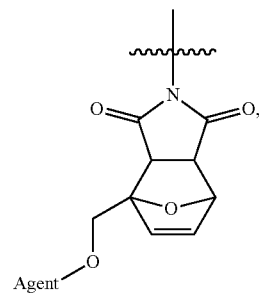

where the nitrogen is bonded (directly or indirectly) to the polymer. In an embodiment, the bonding of the A$_{gent}$ and the polymer can be reversed. In an embodiment, the polymer may include other moieties that are biocompatible (e.g., PEG, poly (N-(2-Hydroxypropyl) methacrylamide) (PHPMA), poly(PEGMA), polyoxazoline, polybetaines). In an embodiment, the retro-Diels-Alder group may be in one block and the biocompatible moiety in another block of a block-copolymer.

An advantage of embodiments of the present disclosure is the stability of the Diels-Alder bond at physiologic temperatures because no drug release is expected unless an alternating magnetic field is applied. Advantageously, the thermal energy released from the magnetic nanoparticle composite is sufficient to break the Diels-Alder bond even though the bulk temperature remains at the physiologic level, hence the mechanism of triggered drug delivery is not dependent on achieving hyperthermia temperatures in the targeted tissue. By contrast, other nanotechnologies developed for magnetically triggered drug delivery either continuously release their cargo, with an increase in release rate due to application of an AMF, or require an increase in bulk temperature to actuate release, which may be difficult to achieve in vivo.

In an embodiment, the magnetic particle conjugate is biocompatible and can have diameters conducive to accumulation in tumors, for example, through the permeation and retention effect. In this way the agent can be released at the tumor site for maximal impact, while limiting off-site undesired side effects.

In an embodiment, the polymer can include the following unit:

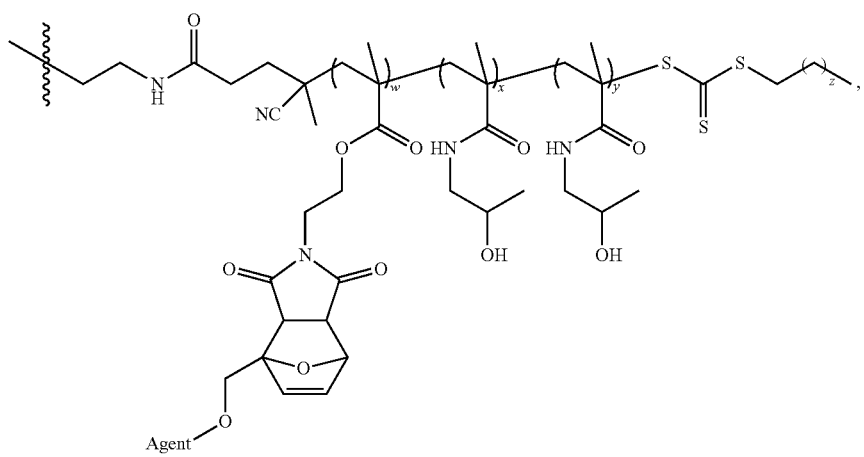

wherein w is 0 or 1 to 20 or 14, x is 20 to 0 or 1, or 11, y is 20 to 60 or 40, and z is 0 or 1 to 10 or 8, where the polymer can be optionally bonded to the magnetic core on the left of the structure. In an embodiment, the unit noted above can be part of a block copolymer with one or more other units such as a biocompatible unit. In an embodiment, the agent and the polymer bonding can be reversed.

In an embodiment, Q can be an azo group. For example, initially, excess ACVA (10 equiv. to therapeutics) can be used to react with amine-containing drugs (e.g., DOX), giving rise to ACVA-DOX which contains a carboxylic acid in the alpha-end. Further, ACVA-DOX can be simply conjugated to the side-chain (i.e., hydroxyl groups) of PHPMA via esterification. In an embodiment, different types of azo groups with various substituents can be used to control the release as a function of temperature. The following table lists various commercial available azo based initiators that can be used as Q. Of the ones listed, each have different 10 hour half-life temperature, which is indicative of a variety of decomposition kinetics. Embodiments of the polymer can be prepared with these azo group linkages within the backbone to tune the temperature at which degradation occurs. In addition to the initiators shown below, other azo groups are known in the art that can be used, some of which are commercially available from Wako Chemical, Japan or can be prepared by common organic chemistry techniques. Example 2 illustrates an embodiment including the azo group bonding structure.

VA-044
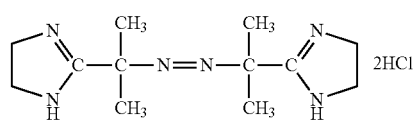
10 hour half-life decomposition temperature: 44° C.

VA-050
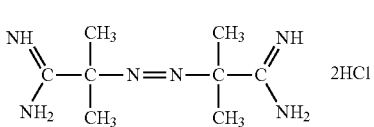
10 hour half-life decomposition temperature: 56° C.

-continued

VA-054
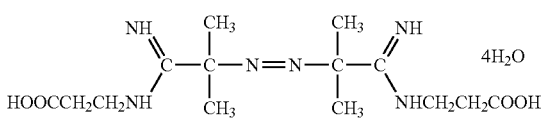
10 hour half-life decomposition temperature: 57° C.

VA-061
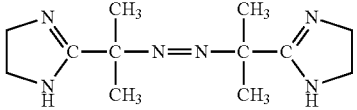
10 hour half-life decomposition temperature: 61° C.

VA-086
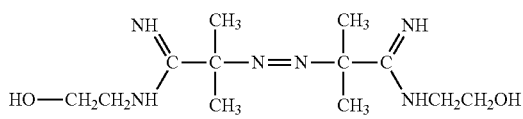
10 hour half-life decomposition temperature: 86° C.

V-501
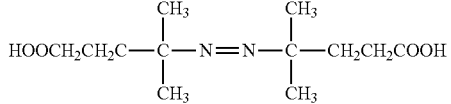
10 hour half-life decomposition temperature: 69° C.

In an embodiment, the polymer ($P_{olymer}$) backbone can be hydrophilic, hydrophobic, or amphiphilic. In an embodiment, the $P_{olymer}$ backbone can include block copolymers of poly(ethylene glycol), poly(oxazolines), poly(s-caprolactone), poly(D/L-lactic acid), acrylamide-based monomers, methacrylamide-based monomers, acrylate-based monomers, methacrylate-based monomers, including, for example, N-(2-hydroxypropyl) methacrylamide and maleimide functional methacrylate, poly(β-thioesters) optionally containing multiple thermally-sensitive azo bonds, or random copolymers of hexyl methacrylate and maleimide functional methacrylate. Polymers containing maleimide functionality are capable of loading furan-modified agents (e.g., a chemical or biological agent) via reversible covalent Diels-Alder linkages.

As mentioned above, the magnetic particle conjugate can include one or more agents (e.g., a chemical or biological agent), where the agent can be attached to the magnetic particle conjugate via the polymer. In an embodiment, the magnetic particle conjugate can include different types of bonds (e.g., Diels-Alder, azo, and the like). In an embodiment, a mixture of magnetic particle conjugate can be provided, where first set of magnetic particle conjugates can include a first type of agents and a second set of magnetic particle conjugates can include a second type of agent, where the first and second agent are different.

In general, the agent can be bonded to the polymer by a covalent bond and be released by a reaction (e.g., a retro-Diels-Alder reaction or an azo reaction) driven by the thermal energy from the magnetic particles, for example. The agent can be administered to the subject to treat, image, detect, study, monitor, and/or evaluate a condition or an occurrence, or the like in the subject. In an embodiment, the agent can include, but is not limited to, a drug, a therapeutic agent, a radiological agent, a small molecule drug, a biological agent (e.g., polypeptides (e.g., proteins such as, but not limited to, antibodies (monoclonal or polyclonal)), antigens, nucleic acids (both monomeric and oligomeric), polysaccharides, haptens, sugars, fatty acids, steroids, purines, pyrimidines, ligands, and aptamers) and combinations thereof, that can be used to image, detect, study, monitor, evaluate, and the like. In an embodiment, the agent is included in an effective amount to accomplish its purpose, where such factors to accomplish the purpose are well known in the medical arts.

In an embodiment, the magnetic particle conjugate can include a targeting agent, where the targeting agent has an affinity for a target (e.g. a target cell, tissue, tumor, or biological component associated with any of these). "Affinity" as used herein refers to the targeting agent having a stronger attraction towards the target relative to other components of the biological environment. In an embodiment, the targeting agent can include, but is not limited to, a chemical agent, a biological agent (e.g., polypeptides (e.g., proteins such as, but not limited to, antibodies (monoclonal or polyclonal), fragments of antibodies), antigens, nucleic acids (both monomeric and oligomeric), peptoids, polysaccharides, haptens, sugars, fatty acids, steroids, purines, pyrimidines, ligands, and aptamers) and combinations thereof, that have an affinity for the target. For example, a targeting agent for a particular type of cancer or tumor can be used to deliver the magnetic particle conjugate (or micelle) to the cancer or tumor and then the alternating magnetic field can be applied so the agent is released at the location of the cancer or tumor.

In an embodiment, agents (e.g., the same agent or two or more types of agents) can be delivered using the magnetic particle conjugate. In particular, one or more types of magnetic particle conjugate are introduced (e.g., administered) to the subject. After an appropriate period of time, an alternating magnetic field can be directed to a portion of the subject (e.g., location where the agents are to be released) to cause an energy transfer from the magnetic particle in the form of thermal energy, which causes the agent to be released. Specifically, the bond between the agent and the polymer is broken by the thermal energy and the agent is released. In an embodiment, the magnetic field can be applied at certain times of the day. The term "periodically" refers to applying the magnetic field at established time frames that may be at regular or irregular time intervals on the time frames of seconds, hours, days, weeks, or months (e.g., about 1 s to 2 months, about 1 hour to 1 day, about 1 day to 1 month, or other the like) depending upon the specific circumstances. In an embodiment, the impulses of the magnetic field can last on the time frame of milliseconds, seconds, hours, or days (e.g., about 1 millisecond to 1 day, about 10 seconds to 1 hour, about 1 minute to 12 hours, about 1 hour to 1 day, or the like) depending upon the specific circumstances. The time frame and duration of magnetic field can be designed based on particular circumstances and requirements of a specific situation. As mentioned above, a targeting agent can be used to direct the magnetic particle conjugate to the desired location of the subject so that the agent is released at the desired location to maximize the benefits with a reduced load relative to systemic administration of the agent to the subject.

Now having described embodiments of the magnetic particle conjugate, embodiments of the micelle (or MCNC) are now described. An embodiment of the present disclosure includes a micelle that can be dissembled using an alternating magnetic field to deliver the agent. In an embodiment, the micelle can include a plurality of magnetic particles, a plurality of amphiphilic polymers, and a plurality of agents that can be encapsulated by a polymer (e.g., a block copolymer such as those in Example 2 and 3). In an embodiment, the magnetic particles, amphiphilic polymers, and/or agents can be optionally bonded to one another (e.g., a magnetic particle is bonded to one or more amphiphilic polymers, one or more agents are bonded to the amphiphilic polymer, one or more agents are bonded to the magnetic particles, or one or more agents are bonded to the amphiphilic polymer and one or more of these amphiphilic polymers are bonded to the magnetic particles), while in another embodiment, the magnetic particles, amphiphilic polymers, and agents are not bonded to one another and are just distinct components of the micelle. The magnetic particles described above and herein can be used in the micelle. The agents described above and herein can be used in the micelle. In addition, the micelle can include targeting agents such as described in relation to the magnetic particle conjugate. Additional details are provided in the Examples, in particular Examples 2 and 3.

In an embodiment, the magnetic particles, amphiphilic polymers, and agents are not bound to one another and are disposed freely in the hydrophobic core of the micelle and encapsulated by a block copolymer that has thermally labile backbone bonds along the hydrophobic block. In addition, other components such as other nanoparticles (e.g., gold nanoparticles), excipients, and the like can be disposed in the core. In an embodiment, the hydrophobic block copolymer has thermally labile backbone moieties such as an azo moiety (such as those described but within the polymer backbone) or a Diels-Alder moiety (such as those described herein, but within the polymer backbone). Example 2 illustrates an exemplar hydrophobic block copolymer having thermally labile backbone bonds. In an embodiment, the micelle may or may not include a magnetic particle and the thermally labile bonds are broken using an external source of heat (hyperthermia), microwaves, or high intensity focused ultrasound.

In an embodiment, thermally labile polymers including the agent can be disposed in the core of the micelle, and optionally, the micelle core can also include magnetic particles, other nanoparticles (e.g., gold nanoparticles, unbound or bound), agents (unbound), excipients, and the like. In an embodiment, the thermally liable polymers including the agent can have the form: $P_{olymer}$-Q-$A_{gent}$, as described below. In an embodiment, the core can be encapsulated in an amphiphilic block copolymer such as PCL-PEG, PLA-PEG, PLGA-PEG, or similar block copolymers with the hydrophilic PEG block replaced by another biocompatible and/or hydrophilic block. In another embodiment, the core can be encapsulated with a block copolymer that has thermally labile backbone bonds as described above. In an embodiment, the micelle may or may not include a magnetic particle and the thermally labile bonds are broken using external source of heat (hyperthermia), microwaves, or high intensity focused ultrasound.

In an embodiment of the micelle, the polymer can be one of those as described herein (above and in the examples). In an embodiment, the polymer used in the micelle can include one or more of a thermally degradable group(s) (Q) that bond to the agent, where the bonds can be broken using thermal energy from the magnetic particles. In an embodiment, the magnetic particle is bonded to the polymer and can be represented by the following:

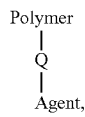

Polymer
|
Q
|
Agent, an agent ($A_{gent}$) is the agent bonded to the polymer ($P_{olymer}$) through thermally degradable group Q, where $A_{gent}$ and Q have been described in detail herein. The polymer can include a plurality (e.g., 1 to 10,000) of -Q-$A_{gent}$ moieties along the backbone of the polymer. Briefly, Q can be a retro-Diels-Alder group or an azo group or other groups disclosed herein. In an embodiment, the polymer can include two or more different types of Q groups (e.g., different types of Diels-Alder groups, different types of azo groups, a mixture of Diels-Alder group and azo groups and other combinations as desired to accomplish the particular goal).

In an embodiment, the magnetic particle conjugates, as described herein, are disposed in the core of the micelle. In an embodiment, the core can be encapsulated in an amphiphilic block copolymer such as PCL-PEG, PLA-PEG, PLGA-PEG, or similar block copolymers with the hydrophilic PEG block replaced by another biocompatible and/or hydrophilic block. In another embodiment, the core can be encapsulated with a block copolymer that has thermally labile backbone bonds as described above.

In an embodiment, the micelle can include about 1 to 78,000 magnetic particles, where the number of magnetic particles can vary depending upon the diameter of the micelle and the diameter of the nanoparticles. In an embodiment, the central region of the micelle has a diameter of about 50 nm to 200 nm. In an embodiment, the micelle can have a diameter of about 50 nm to 500 nm or about 100 nm to 200 nm.

In an embodiment, the amphiphilic polymer has a hydrophobic region and a hydrophilic region, where the hydrophobic region is located in a central region of the micelle and the hydrophilic region is located away from the central region and forms the outer boundary of the micelle. A portion of the magnetic particles and a portion of the agents are located in the central region of the micelle, where each "portion" is independent of one another and "portion" can include about 50 to 100%, about 50 to 95%, about 70 to 100%, about 70 to 95%, about 85 to 90% or about 85 to 90%. In an embodiment, the hydrophobic region of one of more of the amphiphilic polymers of the micelle can, optionally, be bound to the magnetic particle.

As discussed above, the amphiphilic polymer includes a hydrophobic region and a hydrophilic region. In an embodiment, the hydrophobic region can include hydrophobic blocks including one or more of the following: PLA, PGA, PLGA, PCL, and poly(trimethylene carbonate) (PTMC) In an embodiment, the hydrophilic region can include hydrophilic blocks including one or more of the following: PEG, zwitterionic, PHPMA, and Poly(PEGMA). In an embodiment, the amphiphilic polymer can have a molecular weight of about 7,000 to 100,000. In an embodiment, the amphiphilic polymer can include PEG-b-PLA, PEG-b-PLGA, PHPMA-b-PLA, and PHPMA-b-PTMC. Additional details are provided in the Examples.

In an embodiment, the micelle can include targeting agents, as discussed above, where the targeting agents would be located (part of the amphiphilic polymer or bonded to the amphiphilic polymer near or at the micelle outer boundary.

In an embodiment, agents (e.g., the same agent or two or more types of agents) can be delivered using the micelle. In particular, one or more types of micelles are introduced (e.g., administered) to the subject, where each micelle includes one or more types of agents or one or more types of magnetic particles. After an appropriate period of time, an alternating magnetic field can be directed to a portion of the subject (e.g., location where the agents are to be released) to cause an energy transfer from the magnetic particle in the form of thermal energy, which causes the agent to be released as the micelle is dissembled into its component parts. In an embodiment, the magnetic field can be applied at certain times of the day in a similar manner as described in relation to the magnetic particle conjugates. The time frame and duration of magnetic field can be designed based on particular circumstances and requirements of a specific situation. As mentioned above, a targeting agent can be used to direct the micelles to the desired location of the subject so that the agent is released at the desired location to maximize the benefits with a reduced load relative to systemic administration of the agent to the subject.

In another embodiment, the magnetic particles can be replaced with another particle that can be heated. For example, the magnetic particle can be replaced with a metal nanoparticle (e.g., about 10 to 500 nm in diameter) such as gold as well as nanoshells such as gold nanoshells, or the like that can be generate and increase in temperature by absorbing light and/or acoustic energy. In an embodiment, the composition can include magnetic particles and one or more types of other particles (e.g., gold nanoparticles).

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

Example 1

We have developed a novel magnetically triggered drug delivery platform consisting of magnetic nanoparticles (MNPs) coated with a biocompatible polymer and conjugated to therapeutic agents through a thermally labile Diels-Alder bond. Upon application of an alternating magnetic field (AMF), the MNPs release thermal energy breaking the bonds and actuating release of the drug. In the absence of the AMF the drug is safely shielded from the environment by being encapsulated in the biocompatible polymer shell. These magnetically triggered drug delivery vehicles (mtDDVs) possess two key unique features: (i) because of the stability of the Diels-Alder bond at physiologic temperature, no release of the drug is expected unless an AMF is applied; (ii) the thermal energy released from the MNPs is sufficient to break the Diels-Alder bond even though the bulk temperature remains at the physiologic level, hence the mechanism of triggered drug delivery is not dependent on achieving hyperthermia temperatures in the targeted tissue. Other nanotechnologies developed for magnetically triggered drug delivery either continuously release their cargo, with an increase in release rate due to application of an AMF, or require an increase in bulk temperature to actuate release, which is difficult to achieve in vivo.

The developed mtDDVs possess a biocompatible outer coating and are small, making them suitable for systemic delivery. In the case of cancer applications the mtDDVs are expected to accumulate passively in tumors through the enhanced permeation and retention effect. The mtDDVs can also contain a targeting agent (such as a peptide, peptoid, aptamer, antibody, or antibody fragment) to promote accumulation in the intended tissue and uptake by targeted cells. Furthermore, through control of the region where the AMF is applied, drug release can be limited to the intended tissue, dramatically decreasing any off-site side effects associated with the drug payload. As such, the proposed nanotechnology is suitable for localized targeted therapy and for combination of systemic administration and targeted therapy.

Results and Discussion

First, furan protected maleimide methacrylate (Fur-MalMA) and (N-hydroxypropyl) methacrylamide (HPMA) were copolymerized in the presence of 4-cyano-4-[(dodecylsulfanylthiocarbonyl)sulfanyl]pentanoic acid (CTA) under redox initiating system using benzoyl peroxide (BPO) and dimethylaniline (DMA). The resultant copolymer poly (Fur-MalMA-co-HPMA) was subsequently chain-extended with HPMA to produce block copolymer poly(Fur-MalMA-co-HPMA)-b-PHPMA (FIG. 1.1). Successful production of poly(Fur-MalMA-co-HPMA)-b-PHPMA was proven by $^1$H NMR spectroscopy, showing that the intensity of signals attributed to hydroxyl protons (h) of HPMA units increased after chain extension with HPMA (FIG. 1.2). Furthermore, gel permeation chromatography (GPC) displayed a shift in molecular weights from 5, 100 to 17, 600 g/mol, indicating the successful addition of second block to poly(Fur-MalMA-co-HPMA). (FIG. 1.3).

According to FIGS. 1.4A-B, random copolymer poly(Fur-MalMA-co-HPMA) was capable of self-assembling into nanoparticles, thus may reducing accessibility of COOH groups on the hydrophobic side. To enhance water solubility of polymer, second chain PHPMA was added and DLS showed the size of block copolymer poly(Fur-MalMA-co-HPMA)-b-PHPMA was only 9 nm, in good agreement of the form of disassembled unimers.

To explore the condition of deprotection of furan, poly (Fur-MalMA-co-HPMA) was subjected in DMF at 105° C. for 8 hours (FIG. 1.5). Thereafter, the disappearance of Diels-Alder linkages protons (c) was found by $^1$H NMR spectroscopy, suggesting that the efficiency of deprotection was 100% under this condition.

Next, poly(Fur-MalMA-co-HPMA)-b-PHPMA was conjugated to amino-containing magnetic nanoparticles (APS-MNPs) via amidation using carbodiimide chemistry (FIG. 1.6). The resultant Polymer-MNPs conjugate was further heated at 105° C. to remove furan and yield free maleimide groups in the conjugate. The successful conjugation of polymer to MNPs were proven by Fourier transform infrared spectroscopy (FTIR), displaying that deprotected polymer-MNPs include the IR signals of both original polymer and APS-MNPs. Moreover, 1710 and 2930 cm$^{-1}$ attributed to free maleimide groups were observed in deprotected polymer-MNPs conjugates (FIG. 1.7A). The stability of polymer-MNPs were also tested. As is shown in FIG. 1.7B, polymer-MNPs were stable in buffer (pH 9) for 7 days while APS-MNPs sedimented instantly in the same condition. This can be attributed to the enhanced water-solubility of conjugates endorsed by coated polymer.

Furan functional fluorescein (Fur-Fluo) was then bonded to maleimide containing polymer-MNPs conjugate via DA reaction at 25° C. for 7 days (FIG. 1.8). Excessive Fur-Fluo was removed by 10 times of centrifugation.

Then the release study was carried out in water under 23° C., 80° C., and AMF (FIG. 1.9).

Materials and Methods

Materials

Furan protected maleimide methacrylate (Fur-MalMA), (N-hydroxypropyl) methacrylamide (HPMA), benzoyl peroxide (BPO), dimethylaniline (DMA), 4-cyano-4-[(dodecylsulfanylthiocarbonyl)sulfanyl]pentanoic acid (CTA), dimethylformamide (DMF), APS-MNPs, furan fluorescein (Fur-Fluo), N-(3-dimethylaminopropyl)-N'-ethylcarbodiimide hydrochloride (EDC.HCl), and 4-dimethylaminopyridine (DMAP).

Methods

1. RAFT Polymerization of Fur-MalMA and HPMA

In a typical procedure, Fur-MalMA (0.50 g, 1.8 mmol), HPMA (0.77 g, 5.4 mmol), CTA (29 mg, 0.072 mmol), and BPO (12 mg, 0.036 mmol) were dissolved in DMF (4.0 mL), followed by purging with nitrogen for 10 min. Under flush of nitrogen, DMA (4.6 µL, 0.036 mmol) was added to the solution. Then the vial was placed into a preheated oil bath at 30° C. for 4 h. The reaction was quenched by exposure to air. Polymer product was collected by precipitation into a large excess of cold diethyl ether and dried under vacuum oven at room temperature.

2. RAFT Chain Extension of Poly(Fur-MalMA-Co-HPMA) with HPMA

In a typical procedure, poly(Fur-MalMA-co-HPMA) (150 mg, 0.025 mmol), HPMA (0.36 g, 2.5 mmol), and BPO (3.0 mg, 0.012 mmol) were dissolved in DMF (1.4 mL), followed by purging with nitrogen for 15 min. Under flush of nitrogen, DMA (1.2 µL, 0.012 mmol) was added to the solution. Then the vial was placed into a preheated oil bath at 30° C. for 4 h. The reaction was quenched by exposure to air. Polymer product was collected by precipitation into a large excess of cold diethyl ether and dried under vacuum oven at room temperature.

3. Deprotection of Poly(Fur-MalMA-Co-HPMA)

In a typical procedure, poly(Fur-MalMA-co-HPMA) (100 mg) was suspended in DMF (2 mL) and then heated at 105° C. for 8 h, The reaction was quenched by immersing the vial in ice bath. The final product was collected by precipitation into a large excess of cold diethyl ether and dried under vacuum oven at room temperature.

4. Conjugation of Poly(Fur-MalMA-Co-HPMA)-b-PHPMA to APS-MNPs

In a typical procedure, polymer (580 mg, 0.05 mmol), EDC.HCl (100 mg, 0.50 mmol), DMAP (1.2 mg, 0.01 mmol) and APS-MNPs (15 mg, 0.05 mmol of amine) were dissolved in buffer (pH=5). The mixture was dissolved at room temperature for 24 h. The product was collected by centrifugation and washed by water.

5. Deprotection of Polymer-MNPs Conjugate

In a typical procedure, polymer-MNPs conjugate was suspended in DMF and then heated at 105° C. for 8 h, The reaction was quenched by immersing the vial in ice bath. The final product was collected by centrifugation and washed by water.

6. Immobilization of Fur-Fluo to Polymer-MNPs Conjugate

In a typical procedure, polymer-MNPs conjugate (5 mg) and Fur-Fluo (2 mg) was suspended in DMF and then incubated at 25° C. for 7 days, The final product Fluo-Polymer-MNPs was collected by centrifugation and washed by water.

7. AMF Induced Release of Fluo

In a typical procedure, Fluo-Polymer-MNPs conjugate was suspended in water and then incubated under AMF for various minutes, The released dye was collected by ultra-fast centrifugation and characterized by fluorescence spectroscopy.

Example 2

Micelles (MCNC)

Herein, we present the first example of thermally-degradable poly(β-thioester)s containing aliphatic azo linkages in the backbone of the polymers (polyazo). A novel azo-based diacrylate monomer (ACVADA) was synthesized and copolymerized with excess 1,6-hexanedithiol (HDT) for the preparation of α,ω-telechelic polymers bearing thiol end groups. These thiol groups were further reacted with 2-hydroxyethyl acrylate or PEG acrylate to generate end-capped homopolymers or triblock copolymers, respectively (Scheme 2.1). Thermal cleavage of the incorporated azo units afforded a mixture of lower molecular weight polymers and small molecules. The variables affecting degradation, including temperature, solvent (i.e., organic and aqueous), and presence or absence of hydroquinone (HQ), were thoroughly investigated.

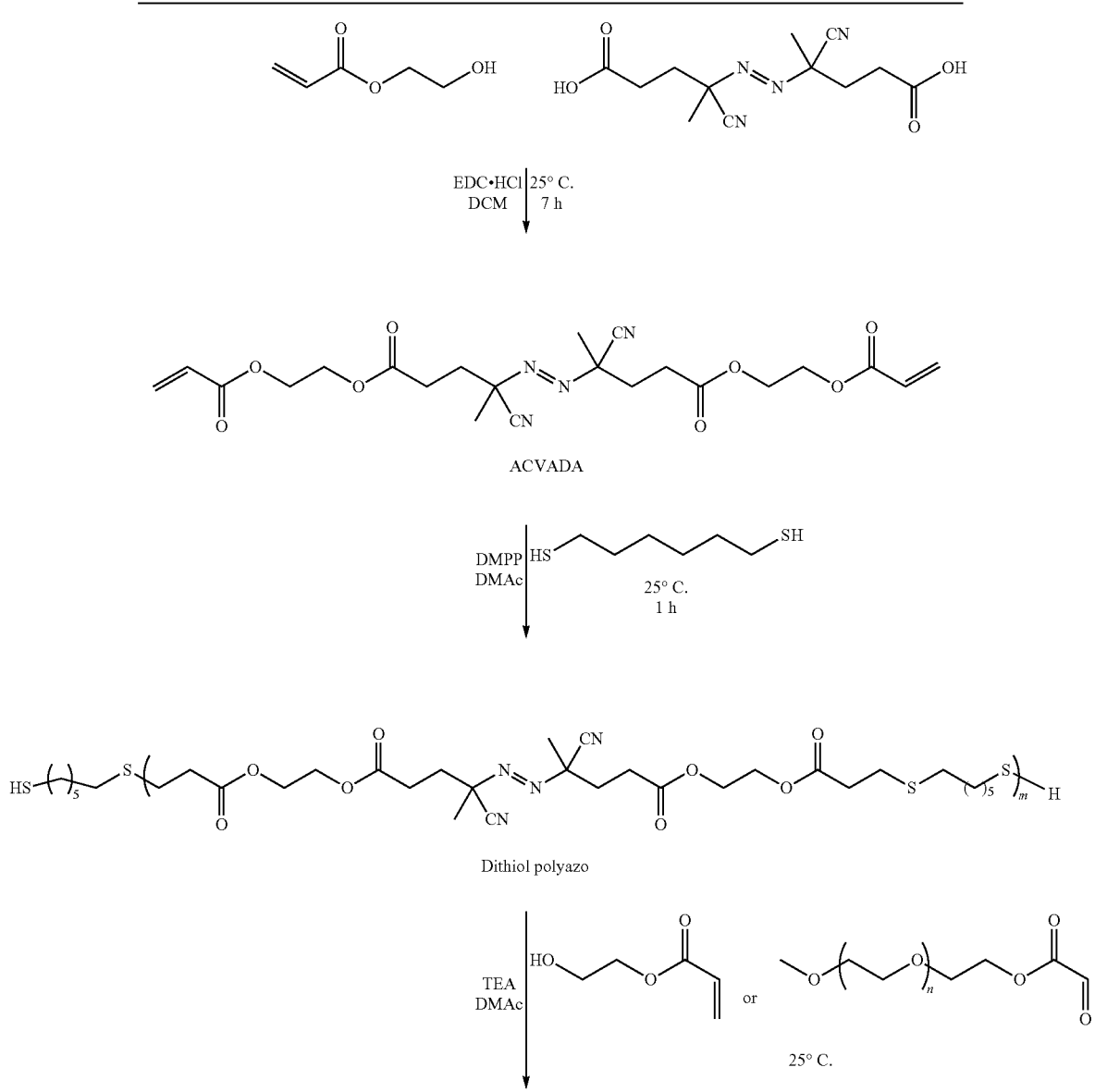

Scheme 2.1. Synthetic route to ACVADA monomer and preparation of homopolymer polyazo and triblock copolymer PEG-b-polyazo-b-PEG by one-pot step-growth polymerization.

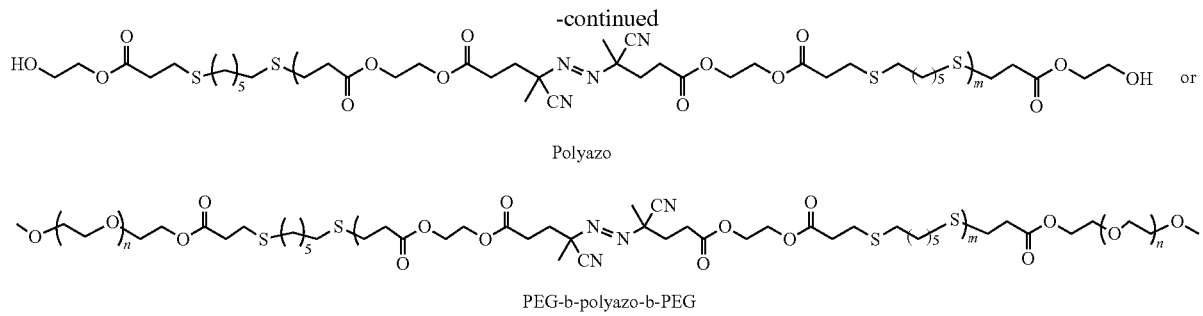

Polyazo

PEG-b-polyazo-b-PEG

We began our preliminary exploration by designing and synthesizing the ACVADA monomer containing a central azo moiety. 4,4'-Azobis(4-cyanovaleric acid) (ACVA) was coupled with two equivalents of 2-hydroxylethyl acrylate using an EDC coupling approach at 0° C. in the absence of light. Successful synthesis of the novel diacrylate compound was confirmed by $^1$H NMR (FIG. 2.1A) and $^{13}$C NMR spectroscopy (FIG. 2.5). Notably, the signal attributed to the protons of the methyl groups at 1.62 ppm splits into two singlet peaks. This result is consistent with the existence of cis and trans isomers in the product of ACVADA.

Next, using dimethylphenylphosphine (DMPP) as the catalyst, step-growth copolymerization of ACVADA and HDT was performed. Thiol-acrylate reactions are highly exothermic and could increase the temperature of the reaction mixture. Therefore, the polymerization was conducted at 0° C. in the absence of light to minimize potential azo dissociation. To synthesize polymers containing terminal thiols which could be further functionalized, an excess of the HDT comonomer was employed in the polymerizations. The molar feed ratios of HDT to ACVADA were 1.16/1, 1.13/1 and 1.08/1, respectively. Monomer conversion of ACVADA was monitored by $^1$H NMR and the disappearance of acrylate groups (5.8-6.5 ppm) was observed after 1 h of polymerization (FIG. 2.1A). Polyazo polymers having three molecular weights (3 000, 3 500 and 6 100 g/mol) were prepared by varying the comonomer ratio (vide supra). Thereafter, polyazo$_{10}$ was further modified with 2-hydroxyethyl acrylate (HEA) via thiol-ene click reaction (Scheme 2.1). In this process, ten equivalents of HEA relative to the terminal thiol groups were added to ensure complete end-group conversion. The $^1$H NMR spectrum confirmed successful Michael addition through the appearance of peaks at 3.82 and 4.25 ppm, ascribed to the methylene protons (k and l) adjacent to the terminal hydroxyl groups (FIG. 2.1B). Following the installation of hydroxyl groups, the possibility of disulfide formation was removed.

Because thermally-labile azo bonds were embedded within the main chain of polyazo, we postulated that the polymers were capable of degrading into small molecules upon heating. Therefore, the thermal degradation behavior of polyazo$_{10}$ was examined. It is well known that the radicals generated by the scission of azo compounds can terminate by several reaction pathways, including disproportionation, recombination, and transfer. Depending on the fates of these radicals, complex degradation mechanisms may result. Among these events, irreversible radical recombination is considered to be the most detrimental to the proposed degradation mechanism of the polymer. To minimize the rate of recombination, we first investigated the effect of adding hydroquinone (HQ), a radical scavenger that can transfer a hydrogen to a carbon-centered radical. In this study, polyazo$_{10}$ ($M_n$=6 100 g/mol) was heated at 95° C. in the absence and presence of HQ (10 equiv. of HQ to azo units). The reduction in the molecular weight of polyazo$_{10}$ upon heating was examined by GPC, which showed longer retention times as the heating time increased (FIGS. 2.2A and 2.2B). For the degradation without HQ, a relatively slow reduction in molecular weight was observed, resulting in a molecular weight of 4 400 g/mol after 10 min of heating. Continuing the heating for 240 min, the molecular weight gradually leveled off at 2 100 g/mol, with no further change in molecular weight at longer reaction times. In the presence of HQ, the molecular weight of polyazo$_{10}$ decreased sharply from 6 100 g/mol to 2 050 g/mol within 10 min of heating (FIG. 2.2C). Subsequently, the degradation proceeded at a slower rate, suggesting most of the degradation had been completed during the first 10 min. These results clearly indicate that the addition of HQ effectively suppresses radical recombination, thus resulting in a larger extent of degradation in terms of apparent molecular weight reduction. Additionally, degradation of the polymer backbone results in the emission of nitrogen gas. Thus, $^{15}$N NMR spectroscopy was utilized to confirm the degradation of polyazo$_{10}$. As shown in FIGS. 2.6A-B, the spectrum of the degradation products showed no resonance at −171 ppm, ascribed to the nitrogen of the azo functionality.

To discern the influence of heating on degradation kinetics, three different degradation temperatures (95, 80 and 60° C.) were studied for polyazo$_{10}$ in the presence of HQ. GPC was used to monitor the decrease in molecular weight at each temperature (FIGS. 2.7A-B). As expected, the reduction of molecular weights was most rapid at 95° C., leading to a final molecular weight of 1 400 g/mol (FIG. 2.2D). Conversely, a slower decrease in molecular weight was observed at 80° C., resulting in a final degraded product with a molecular weight of 2 000 g/mol after heating for 240 min. Finally, only a slight shift in the GPC trace occurred when the polymer was heated at 60° C., indicating that the polymer is highly stable at this temperature throughout the investigated heating time.

The ability of the thiol-terminated polyazo to couple with other suitable polymers is very intriguing in terms of preparing more complex polymers with novel properties. Thus, PEG$_{44}$ acrylate ($M_n$=2 000 g/mol) was synthesized (FIG. 2.8) and conjugated with polyazo$_6$ ($M_n$=3 500 g/mol) (Scheme 2.1). The coupling reaction between PEG$_{44}$ and polyazo$_6$ was monitored by $^1$H NMR spectroscopy. The disappearance of the acrylate signals at 5.8-6.5 ppm indicated that PEG$_{44}$ acrylate was near quantitatively consumed (FIG. 2.3A-B). As shown in FIG. 2.3A, the GPC trace displayed a shift to higher molecular weight, corresponding to the attachment of PEG$_{44}$ to polyazo$_6$. To further verify the topology and purity of the triblock copolymer, diffusion-ordered NMR spectroscopy (DOSY) was utilized (FIG. 2.3B). After the conjugation, polyazo and PEG segments have the same diffusion coefficient ($2.35 \times 10^{-6}$ cm$^2$/s), which is smaller than that of PEG$_{44}$ acrylate ($5.72 \times 10^{-6}$ cm$^2$/s), confirming that PEG$_{44}$ was chemically bound to polyazo$_6$ rather than being physically mixed. To demonstrate the versatility of this approach, PEG$_{110}$ acrylate was conjugated to polyazo$_5$ ($M_n$=3 000 g/mol). Clean and efficient coupling was confirmed by $^1$H NMR spectroscopy and GPC (FIG. 2.9A-B). These results demonstrate the highly efficient nature of thiol-acrylate reactions for the synthesis of triblock copolymers.

Unlike the original polyazo polymer, the resulting triblock copolymer could be dispersed in deionized water due to the water solubility of the PEG blocks. An aqueous solution of PEG$_{14}$-b-polyazo$_6$-b-PEG$_{44}$ was further examined by dynamic light scattering (DLS) and transmission electron microscopy (TEM) (FIGS. 2.3C and 2.3D). TEM provided evidence of self-assembled micelles with a diameter of 18 nm, which was in relatively good agreement with the DLS results ($D_h$=23 nm). Furthermore, upon heating at 95° C. for 1 h, the particle sizes decreased to 2 nm, consistent with degradation of the azo moieties and dissociation of the micelles (FIG. 2.4A). To investigate the effect of solvent, thermal degradation of PEG$_{44}$-b-polyazo$_6$-b-PEG$_{44}$ was also studied in DMAc (i.e., a non-selective solvent) and water (i.e., a selective solvent). In the case of degradation in DMAc, the final product showed a molecular weight of 2 200 g/mol, which is noticeably smaller than that of the final product in water ($M_n$=3 600 g/mol; FIGS. 2.4B and FIG. 2.10). Moreover, the degradation of the triblock copolymer in water is significantly slower than that in DMAc. This can be ascribed to the self-assembled and highly congested environment of the azo moieties within the micelle cores, which results in limited diffusion and increased possibility of radical recombination. Recombination of the radical fragments would limit the chain degradation process. Finally, thermal degradation of PEG$_{44}$-b-polyazo$_6$-b-PEG$_{41}$ and PEG$_{110}$-b-polyazo$_5$-b-PEG$_{110}$ at 95 and 80° C. in DMAc was monitored by GPC (FIGS. 2.11A-B). As expected, the triblock copolymers exhibited rapid decomposition kinetics at 95° C.

In summary, we have designed a robust approach to thermally-labile, main-chain poly(β-thioester)s. Through the utilization of base-catalyzed thiol-ene chemistry, homopolymers of polyazo and triblock copolymers PEG-b-polyazo-b-PEG were prepared in one pot under mild conditions. GPC and $^{15}$N NMR spectroscopy results revealed that polyazo can gradually degrade into small molecular fragments upon heating. The degradation kinetics were dependent on temperature, with significantly enhanced dissociation rate at higher temperatures. Furthermore, the addition of a radical scavenger improved the extent of degradation by limiting radical recombination. Water-soluble PEG-b-polyazo-b-PEG was prepared and characterized by $^1$H and DOSY NMR spectroscopy and GPC. DLS and TEM results demonstrated the self-assembly of these triblock copolymers in water. Interestingly, for the triblock copolymers, the degradation in DMAc was faster than in water at the same temperature, which is likely due to the congested environment of the polyazo segments in the micellar cores present in the aqueous solution, confining the diffusion of radicals. Given the broad application of stimuli-responsive polymers in modern-day biology, medicine, and manufacturing, we believe these novel stimuli-responsive polymers will give rise to a new class of poly(β-thioester)-based materials. Current investigation is in progress to further explore the possibility of preparing polyazo polymers with enhanced responses at lower temperature.

Supplementary Information for Example 2

Materials and Methods

Materials

All chemicals were used as received unless otherwise noted. Poly(ethylene glycol) monomethyl ether ($M_n$=2 kg/mol and 5 kg/mol), 2-hydroxyethyl acrylate (>96%), 4,4'-azobis(4-cyanovaleric acid) (ACVA, >98%), sodium sulfate (>99%), sodium bicarbonate (>99%), sodium chloride (>99%), 1,6-hexanedithiol (HDT, >97%), dimethylphenylphosphine (DMPP, 99%), and N,N-dimethylacetamide (99.8%) were purchased from Sigma-Aldrich. 4-Dimethylaminopyridine (4-DMAP, 98%) was purchased from Acros Organics. Triethylamine (>99%), acryloyl chloride (>96%), and hydroquinone (HQ) (99%) were purchased from Alfa Aesar. 1-Ethyl-3-(3-dimethylaminopropyl)carbodiimide hydrochloride (EDC.HCl, >98%), methanol (99.8%), diethyl ether (99.5%), dichloromethane anhydrous (>99%), and tetrahydrofuran anhydrous (>99.5%) were purchased from TCL.

Methods

Nuclear Magnetic Resonance (NMR)

$^1$H and $^{13}$C NMR spectra were recorded in CDCl$_3$ using an Inova 500 MHz spectrometer at 25° C. $^{15}$N NMR spectra were recorded in CDCl$_3$ using a Mercury 300BB MHz spectrometer at 25° C.

Diffusion Ordered NMR Spectroscopy (DOSY)

DOSY experiments were performed on a Varian Inova spectrometer operating at 500 MHz for $^1$H and equipped with a 5 mm indirect detection probe with z-axis gradients. The samples were run in CDCl$_3$ without temperature regulation to avoid convection. The temperature was 22° C. The pulse sequence used was bipolar pulse pair stimulated echo. The gradient strength was arrayed as equally spaced squares over 15 values in the interval 2-60 Gauss/cm. The gradient duration (δ) was 2 ms and the diffusion delay (Δ) was 200 ms. The spectra were collected with a spectral window from −0.5 to 9.5 ppm in 4 transients and with 8 dummy transients in the beginning, with an acquisition time of 2 s and a relaxation delay of 3 s. The total experiment time was ca. 5 minutes. The data were processed with a line broadening of 2 Hz and baseline correction. Integrals were used for fitting the intensity decay equation and the precision was ca. 1%.

Gel Permeation Chromatography

Molecular weight and polydispersity were determined by gel permeation chromatography (GPC) in dimethylacetamide (DMAc) with 50 mM LiCl at 50° C. and a flow rate of 1.0 mL min$^{-1}$ (Agilent isocratic pump, degasser, and autosampler, columns: PLgel 5 μm guard+two ViscoGel I-series G3078 mixed bed columns: molecular weight range 0-20×10; and 0-100×10$^4$ g mol$^{-1}$). Detection consisted of a Wyatt Optilab T-rEX refractive index detector operating at 658 nm and a Wyatt miniDAWN Treos light scattering detector operating at 659 nm. The system was calibrated using 10 poly(methyl methacrylate) (PMMA) standards from 9.88×10$^5$ to 602 g/mol. Absolute molecular weights and polydispersities were calculated using the Wyatt ASTRA software and the dn/dc for polystyrene (0.1444 mL/g).

High-Resolution Mass Spectrometry (HRMS)

HRMS was carried out using an Agilent 6220 TOF-MS mass spectrometer in the electrospray ionization (ESI) mode.

Transmission Electron Microscopy (TEM):

Five microliters of the sample was applied onto a formvar coated 200-mesh Cu grid that was freshly glow discharged (Pelco easiGlow™, Ted Pella, Inc.). The grids were observed on a Hitachi H7000 microscope operating at 100 kV. The images were recorded with a slow-scan CCD camera (Veleta 2k×2k).

Dynamic Light Scattering (DLS):

Dynamic light scattering (DLS) analysis was conducted at room temperature on a Zetasizer Nano-ZS (Malvern) operating at a wavelength of 633 nm.

Experimental

Synthesis of Diacrylate Monomer (ACVADA)

4,4'-Azobis(4-cyanovaleric acid) (1.0 g, 3.6 mmol) was suspended in dry dichloromethane (50 mL). 1-Ethyl-3-(3-dimethylaminopropyl)carbodiimide hydrochloride (2.1 g, 11 mmol) and 4-DMAP (0.13 g, 1.1 mmol) were added to the solution at 0° C. The mixture was stirred for 0.5 hour, followed by slow addition of 2-hydroxylethyl acrylate (0.91 mL, 7.9 mmol) at 0° C. The reaction was left to stir in an ice bath overnight. After the reaction, the solution was diluted to 100 mL with DCM and sequentially washed with HCl solution (1M), saturated sodium bicarbonate solution (1 M) and brine. Following the wash process, the organic layer was dried over sodium sulfate and concentrated by rotary evaporator. The crude product was further purified by flash chromatography on silica gel with ethyl acetate/hexane (9:1) to yield the product as colorless viscous oil (0.92 g, 54.1%). $^1$H NMR (500 MHz, $CDCl_3$): δ (ppm) 6.40 (m, 2H), 6.09 (m, 2H), 5.82 (m, 2H), 4.31 (s, 8H), 2.23-2.58 (m, 8H), 1.65 (d, 6H); $^{13}$C NMR (125 MHz, $CDCl_3$): δ (ppm) 171.1, 165.8, 131.5, 127.9, 117.4, 71.9, 62.8, 62.0, 33.1, 29.0, 23.9, 23.7. ESI-HRMS: Calcd for $[M+Na]^+$: 499.1799. Found: 499.1779.

Synthesis of Thermally-Degradable Polyazo Bearing Terminal Hydroxyl Groups

In a typical polymerization procedure ($[HDT]_0$:$[ACVADA]_0$ feed ratio of 1.05:1), 1,6-hexanedithiol (0.26 mL, 1.7 mmol) and DMPP (1 μL) were dissolved in DMAc (2 mL). The solution was placed into an ice bath and purged with $N_2$ for 10 min. Thereafter, ACVADA (0.772 g, 1.62 mmol) in 0.5 mL DMAc was added dropwise into the solution while purging with $N_2$ for another 10 min. The reaction mixture was further stirred at 25° C. for 1 h. After the polymerization, 2-hydroxyethyl acrylate (0.19 mL, 1.7 mmol) and TEA (5 μL) was added to the solution. The reaction was left at 25° C. for 4 hours. Polyazo was isolated by precipitating into a large volume of cold methanol. The precipitate was dried under vacuum at room temperature for 24 h.

Synthesis of PEG Acrylate

PEG acrylate of two molecular weights (2000 and 5000 g/mol) was synthesized. In a typical procedure for preparing $PEG_{44}$ acrylate, $PEG_{44}$ monomethyl ether (5.0 g, 2.5 mmol) and TEA (1.74 mL, 12.5 mmol) were dissolved in dry THF (100 mL). The solution was then placed into an ice bath and acryloyl chloride (1.02 mL, 12.5 mmol) was added dropwise into the solution. Following the addition, the reaction mixture was left to stir at 25° C. overnight. When the reaction was completed, salt was removed by filtration and THF was removed under vacuum. Then the concentrated residue was dissolved into DCM (50 mL) and washed sequentially with HCl solution (1 M), saturated sodium bicarbonate solution (1 M) and brine. The organic phase was dried over sodium sulfate and then concentrated under vacuum. $PEG_{44}$ acrylate was obtained by precipitating into a large volume of cold diethyl ether. Polymer was dried under vacuum at room temperature for 24 h.

Synthesis of Triblock Copolymers PEG-b-Polyazo-b-PEG

In a typical procedure for the preparation of $PEG_{44}$-b-$polyazo_6$-b-$PEG_{44}$, 1,6-hexanedithiol (0.26 mL, 1.7 mmol) and DMPP (1 μL) were dissolved in DMAc (2 mL). The solution was placed into ice bath and purged with $N_2$ for 10 min. Then ACVADA (0.717 g, 1.50 mmol) in 0.5 mL DMAc was added dropwise while purging with $N_2$ for another 10 min. The reaction mixture was further stirred at 25° C. for 1 h. After the polymerization, $PEG_{44}$ acrylate (1.2 g, 0.61 mmol) and TEA (2 μL) were dissolved into DMAc (1 mL) and then added dropwise to the solution. The reaction was left at 25° C. for 17 h. $PEG_{44}$-b-polyazo-b-$PEG_{44}$ was isolated by precipitating into a large volume of cold diethyl ether. The precipitate was dried under vacuum at room temperature for 24 h.

Thermal Degradation of Polyazo in DMAc

In a typical procedure (degradation in the presence of hydroquinone), polyazo (100 mg) and hydroquinone (21 mg, 0.19 mmol) were dissolved in DMAc (5 mL), and the reaction mixture was heated in an oil bath at predetermined temperatures (60, 80 and 95° C.). Samples were taken periodically, quenched in liquid nitrogen, and immediately analyzed by GPC at predetermined time points.

Thermal Degradation of $PEG_{44}$-b-$polyazo_6$-b-$PEG_{44}$ Based Micelles in DMAc $PEG_{44}$-b-$polyazo_6$-b-$PEG_{44}$ (20 mg) was dissolved in DMAc (1.6 mL), and the reaction mixture was heated in an oil bath at 95° C. Samples were taken periodically, quenched in liquid nitrogen, and immediately analyzed by GPC at predetermined time points.

Thermal Degradation of $PEG_{44}$-b-$Polyazo_6$-b-$PEG_{44}$ Based Micelles in Water $PEG_{44}$-b-$Polyazo_6$-b-$PEG_{44}$ (20 mg) was dissolved in $H_2O$ (1.6 mL), and the reaction mixture was heated in an oil bath at 95° C. Samples were taken periodically, quenched in liquid nitrogen, lyophilized, and analyzed by GPC at predetermined time points.

Example 3

Herein we prepared a copolymer of Fur-MalMA and hexylmethacrylate (HMA) in the presence of AIBN at 60° C. Following that, deprotection was carried out at 110° C. to give rise to poly(MalMA-co-HMA) that contains pendant free maleimide functionalities. Scheme 3.1, shown in FIG. 3.1, illustrates a synthesis of poly (MalMA-co-HMA) via free radical copolymerization. Based on $^1$H NMR spectrum (FIG. 3.2A), the ratio of HMA to Fur-MalMA was 93:7, that is, x=7 and y=93 in scheme 3.1). The efficiency of deprotection was proven to be quantitative according to the fact that Diels-Alder linkage protons at 5.2 ppm completely disappeared (FIG. 3.2B).

Shown in FIG. 3.3, scheme 3.2 illustrates a synthesis of polymer@Fluo conjugate via Diels-Alder reaction. Thereafter, Furan functional fluorescein (Fur-Fluo) was prepared via carbodiimide chemistry (FIG. 3.4A). Diels-Alder reaction between poly (MalMA-co-HMA) and Fur-Fluo gave rise to polymer@Fluo conjugate (scheme 3.2). The successful synthesis was confirmed by $^1$H NMR spectroscopy showing both signals from polymer and fluorescein. Moreover, Diels-Alder linkage proton at 5.1 ppm (b) was observed (FIG. 3.4B). 50% of maleimide was successfully functionalized with Fur-Fluo.

Release of fluorescein via rDA reaction was performed at varying temperatures (FIG. 3.5A). As shown in FIG. 3.5B, no release was detected at room temperature, suggested by constant fluorescence intensity at different time. Furthermore, fluorescence intensity increased upon heating at 60° C. while more release was observed at elevated temperature (i.e., 90° C.). Those results shows polymer@Fluo may have a good shelf-life at room temperature. However, the release of fluorescein can be triggered at elevated temperatures.

Subsequently, magnetic nanoparticle and polymer composite micelles were made via flash nanoprecipitation (Scheme 3.3). An illustration of scheme 3.3 showing a preparation of MCNCs via flash nanoprecipitation is shown in FIG. 3.6. Following that, release study was conducted.

Upon demonstrating the release behavior of fluorescein by our platform, we move on to real drug, that is, doxorubicin (DOX). First, we prepared furan functional doxorubicin (Fur-DOX) via two step reactions (FIGS. 3.7A and 3.7B).

Materials and Methods

Materials

Furan maleimide methacrylate (Fur-MalMA), hexyl methacrylate (HMA), azobisisobutyronitrile (AIBN), dioxane, succinic anhydride, dichloromethane (DCM), fluorescein, furfurylamine, doxorubicin, toluene, triethylamine (TEA), N-(3-dimethylaminopropyl)-N'-ethylcarbodiimide hydrochloride (EDC.HCl), and 4-dimethylaminopyridine (DMAP).

Methods

1. Radical Polymerization of Fur-MalMA and HMA

HMA (5.0 g, 30 mmol) and Fur-MalMA (0.90 g, 3.3 mmol) were dissolved into toluene (1 mL). AIBN (50 mg, 0.30 mmol) was subsequently added to the solution followed by purging with nitrogen gas for 20 min. Then the reaction flask was placed in a preheated oil bath at 65° C. for 8 h. The reaction was quenched by exposure to air. Polymer product was collected by precipitation into a large excess of cold methanol and dried under vacuum oven at room temperature.

2. Deprotection of Poly(Fur-MalMA-Co-HMA)

In a typical procedure, poly(Fur-MalMA-co-HPMA) (1.0 g) was suspended in toluene (15 mL) and then heated at 110° C. for 24 h, The reaction was quenched by immersing the vial in ice bath. The final product was collected by precipitation into a large excess of cold methanol and dried under vacuum oven at room temperature.

3. Preparation of Fur-Fluo

In a vial, Fluorescein (1.0 g) was dissolved into DCM (9 mL) and DMF (6 mL). Then EDC.HCl (1.3 g) and DMAP (0.09 g) were added. Following that, the mixture was stirred for 30 min and furfurylamine (0.66 mL) was added dropwise. The reaction was run for 24 hours at room temperature. Upon finishing the reaction, solvent was removed by vacuum and residue was redissolved into ethyl acetate (50 mL). Subsequently, the organic solution was washed by HCl solution (1M) and brine. The organic layer was dried in sodium sulfate and concentrated to yield product as a yellow powder.

4. Diels-Alder Reaction Between Fur-Fluo and Poly (MalMA-Co-HMA)

Poly(MalMA-co-HMA) (0.66 g, 0.26 mmol) and Fur-Fluo (210 mg, 0.52 mmol) were dissolved in DCM (0.6 mL) and DMSO (0.4 mL). The reaction was carried out at 50° C. for 7 days. Upon finishing the reaction, polymer@Fluo was recovered by precipitation into a large excess of methanol three times.

5. Thermal Induced Release of Fluo

In a typical procedure, polymer@Fluo conjugate was suspended in toluene and then incubated in preheated oil bath at predetermined temperatures. The released dye was collected by removal of toluene and dissolving in methanol followed by characterization using fluorescence spectroscopy.

6. Synthesis of Fur-COOH

Succinic anhydride (1.7 g, 17 mmol) was dissolved in DCM (10 mL) and added to furfurylamine (1.0 mL, 10 mmol) dropwise. The reaction mixture was stirred for 3 h at room temperature. The resultant precipitate was collected and washed with DCM and dried.

7. Preparation of Fur-DOX

In a vial, DOX (90 mg) and TEA (68 µL) were dissolved into DMF (2 mL). Then Fur-COOH (0.031 g), EDC.HCl (0.1 g) and DMAP (4 mg) were added. The reaction was run for 24 hours at room temperature. Upon finishing the reaction, solvent was removed by vacuum and residue was redissolved into ethyl acetate (50 mL). Subsequently, the organic solution was washed by acidic saturated sodium chloride solution (pH=2) and brine. The organic layer was dried in sodium sulfate and concentrated to yield product as a dark red powder.

8. Diels-Alder Reaction Between Fur-DOX and Poly (MalMA-co-HMA)

Poly(MalMA-co-HMA) (66 mg, 0.026 mmol of maleimide) and Fur-DOX (37 mg, 0.052 mmol) were dissolved in DCM (0.2 mL) and DMSO (0.1 mL). The reaction was carried out at 50° C. for 7 days. Upon finishing the reaction, polymer@DOX was recovered by precipitation into a large excess of methanol three times.

Example 4

The data in this example show that magnetic composite nanocarrier (MCNC) particles with encapsulated compound release significant amounts of compound in the presence of an alternating magnetic field (AMF). The ability of the particles to retain the compound at body temperature without releasing significant quantities is also shown.

Composition of MCNCs: The MCNC solutions were composed of approximately 5.5 mg/mL polyethylene glycol-block-polylactic acid (PEG-PLA) polymer, 2.25 mg/mL iron oxide nanoparticles, and 3.25 mg/mL fluorescein bound to a maleimide-co-hexyl methacrylate polymer. Fluorescein served as the fluorescent compound.

Conditions used to test release: The MCNCs were suspended in a solution of 75% phosphate-buffered saline (PBS) and 25% methanol by volume. The use of methanol was necessary due to the hydrophobic nature of fluorescein. To begin the release test, 400 µL of MCNC solution was added to Amicon® Ultra 0.5 mL 100 kD centrifugation filters, then centrifuged, and the filtrate was kept in a capped vial. Then, samples were exposed to external heating via a water bath at a set temperature or to an AMF. Samples were centrifugally filtered as before. Then, the fluorescence of 200 µL of each filtrate was recorded at 494 nm excitation and 525 nm emission wavelengths. All conditions were done in triplicate.

Results of release test: The mean value of each condition is plotted with error bars representing the standard deviation in FIGS. 4.1 and 4.2. FIG. 4.1 shows the release as a percent relative to the maximum release condition of 12 hours at 90° C. FIG. 4.2 shows relative fluorescence unit (RFU) values. FIGS. 4.1 and 4.2 show that the compound can be released in an AMF, but is well retained at 37° C.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A composition, comprising:
a micelle including a plurality of magnetic particles, a plurality of amphiphilic polymers, and a plurality of agents, wherein the amphiphilic polymer has a hydrophobic region and a hydrophilic region, wherein the hydrophobic region of the amphiphilic polymer is located in a central region of the micelle and the hydrophilic region is located away from the central region and forms the micelle outer boundary, wherein a portion of magnetic particles and a portion of the agents are located in the central region of the micelle, and wherein the amphiphilic polymer contains thermally labile backbone bonds, wherein the amphiphilic polymer is selected from the group consisting of: PLA-PEG, PLGA-PEG, PCL-PEG, and PTMC-PEG.

2. The composition of claim 1, wherein the hydrophobic region of the amphiphilic polymer includes an agent ($A_{gent}$) bonded to the hydrophobic region of the polymer through thermally degradable group Q.

3. The composition of claim 2, wherein Q is selected from a retro-Diels-Alder-agent group or an azo group.

4. The composition of claim 1, wherein the magnetic particles, the plurality of amphiphilic polymers, and the plurality of agents are not bonded to one another.

5. The composition of claim 2, wherein the hydrophobic region of the amphiphilic polymer is attached to the magnetic particle.

6. The composition of claim 2, wherein the magnetic particle is a material represented by $M^a_x M^b_{(1-x)} Fe_2 O_4$, where each of $M^a$ and $M^b$ are independently selected from Fe, Co, Mn, Zn, Ta, Sr, or Ni, wherein x is 0 to 1, wherein $M^a$ and $M^b$ are different metals.

7. The composition of claim 1, wherein the magnetic particle is a material selected from the group consisting of: $Fe_3O_4$, $\gamma Fe_2O_3$, $\alpha Fe_2O_3$, and $MnFe_2O_4$, $ZnFe_2O_4$, or $Mn_{0.5}Zn_{0.5}Fe_2O_4$.

8. The composition of claim 1, wherein the hydrophilic region includes a polymer group selected from the group consisting of: PEG, poly(zwitterion), poly(betaines), PHPMA, poly(acrylamide)-based polymers, poly(methacrylamide)-based polymers, poly(acrylate)-based polymers, poly(methacrylate)-based polymers, polymers of vinyl esters, polymers of vinyl amides, poly(vinyl alcohol), poly (oxazoline), or a combinations thereof as copolymers or physical mixtures.

9. The composition of claim 1, wherein the agent includes a drug, a therapeutic agent, a radiological agent, or a biological agent.

10. The composition of claim 1, further comprising a targeting agent.

11. A composition, comprising:
a micelle including a plurality of magnetic particles, a plurality of amphiphilic polymers, a plurality of agents, and a targeting agent, wherein the amphiphilic polymer has a hydrophobic region and a hydrophilic region, wherein the hydrophobic region of the amphiphilic polymer is located in a central region of the micelle and the hydrophilic region is located away from the central region and forms the micelle outer boundary, wherein a portion of magnetic particles and a portion of the agents are located in the central region of the micelle, and wherein the amphiphilic polymer contains thermally labile backbone bonds.

12. The composition of claim 11, wherein the amphiphilic polymer is selected from the group consisting of: PLA-PEG, PLGA-PEG, PCL-PEG, and PTMC-PEG as well as a polymer with thermally labile backbone bonds.

13. The composition of claim 11, wherein the hydrophobic region of the amphiphilic polymer includes an agent ($A_{gent}$) bonded to the hydrophobic region of the polymer through thermally degradable group Q.

14. The composition of claim 13, wherein Q is selected from a retro-Diels-Alder-agent group or an azo group.

15. The composition of claim 11, wherein the magnetic particles, the plurality of amphiphilic polymers, and the plurality of agents are not bonded to one another.

16. The composition of claim 13, wherein the hydrophobic region of the amphiphilic polymer is attached to the magnetic particle.

17. The composition of claim 13, wherein the magnetic particle is a material represented by $M^a_x M^b_{(1-x)} Fe_2 O_4$, where each of $M^a$ and $M^b$ are independently selected from Fe, Co, Mn, Zn, Ta, Sr, or Ni, wherein x is 0 to 1, wherein $M^a$ and $M^b$ are different metals.

18. The composition of claim 11, wherein the magnetic particle is a material selected from the group consisting of: $Fe_3O_4$, $\gamma Fe_2O_3$, $\alpha Fe_2O_3$, and $MnFe_2O_4$, $ZnFe_2O_4$, or $Mn_{0.5}Zn_{0.5}Fe_2O_4$.

19. The composition of claim 11, wherein the hydrophilic region includes a polymer group selected from the group consisting of: PEG, poly(zwitterion), poly(betaines), PHPMA, poly(acrylamide)-based polymers, poly(methacrylamide)-based polymers, poly(acrylate)-based polymers, poly(methacrylate)-based polymers, polymers of vinyl esters, polymers of vinyl amides, poly(vinyl alcohol), poly (oxazoline), or a combinations thereof as copolymers or physical mixtures.

20. The composition of claim 11, wherein the agent includes a drug, a therapeutic agent, a radiological agent, or a biological agent.

* * * * *